United States Patent
Mante et al.

(10) Patent No.: US 10,851,000 B2
(45) Date of Patent: Dec. 1, 2020

(54) SYSTEMS FOR PRODUCING HIGH-CONCENTRATION OF DISSOLVED OZONE IN LIQUID MEDIA

(71) Applicants: L'Air Liquide, Société Anonyme pour l'Etude et l'Exploitation des Procédés Georges Claude, Paris (FR); American Air Liquide, Inc., Fremont, CA (US)

(72) Inventors: Jan Mante, Muenster (DE); Vasuhi Rasanayagam, Newark, DE (US); Midhun Joy, Bear, DE (US); Rovshan Mahmudov, Newark, DE (US); Siavash Isazadeh, Cambridge, MA (US)

(73) Assignees: L'Air Liquide, Société Anonyme pour l'Etude et l'Exploitation des Procédés Georges Claude, Paris (FR); American Air Liquide, Inc., Fremont, CA (US)

(*) Notice: Subject to any disclaimer, the term of this patent is extended or adjusted under 35 U.S.C. 154(b) by 0 days.

(21) Appl. No.: 16/046,805

(22) Filed: Jul. 26, 2018

(65) Prior Publication Data
US 2019/0300405 A1   Oct. 3, 2019

Related U.S. Application Data

(63) Continuation-in-part of application No. 15/939,114, filed on Mar. 28, 2018, now abandoned.

(51) Int. Cl.
  *C02F 1/78* (2006.01)
  *C02F 1/72* (2006.01)
  (Continued)

(52) U.S. Cl.
  CPC .......... *C02F 1/78* (2013.01); *A01N 59/00* (2013.01); *A61L 2/183* (2013.01); *B01F 3/0876* (2013.01);
  (Continued)

(58) Field of Classification Search
  None
  See application file for complete search history.

(56) References Cited

U.S. PATENT DOCUMENTS

3,542,342 A   11/1970  Barron
4,252,654 A    2/1981  Leitzke et al.
(Continued)

FOREIGN PATENT DOCUMENTS

| EP | 0 208 253 | 1/1987 |
| EP | 0 561 458 | 9/1993 |
| WO | WO 97 14657 | 4/1997 |

OTHER PUBLICATIONS

Isazadeh, S., Biosolids minimization by partial ozonation of return activated sludge: model development and bacterial population dynamics. A thesis submitted to McGill University in Partial Fulfillment of the Requirements of the Degree of Doctor of Philosophy, Department of Civil Engineering and Applied Mechanics, Montreal, Quebec, Canada, Aug. 2014, i-xxv, 1-50, 114, 169.
(Continued)

*Primary Examiner* — Richard C Gurtowski
(74) *Attorney, Agent, or Firm* — Yan Jiang

(57) ABSTRACT

Disclosed are systems for continuous production of ozone strong water, the systems comprising an injection device that injects an acidification agent into a pressurized feed liquid, a diffuser device that injects ozone into a body of the acidic pressurized feed water, and injection nozzles each controlled by a valve that adjust a flow rate of the ozone strong water discharged from a dissolution column to match a flow rate of the acidic pressurized feed water fed to the dissolution column, thereby maintaining a start-up mode in an upper portion of the dissolution column that favors a high efficiency of ozone mass transfer and a steady-state mode in a lower portion of the dissolution column that favors a high dissolved ozone concentration coexistent in the body of the
(Continued)

acidic pressurized liquid, wherein a concentration gradient of dissolved ozone is formed along a height of the body of the acidic pressurized liquid.

31 Claims, 22 Drawing Sheets

(51) Int. Cl.
| | |
|---|---|
| *A01N 59/00* | (2006.01) |
| *A61L 2/18* | (2006.01) |
| *B01F 3/08* | (2006.01) |
| *B01F 3/20* | (2006.01) |
| *B01F 5/10* | (2006.01) |
| *B01F 15/00* | (2006.01) |
| *C01B 13/10* | (2006.01) |
| *C02F 1/32* | (2006.01) |
| *B01D 53/22* | (2006.01) |
| *A61L 2/20* | (2006.01) |

(52) U.S. Cl.
CPC ............... *B01F 3/20* (2013.01); *B01F 5/102* (2013.01); *B01F 15/00162* (2013.01); *C01B 13/10* (2013.01); *C02F 1/725* (2013.01); *A61L 2/202* (2013.01); *B01D 53/22* (2013.01); *B01F 2215/008* (2013.01); *C02F 1/32* (2013.01); *C02F 2201/782* (2013.01); *C02F 2201/784* (2013.01); *C02F 2303/04* (2013.01)

(56) References Cited

U.S. PATENT DOCUMENTS

| | | | |
|---|---|---|---|
| 5,275,742 | A | 1/1994 | Satchell, Jr. et al. |
| 5,487,835 | A | 1/1996 | Shane |
| 5,591,349 | A | 1/1997 | Ikeda et al. |
| 5,637,231 | A | 6/1997 | Hill et al. |
| 6,146,524 | A | 11/2000 | Story |
| 6,190,436 | B1 | 2/2001 | Ji et al. |
| 6,197,091 | B1 | 3/2001 | Ji et al. |
| 6,423,235 | B1 | 7/2002 | Shimoi et al. |
| 6,461,522 | B1 | 10/2002 | Pak et al. |
| 6,464,867 | B1 | 10/2002 | Morita et al. |
| 6,485,769 | B2 | 11/2002 | Audy et al. |
| 6,712,951 | B2 | 3/2004 | Andrews et al. |
| 7,022,225 | B1 | 4/2006 | Clawson et al. |
| 9,248,415 | B2 | 2/2016 | Osborn |
| 2002/0110508 | A1 | 8/2002 | Campo et al. |
| 2003/0042631 | A1 | 3/2003 | Nelson et al. |
| 2007/0034230 | A1 | 2/2007 | Gottschalk et al. |
| 2007/0047383 | A1 | 3/2007 | Williams et al. |
| 2010/0219137 | A1 | 9/2010 | Lacasse |
| 2011/0031187 | A1 | 2/2011 | Shim |
| 2011/0186495 | A1 | 8/2011 | Robinson et al. |
| 2012/0164024 | A1 | 6/2012 | Uhm |
| 2013/0026110 | A1 | 1/2013 | Osborn |
| 2015/0303053 | A1 | 10/2015 | Tokoshima et al. |
| 2016/0361693 | A1 | 12/2016 | Hayashi et al. |

OTHER PUBLICATIONS

The Linde Group, Pure water knowledge: gases and application technologies for water treatment, Linde AG, Linde Gases Division, Unterschlessheim, Germany, 2017, 1-15.

MacAuley, J.J. et al., Disinfection of swine wastewater using chlorine, ultraviolet light and ozone, Water Research, Elsevier, Jan. 2006, vol. 40, No. 10, 2017-2026.

One Water Ohio, $CO_2$ injection methods and equipment of pH control, Apr. 4, 2017, retrieved from http://www.onewaterohio.org/docs/1335.the_basics_of_carbon_dioxide_injection_methods:_dirth.pdf/, 22 pages.

Rodriguez, A. et al., Ozone-based technologies in water and wastewater treatment, Hdg Env Chem Feb. 7, 2008, vol. 5, DOI: 10.1007/698_5_103, 31 pages.

Yixing Holly Technology Co, Ltd, Fine bubble disc diffuser, Apr. 20, 2017, retrieved from http://www.hollyep.com/html/Fine%20Bubble%20Diffusers_Aerators/915, 5 pages.

International Search Report and Written Opinion for corresponding PCT/US2019/023846, dated May 29, 2019.

International Search Report and Written Opinion for related PCT/US2019/023867, dated Jun. 11, 2019.

International Search Report and Written Opinion for related PCT/US2019/023888, dated Jun. 12, 2019.

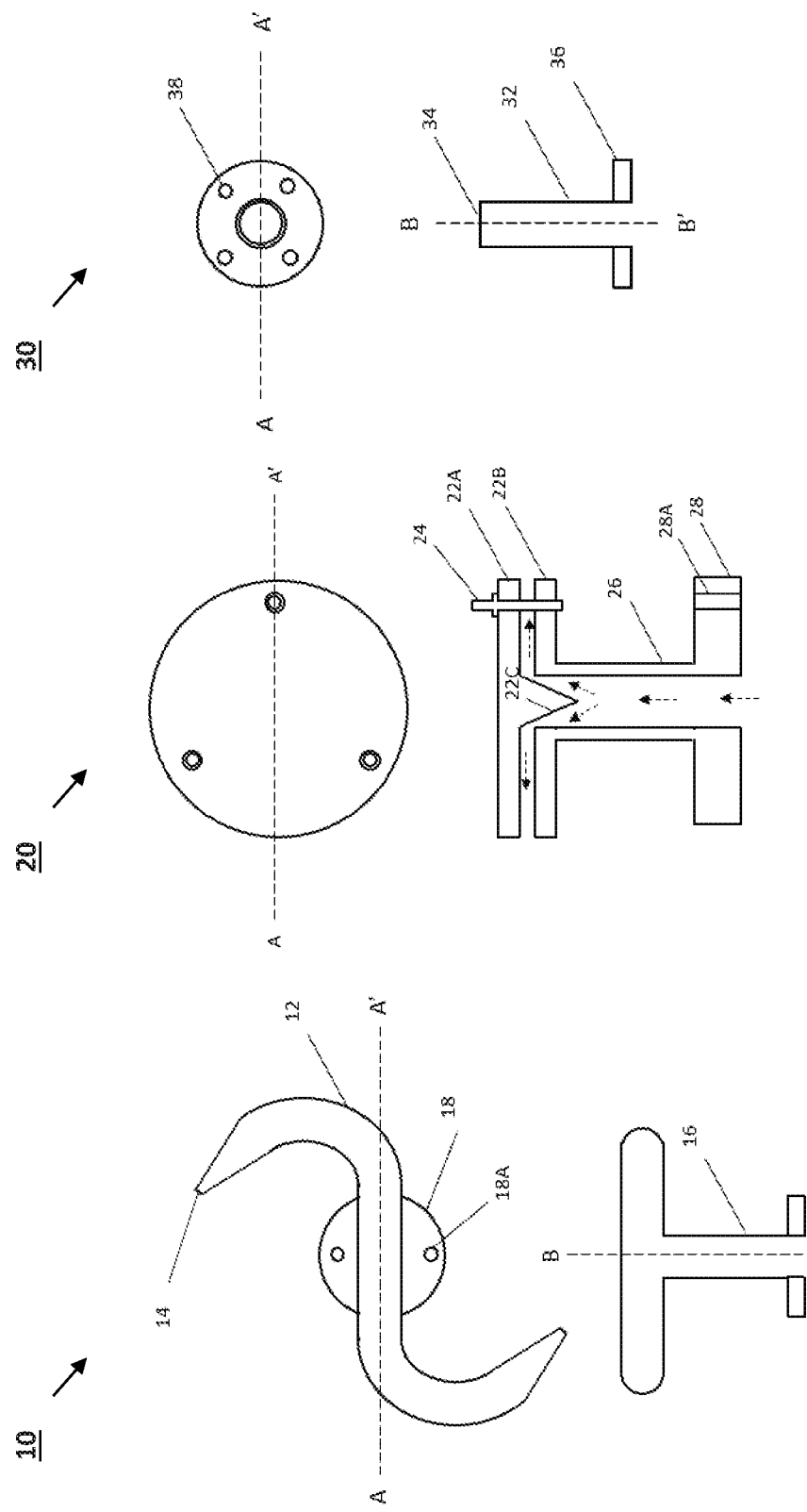

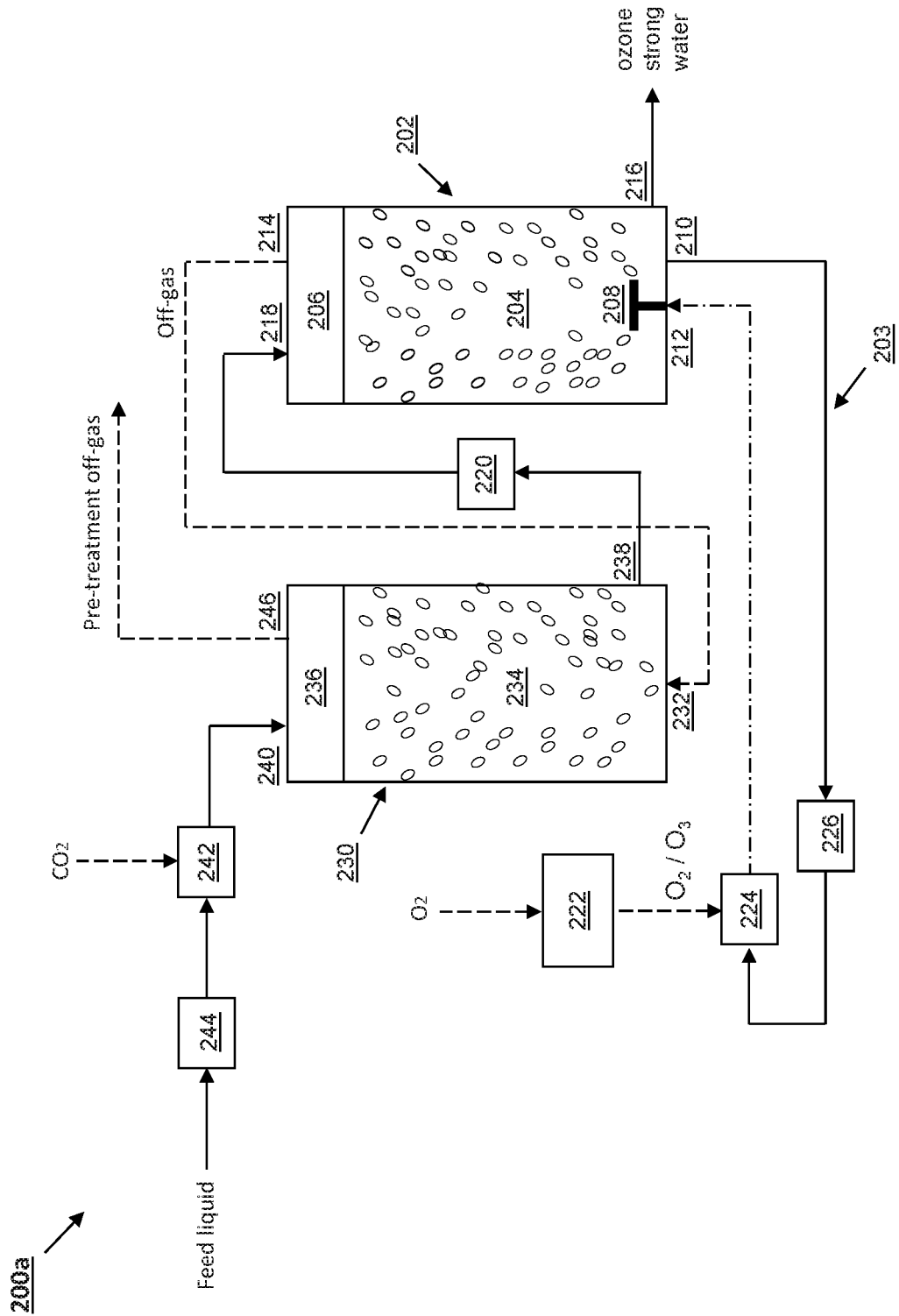

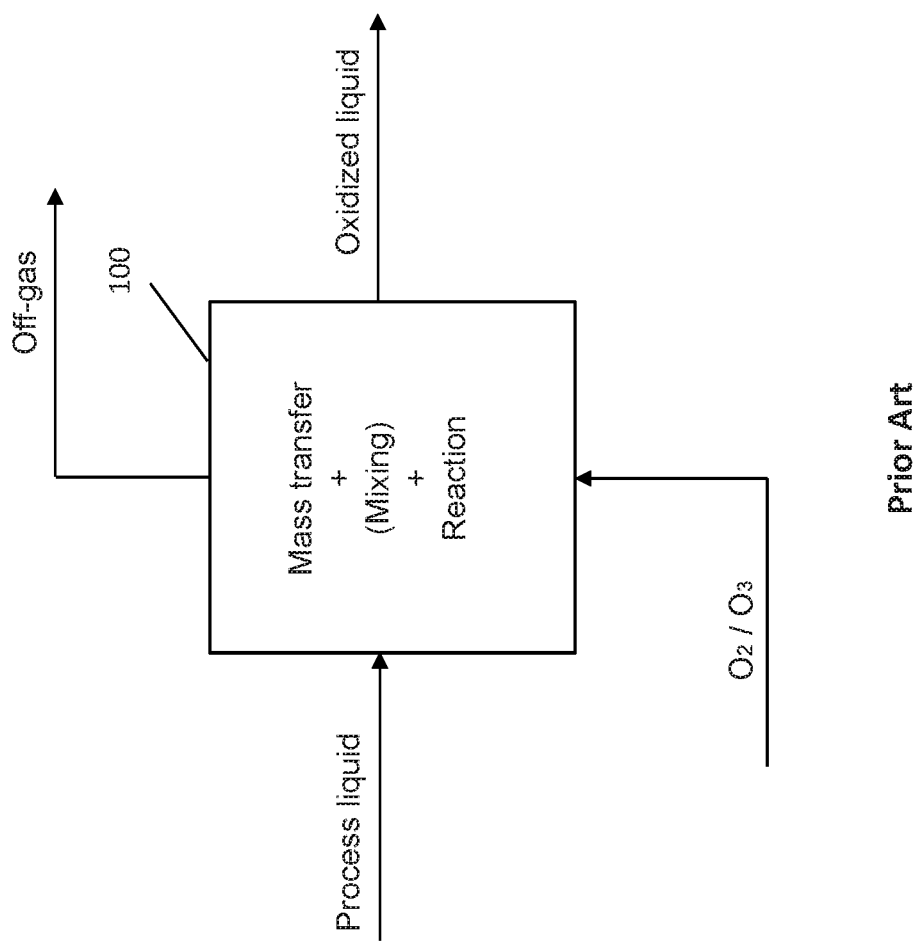

SYSTEMS FOR PRODUCING HIGH-CONCENTRATION OF DISSOLVED OZONE IN LIQUID MEDIA

CROSS REFERENCE TO RELATED APPLICATIONS

This application is a continuation-in-part application of, and claims the benefit of U.S. patent application Ser. No. 15/939,114, filed Mar. 28, 2018, herein incorporated by reference in its entirety for all purposes.

FIELD OF THE INVENTION

The present invention relates to systems for dissolving ozone in a liquid media, in particular, for maximizing the concentration of dissolved ozone in a liquid medium, such as water, to produce ozone strong water for use as liquid oxidant. The ozone strong water is a pressurized gas-free high concentrated or saturated or close to saturated (e.g. within 10% of saturation concentration, such as 5% or 1% or 0.1%) ozone dissolved water, which under atmospheric conditions is supersaturated.

BACKGROUND

Liquid oxidation is used for oxidizing a compound while in solution. In a typical liquid oxidation process, an oxidizing substance such as ozone, nitrogen dioxide, fluorine, chlorine, bromine, etc. is incorporated into liquid or contaminated liquid medium to destroy chemical contaminants in place. It can be used to remediate a variety of organic and inorganic compounds, including some that are resistant to natural degradation. One of the common oxidants used in this process is ozone ($O_3$).

Ozone based oxidation treatment is common in industrial world. Ozone is being used for oxidation of several chemical compounds in pharmaceutical industries. It may also be used for bleaching and for killing microorganisms. Most of the ozone reactions happen in liquid medium. Since ozone is commercially generated in the gas-phase using an ozone generator, it first needs to be dissolved in water or liquid medium (so-called mass transfer). This dissolved ozone in water or liquid medium is used as an oxidant to react with compounds for oxidation. In industry, dissolved ozone water or liquid medium can be used, but is not limited to the following areas:
- remove micro-pollutants and oxidation of hard-to-degrade organic components in tertiary water;
- chemically attack contaminants in water (iron, arsenic, hydrogen sulfide, nitrites, complex organics) and decolonization;
- disinfect water in place of chlorine, such as, drinking water, process liquid, etc.;
- provide an aid to flocculation (agglomeration of molecules, which aids in filtration, where iron and arsenic are removed);
- manufacture chemical compounds via chemical synthesis;
- wash fresh fruits and vegetables to kill yeast, mold and bacteria; and
- bleach pulp and paper.

Currently, processes of ozone dissolution, mixing and reaction for ozone based wastewater treatment take place in a single reactor, for example, in a big concrete basin in wastewater treatment plants (WWTPs). FIG. 17 is a block diagram of a common ozone reactor system designed to have all processes, dissolution (mass transfer), mixing and reaction, in a single reactor 100. In those systems the ozone gas is usually injected via bubble diffusors or pump-injector systems into the ozone reactor. Note herein that in the single reactor 100, a separate mixing step is not necessary as the ozone gas is dissolved directly into the process water to be treated. Examples of such reactors are pilot plants manufactured by Wedeco: WWTP Regensdorf & WWTP Lausanne in Switzerland, and WWTP Emscher Verbund and WWTP Duisburg in Germany. Such a system normally has a large volume (for example, 333 $m^3$) of reactor and hydraulic retention times between 20 min and 40 min are common. Depending on the different oxidation applications, usual ozone dosages range between 2 g and 200 g of ozone per $m^3$ of process liquid to be treated. In addition, the above mentioned single reactors typically operate under atmosphere pressure around 1 bar. Hence, the undissolved ozone and oxygen in an off-gas stream from the single reactor cannot be recovered without further pressurizing, resulting in a wastage of ozone gas and/or oxygen gas as well as energy consumed to generate ozone in the systems.

In general, it is known the rate of dissolution of ozone in water (also called gas-to-liquid mass transfer rate) is the rate limiting step in comparison to the rate of reaction of dissolved ozone with oxidizable constituents in a process liquid. In many industry processes (e.g., use of ozone for advanced or tertiary treatment of waste water) the dissolution of ozone in water or ozone mass transfer from gas to liquid phase is the rate limiting step in the entire process. In addition, as both dissolution and reaction occurs in the same reactor, they are not optimized for either dissolution or the reaction process. Thus, decoupling of equipment in a system being employed for dissolution, mixing and reaction of ozone would lead to process flexibility and enable the system operation under more economical and technically optimized conditions and/or enable more efficient ozone gas recycling.

Recently, significant attempts have been allocated towards achievement of high dissolved ozone levels or concentrations in an aqueous medium.

U.S. Pat. No. 7,022,225 to Clawson et al. disclose an apparatus and system for mixing and separating ozonated water. The apparatus is useful for cycling sanitizing pre-treated ozonated water to a body of water. The apparatus includes a separating vessel including a mixing tower with a diffuser device for enhancing mixing of pre-treated ozonated water without increasing turbulence in the separating vessel. The separating vessel is sealed with an off-gas vent. An ozone destruct assembly includes a return line for passing a treated off-gas into the body of water.

U.S. Pat. No. 5,637,231A to Hill et al. disclose a photocatalytic oxidation and ozone catalyst system utilizing ultraviolet light and ozone in the treatment of waste and wastewater to destroy pathogens and to break down most hydrocarbons and other chemicals into non-hazardous forms. The ozone interacts at a venturi before the ultraviolet light is being used as a catalyst to break apart the double bonds of ketones, aldehydes, esters, and carboxylic acids. Following initial treatment, the wastewater is pumped into the pressurized ozone enhancement vessel where vapor oxidation of the polluting chemicals occurs. The enhancement vessel comprises a series of ozone resonator plates having ozone distribution manifolds that spray wastewater with ozone.

U.S. Pat. No. 6,461,522 to Pak et al. disclose that wastewater streams containing pollutants are economically and efficiently treated at ambient temperature and pressure with hydrogen peroxide, oxygen or ozone in the presence of a heterogeneous catalyst.

WO 1997014657 to Bargratt et al. disclose removing contaminants from wastewater by an advanced oxidation process in which the wastewater is contacted with ozone in the absence of a catalyst to oxidize ozone-oxidizable contaminants and to dissolve ozone in the water, and the resultant ozone-containing water is contacted with a solid ozone activating catalyst to oxidize ozone refractory contaminants in the water. Effluent from the catalyst treatment can be contacted with ozone and recycled for further contact with the catalyst.

EP 0561458 to van Staveren discloses processes and apparatus for the purification of water, in which oxygen/ozone-gas mixture is introduced under high pressure in the water to be purified, and the obtained oxygen/ozone-gas mixture enriched water is passed to a purification stage which comprises at least one reactor. Not or insufficiently degraded contaminants are retained by a membrane filter unit and recycled to the purification stage.

U.S. Pat. Nos. 6,190,436 and 6,197,091 to Ji et al. disclose using a membrane separation unit containing an elastomeric polymer membrane to produce an ozone-enriched gas stream and an oxygen-enriched gas stream. An ozone-oxygen gas mixture is produced by passing oxygen into an ozone generator. The ozone-enriched gas is contacted with ozone-reactive substances, thereby oxidizing the substances. The oxygen-enriched gas stream is recycled to the ozone generator. Prior to being recycled, the oxygen-enriched stream may be purified to remove gaseous impurities which permeate through the membrane from the liquid or gas stream being treated.

U.S. Pat. No. 9,248,415 to Osborn et al. discloses systems and methods for maximizing the concentration of dissolved ozone gas in water by periodically or continuously dissolving ozone in the liquid that is sprayed through a gas feed of ozone and oxygen while removing excess oxygen gas from the headspace of the saturation tank used in the dissolution system. The dissolved ozone concentration using gas bleed-off system is nearly 50 mg/L at exit of the dissolution tank.

SUMMARY

There is disclosed a system for continuous production of a gas-free liquid containing ozone, the system comprising a first gas injection device configured and adapted to inject an acidification agent into a pressurized feed liquid stream to maintain a pH value of the pressurized feed water stream below 7, b) a dissolution column including, (i) a pressure vessel, configured and adapted to contain a body of acidic pressurized liquid and an off gas in a headspace above the body of the acidic pressurized liquid, (ii) an inlet, configured and adapted to permit passage of the pressurized feed liquid stream, after the injection of the acidification agent, into the pressure vessel through the headspace, (iii) an off-gas vent, configured and adapted to release the off gas contained in the headspace of the pressure vessel so as to maintain a pressure of the pressure vessel within a pre-determined pressure range, and (iv) an outlet, configured and adapted to discharge the gas-free liquid containing ozone from the pressure vessel, c) a fluid recirculation loop having a fluid inlet, fluidly connected to the dissolution column, configured and adapted to receive a fluid from the dissolution column, a second gas injection device, configured and adapted to inject ozone into the fluid being recirculated by the fluid recirculation loop, and a fluid injection device, within the pressure vessel, mounted on the bottom of the pressure vessel, configured and adapted to diffuse the fluid, after the injection of ozone, into the body of the acidic pressurized liquid in the pressure vessel, thereby injecting ozone therein, d) a controller, configured and adapted to adjust a flow rate of the acidic pressurized feed liquid stream fed to the inlet of dissolution column so as to yield an inflow of the acidic pressurized feed liquid stream that enables to continuously produce the gas-free liquid containing ozone, and e) at least one injection nozzles each controlled by a valve, fluidly connected to the outlet of the dissolution column, configured and adapted to adjust a flow rate of the produced gas-free liquid containing ozone discharged from the outlet of the dissolution column to match the flow rate of the acidic pressurized feed liquid stream fed to the inlet of the dissolution column so as to maintain a start-up mode in an upper portion of the pressure vessel that favors a high efficiency of ozone mass transfer into the acidic pressurized liquid and a steady-state mode in a lower portion of the pressure vessel that favors a high dissolved ozone concentration in the acidic pressurized liquid coexistent in the body of the acidic pressurized liquid in the pressure vessel, wherein a concentration gradient of dissolved ozone is formed along a height of the body of the acidic pressurized liquid.

There is also disclosed a system for continuous production of an ozone strong water, the system comprising a first gas injection device configured and adapted to inject an acidification agent into a pressurized feed water stream to maintain a pH value of the pressurized feed water stream below 7, b) a dissolution column including (i) a pressure vessel, configured and adapted to contain a body of acidic pressurized water and an off gas in a headspace above the body of the acidic pressurized water, (ii) an inlet, configured and adapted to permit passage of the pressurized feed water stream, after the injection of the acidification agent, into the pressure vessel through the headspace, (iii) an off-gas vent, configured and adapted to release the off gas contained in the headspace of the pressure vessel so as to maintain a pressure of the pressure vessel within a pre-determined pressure range, and (iv) an outlet, configured and adapted to discharge the ozone strong water from the pressure vessel, c) a fluid recirculation loop having a fluid inlet, fluidly connected to the dissolution column, configured and adapted to receive a fluid from the dissolution column, a second gas injection device, configured and adapted to inject ozone into the fluid being recirculated by the fluid recirculation loop, and a fluid injection device, within the pressure vessel, mounted on the bottom of the pressure vessel, configured and adapted to diffuse the fluid, after the injection of ozone, into the body of the acidic pressurized water in the pressure vessel, thereby injecting ozone therein, d) a controller, configured and adapted to adjust a flow rate of the acidic pressurized feed water stream fed to the inlet of dissolution column so as to yield an inflow of the acidic pressurized feed water stream that enables to continuously produce the ozone strong water, and e) at least one injection nozzles each controlled by a valve, fluidly connected to the outlet of the dissolution column, configured and adapted to adjust a flow rate of the produced ozone strong water discharged from the outlet of the dissolution column to match the flow rate of the acidic pressurized feed water stream fed to the inlet of the dissolution column so as to maintain a start-up mode in an upper portion of the pressure vessel that favors a high efficiency of ozone mass transfer into the acidic pressurized water and a steady-state mode in a lower portion of the pressure vessel that favors a high dissolved ozone concentration in the acidic pressurized water coexistent in the body of the acidic pressurized water in the pressure vessel, wherein a concentration gradient of dissolved ozone is formed along a height of the body of the acidic pressurized water.

There is also disclosed a system for continuous production of a gas-free oxidant for liquid oxidation processes, the system comprising a gas injection device configured and adapted to inject an acidification agent into a pressurized feed liquid stream to maintain a pH value of the pressurized feed water stream below 7, b) a dissolution column including (i) a pressure vessel, configured and adapted to contain a body of acidic pressurized liquid and an off gas in a headspace above the body of the acidic pressurized liquid, (ii) an inlet, configured and adapted to permit passage of the pressurized feed liquid stream, after the injection of the acidification agent, into the pressure vessel through the headspace, (iii) a fluid diffuser device within the pressure vessel, mounted on the bottom of the pressure vessel, configured and adapted to diffuse an oxidant gas into the body of the acidic pressurized liquid in the pressure vessel to dissolve the oxidant gas therein, thereby producing the gas-free oxidant for liquid oxidation processes, and (iv) an off-gas vent, configured and adapted to release the off gas contained in the headspace of the pressure vessel so as to maintain a pressure of the pressure vessel within a pre-determined pressure range, and (iv) an outlet, configured and adapted to discharge the gas-free oxidant for liquid oxidation processes from the pressure vessel, c) a controller, configured and adapted to adjust a flow rate of the acidic pressurized feed liquid stream fed to the inlet of dissolution column so as to yield an inflow of the acidic pressurized feed liquid stream that enables to continuously produce the gas-free oxidant for liquid oxidation processes, and e) at least one injection nozzles each controlled by a valve, fluidly connected to the outlet of the dissolution column, configured and adapted to adjust a flow rate of the produced gas-free oxidant for liquid oxidation processes discharged from the outlet of the dissolution column to match the flow rate of the acidic pressurized feed liquid stream fed to the inlet of the dissolution column so as to maintain a start-up mode in an upper portion of the pressure vessel that favors a high efficiency of ozone mass transfer into the acidic pressurized liquid and a steady-state mode in a lower portion of the pressure vessel that favors a high dissolved ozone concentration in the acidic pressurized liquid coexistent in the body of the acidic pressurized liquid in the pressure vessel, wherein a concentration gradient of dissolved ozone is formed along a height of the body of the acidic pressurized liquid.

Any one or more of the above systems may include one or more of the following aspects:
the acidification agent is $CO_2$ gas;
the acidification agent is a mineral acid;
the mineral acid is HCl, $H_2SO_4$, $HNO_3$, or other acids;
a pH value in the dissolution column is below 7;
a pH value in the dissolution column ranges 2 to 6.95;
a pH value in the dissolution column ranges 3 to 6;
a pH value in the dissolution column is about 5;
a pH value in the dissolution column is about 4;
a pH value of the body of acidic pressurized liquid is below 7;
a pH value of the body of acidic pressurized liquid ranges 2 to 6.95;
a pH value of the body of acidic pressurized liquid ranges 3 to 6;
a pH value of the body of acidic pressurized liquid is about 5;
a pH value of the body of acidic pressurized liquid is about 4;
a pH value of the body of acidic pressurized water is below 7;
a pH value of the body of acidic pressurized water ranges 2 to 6.95;
a pH value of the body of acidic pressurized water ranges 3 to 6;
a pH value of the body of acidic pressurized water is about 5;
a pH value of the body of acidic pressurized water is about 4;
a pH value of the ozone strong water is below 7;
a pH value of the ozone strong water ranges 2 to 6.95;
a pH value of the ozone strong water ranges 4 to 6;
a pH value of the ozone strong water is about 5;
a pH value of the ozone strong water is about 4;
a pH value of the gas-free liquid containing dissolved ozone is below 7;
a pH value of the gas-free liquid containing dissolved ozone ranges 2 to 6.95;
a pH value of the gas-free liquid containing dissolved ozone ranges 4 to 6;
a pH value of the gas-free liquid containing dissolved ozone is about 5;
a pH value of the gas-free liquid containing dissolved ozone is about 4;
a pH value of the gas-free liquid oxidant is below 7;
a pH value of the gas-free liquid oxidant ranges 2 to 6.95;
a pH value of the gas-free liquid oxidant ranges 4 to 6;
a pH value of the gas-free liquid oxidant is about 5;
a pH value of the gas-free liquid oxidant is about 4;
a pH value of the gas-free oxidant is below 7;
a pH value of the gas-free oxidant ranges 2 to 6.95;
a pH value of the gas-free oxidant ranges 4 to 6;
a pH value of the gas-free oxidant is about 5;
a pH value of the gas-free oxidant is about 4;
the pre-determined pressure range of the dissolution column is from 2 to 7 barg;
the pre-determined pressure range of the dissolution column is from 3 to 6 barg;
the pre-determined pressure range of the dissolution column is about 5 barg;
a pressure of the ozone strong water ranges from 2 to 7 barg;
a pressure of the ozone strong water ranges from 3 to 6 barg;
a pressure of the ozone strong water is about 5 barg;
a pressure of the ozone dissolved liquid ranges from 2 to 7 barg;
a pressure of the ozone dissolved liquid ranges from 3 to 6 barg;
a pressure of the ozone dissolved liquid is about 5 barg;
a pressure of the gas-free liquid containing dissolved ozone is from 2 to 7 barg;
a pressure of the gas-free liquid containing dissolved ozone is from 3 to 6 barg;
a pressure of the gas-free liquid containing dissolved ozone is about 5 barg;
a pressure of the gas-free liquid oxidant ranges from 2 to 7 barg;
a pressure of the gas-free liquid oxidant ranges from 3 to 6 barg;
a pressure of the gas-free liquid oxidant is about 5 barg;
a pressure of the liquid oxidant ranges from 2 to 7 barg;
a pressure of the liquid oxidant ranges from 3 to 6 barg;
a pressure of the liquid oxidant is about 5 barg;

a pressure of the gas-free oxidant ranges from 2 to 7 barg;
a pressure of the gas-free oxidant ranges from 3 to 6 barg;
a pressure of the gas-free oxidant is about 5 barg;
a temperature of the dissolution column ranges from 10° C. to 30° C.;
a temperature of the dissolution column ranges from 15° C. to 25° C.;
a temperature of the dissolution column is at about 20° C.;
a temperature of the dissolution column is approximately at ambient temperature;
the temperature of the acidic pressurized liquid ranges from 10° C. to 30° C.;
the temperature of the acidic pressurized liquid ranges from 15° C. to 25° C.;
the temperature of the acidic pressurized liquid is at about 20° C.;
the temperature of the acidic pressurized liquid is about at ambient temperature;
the temperature of the acidic pressurized water is from 10° C. to 30° C.;
the temperature of the acidic pressurized water ranges from 15° C. to 25° C.;
the temperature of the acidic pressurized water is at about 20° C.;
the temperature of the acidic pressurized water is about at ambient temperature;
a temperature of the ozone strong water ranges from 10° C. to 30° C.;
a temperature of the ozone strong water ranges from 15° C. to 25° C.;
a temperature of the ozone strong water is about 20° C.;
a temperature of the ozone strong water is approximately at ambient temperature;
a temperature of the gas-free liquid containing ozone is from 10° C. to 30° C.;
a temperature of the gas-free liquid containing ozone is from 15° C. to 25° C.;
a temperature of the gas-free liquid containing ozone is about 20° C.;
a temperature of the gas-free liquid containing dissolved ozone is about at ambient temperature;
a temperature of the gas-free liquid oxidant ranges from 10° C. to 30° C.;
a temperature of the gas-free liquid oxidant ranges from 15° C. to 25° C.;
a temperature of the gas-free liquid oxidant is about 20° C.;
a temperature of the gas-free liquid oxidant is about at ambient temperature;
a temperature of the liquid oxidant ranges from 10° C. to 30° C.;
a temperature of the liquid oxidant ranges from 15° C. to 25° C.;
a temperature of the liquid oxidant is about 20° C.;
a temperature of the liquid oxidant is approximately at ambient temperature;
a temperature of the gas-free oxidant ranges from 10° C. to 30° C.;
a temperature of the gas-free oxidant ranges from 15° C. to 25° C.;
a temperature of the gas-free oxidant is about 20° C.;
a temperature of the gas-free oxidant is approximately at ambient temperature;
the pressurized feed liquid stream is a stream of pressurized fresh water, tap water, process water, effluent water, municipal and industrial wastewater, wastewater already treated by a secondary treatment process, aqueous solutions, organic solvents, or the like;
the pressurized feed water stream is a stream of pressurized fresh water, tap water, process water, effluent water, municipal and industrial wastewater, wastewater already treated by a secondary treatment process, or the like;
the feed liquid stream is a stream of fresh water, tap water, process water, effluent water, municipal and industrial wastewater, wastewater already treated by a secondary treatment process, aqueous solutions, organic solvents, or the like;
the feed water stream is a stream of fresh water, tap water, process water, effluent water, municipal and industrial wastewater, wastewater already treated by a secondary treatment process, or the like;
The feed liquid is composed of water, such as fresh water, tap water, process water, effluent water, municipal and industrial wastewater, wastewater already treated by the secondary treatment process, or the like;
The feed liquid is composed of aqueous solutions, organic solvents, etc.;
the feed liquid is an acidic feed liquid, such as acidic industrial wastewaters from phosphate manufacturing, mining, steel mills, or the like;
The process liquid is composed of water, such as fresh water, tap water, process water, effluent water, municipal and industrial wastewater, wastewater already treated by the secondary treatment process, aqueous solutions, organic solvents, or the like;
The process liquid is composed of water, such as fresh water, tap water, process water, effluent water, municipal and industrial wastewater, wastewater already treated by the secondary treatment process, or the like;
The process liquid is composed of aqueous solutions, organic solvents, etc.;
the process liquid is an acidic feed liquid, such as acidic industrial wastewaters from phosphate manufacturing, mining, steel mills, or the like;
the process liquid includes the same type of water or liquid as the feed liquid which carries components that should be oxidized;
the feed liquid and the process liquid are originated from the same source;
the gas-free liquid containing dissolved ozone is ozone strong water;
the liquid containing dissolved ozone is gas-free;
the gas-free liquid oxidant is ozone strong water;
the liquid oxidant is gas-free;
the gas-free oxidant is ozone strong water;
the oxidant is gas-free;
the ozone strong water is gas-free;
the ozone strong water is a pressurized gas-free high concentrated or saturated or close to saturated (e.g., within 10% of saturation concentration, such as 5% or 1% or 0; 1%) dissolved ozone water which is supersaturated if at atmospheric pressure;
the off-gas stream from the dissolution column contains undissolved ozone;
the off-gas stream from the dissolution column contains oxygen;
the off-gas stream from the dissolution column contains undissolved $CO_2$;
the step of b) comprises the sub-steps of b1) feeding the pressurized feed water stream after injection of the acidification agent into to a pre-treatment dissolution column to form a body of pre-treatment acidic pressurized water, thereby producing pre-treated ozonated water therein, b2) pumping the produced pre-treated ozonated water into the dissolution column, b3) injecting the off-gas stream released from the dissolution column into the body of pre-treatment acidic pressurized water to produce a pre-treated ozonated water in the pre-treatment dissolution column, and b4) maintaining a pressure of the pre-treatment dissolution column lower than that of the dissolution column through releasing an off-gas stream from the pre-treatment dissolution column;

the step of ii) comprises the sub-steps of ii1) feeding the pressurized feed liquid stream, after injection of the acidification agent, to a pre-treatment dissolution column to form a body of pre-treatment acidic pressurized liquid, thereby producing pre-treated ozonated liquid therein, ii2) pumping the produced pre-treated ozonated liquid into the dissolution column, ii3) injecting the off-gas stream that contains ozone released from the dissolution column into the body of pre-treatment acidic pressurized liquid to produce a pre-treated ozonated liquid in the pre-treatment dissolution column, and ii4) maintaining a pressure of the pre-treatment dissolution column lower than that of the dissolution column through releasing an off-gas stream from the pre-treatment dissolution column;

the off-gas from the main dissolution column contains undissolved ozone;

the off-gas from the main dissolution column contains oxygen;

the off-gas from the main dissolution column contains undissolved $CO_2$;

the pre-treatment off-gas stream from the pre-treatment dissolution column contains little to no ozone;

the pre-treatment off-gas stream from the pre-treatment dissolution column contains oxygen;

the pre-treatment off-gas stream from the pre-treatment dissolution column contains undissolved $CO_2$;

the pH value of the pressurized acidic pre-treated liquid in the pre-treatment dissolution column is maintained approximately the same as that of the acidic pressurized liquid in the main dissolution column;

the pH value of the pressurized acidic pre-treated water in the pre-treatment dissolution column is maintained higher than the pH value of the acidic pressurized water in the main dissolution column;

the pH value of the pressurized acidic pre-treated liquid is below 7;

the pH value of the pressurized acidic pre-treated liquid ranges 2 to 6.95;

the pH value of the pressurized acidic pre-treated liquid ranges 4 to 6;

the pH value of the pressurized acidic pre-treated liquid is about 5;

the pH value of the pressurized acidic pre-treated liquid is about 4;

the pH value of the pressurized acidic pre-treated water is below 7;

the pH value of the pressurized acidic pre-treated water ranges 2 to 6.95;

the pH value of the pressurized acidic pre-treated water ranges 4 to 6;

the pH value of the pressurized acidic pre-treated water is about 5;

the pH value of the pressurized acidic pre-treated water is about 4;

the pH value of the pre-treated ozonated liquid is below 7;

the pH value of the pre-treated ozonated liquid ranges 2 to 6.95;

the pH value of the pre-treated ozonated liquid ranges 4 to 6;

the pH value of the pre-treated ozonated liquid is about 5;

the pH value of the pre-treated ozonated liquid is about 4;

the pH value of the pre-treated ozonated water is below 7;

the pH value of the pre-treated ozonated water ranges 2 to 6.95;

the pH value of the pre-treated ozonated water ranges 4 to 6;

the pH value of the pre-treated ozonated water is about 5;

the pH value of the pre-treated ozonated water is about 4;

a temperature of the pressurized acidic pre-treated liquid is maintained approximately the same as that of the dissolution column;

a temperature of the pressurized acidic pre-treated liquid is from 10 to 30° C.;

a temperature of the pressurized acidic pre-treated liquid is from 15 to 25° C.;

a temperature of the pressurized acidic pre-treated liquid is approximately at ambient temperature;

a temperature of the pressurized acidic pre-treated liquid is about 20° C.;

a temperature of the pressurized acidic pre-treated water is maintained approximately the same as that of the dissolution column;

a temperature of the pressurized acidic pre-treated water is from 10 to 30° C.;

a temperature of the pressurized acidic pre-treated water is from 15 to 25° C.;

a temperature of the pressurized acidic pre-treated water is approximately at ambient temperature;

a temperature of the pressurized acidic pre-treated water is about 20° C.;

the pressure of the pre-treatment dissolution column is from 1 to 5 barg;

the pressure of the pre-treatment dissolution column is from 2 to 4 barg;

the pressure of the pre-treatment dissolution column is about 3 barg;

the pressure of the pre-treated ozonated liquid ranges from 1 to 5 barg;

the pressure of the pre-treated ozonated liquid ranges from 2 to 4 barg;

the pressure of the pre-treated ozonated liquid is about 3 barg;

the pressure of the pre-treated ozonated water ranges from 1 to 5 barg;

the pressure of the pre-treated ozonated water ranges from 2 to 4 barg;

the pressure of the pre-treated ozonated water is about 3 barg;

a temperature of the pre-treated ozonated liquid ranges from 10° C. to 30° C.;

a temperature of the pre-treated ozonated liquid ranges from 15° C. to 25° C.;

a temperature of the pre-treated ozonated liquid is approximately at ambient temperature;

a temperature of the pre-treated ozonated liquid is approximately 20° C.;

a temperature of the pre-treated ozonated water ranges from 10° C. to 30° C.;

a temperature of the pre-treated ozonated water ranges from 15° C. to 25° C.;

a temperature of the pre-treated ozonated water is approximately at ambient temperature;

a temperature of the pre-treated ozonated water is approximately 20° C.;

a steady state phase represents a time period during which the slope of dissolved ozone concentration vs time curve remains below 0.10 g $dO_3$/min in batch operation mode, i.e., there is no significant increase in the concentration of dissolved ozone with addition of ozone;

the steady state phase is characterized by high dissolved ozone concentration;

a start-up phase represents a time period within which the concentration of dissolved ozone gradually builds up from t=0 to the time at which the system reaches the steady state in batch operation mode;

the start-up phase is characterized by high ozone mass transfer efficiency;

a decay phase represents a time period during which decomposition of dissolved ozone to oxygen occurs without addition of ozone in batch operation mode;

a start-up mode is used in continuous operation mode and refers to conditions which exist within a body of acidic pressurized liquid during the start-up phase in batch operation mode as described above;

the start-up mode has zero to low concentration of dissolved ozone in the acidic pressurized liquid;

the start-up mode has high rate of change of dissolved ozone in the acidic pressurized liquid;

the start-up mode has high mass transfer efficiency of ozone from gas to liquid phase in the acidic pressurized liquid;

the characteristics associated with the start-up mode is present close to a headspace of the dissolution column under continuous operation mode;

the characteristics associated with the start-up mode is present in an upper portion of the body of the acidic pressurized liquid under continuous operation mode;

the start-up mode favors high efficiency of ozone mass transfer into the acidic pressurized water;

the start-up mode favors high efficiency of ozone mass transfer into the acidic pressurized liquid;

the start-up mode under continuous operation mode is characterized by high ozone mass transfer efficiency;

the characteristics associated with the start-up mode is present close to a headspace of the dissolution column under continuous operation mode;

the characteristics associated with the start-up mode is present in an upper portion of the body of the acidic pressurized water under continuous operation mode;

a steady-state mode is used in continuous operation mode that favors a high concentration of dissolved ozone in the acidic pressurized liquid;

the steady-state mode is used in continuous operation mode and refers to conditions which exist within a body of acidic pressurized liquid during the steady-state phase in batch operation mode as described above;

the steady-state mode has high concentration or saturated or close to saturated concentration of dissolved ozone in the acidic pressurized liquid;

the steady state mode has zero to low mass transfer efficiency of ozone from gas to liquid phase in the acidic pressurized liquid;

the steady-state mode favors a high concentration of dissolved ozone in the acidic pressurized water;

the steady-state mode refers to conditions which exist within a body of acidic pressurized liquid characterized by the steady-state phase in batch operation mode as described above;

the characteristics associated with the steady-state mode is present close to the bottom of the dissolution column under continuous operation mode;

the characteristics associated with the steady state mode is present close to the outlet of the dissolution column under continuous operation mode;

the characteristics associated with the steady state mode is present in a lower portion of the body of the acidic pressurized liquid under continuous operation mode;

the start-up mode and the steady state mode co-exist in the body of the acidic pressurized liquid within the dissolution column under continuous operation mode;

the start-up mode and the steady state mode coexist in the body of the acidic pressurized water within the dissolution column under continuous operation mode;

the start-up mode in an upper portion of the dissolution column that favors high efficiency of ozone mass transfer into the acidic pressurized liquid and the steady state mode in a lower portion of the dissolution column that favors a high concentration of dissolved ozone in the acidic pressurized liquid coexist within the body of the acidic pressurized liquid;

the start-up mode in an upper portion of the dissolution column that favors high efficiency of ozone mass transfer into the acidic pressurized water and the steady state mode in a lower portion of the dissolution column that favors a high concentration of dissolved ozone in the acidic pressurized water coexist within the body of the acidic pressurized water;

an ozone concentration gradient is formed in the body of the acidic pressurized liquid within the dissolution column under continuous operation mode along a height of the body of the acidic pressurized liquid;

an ozone concentration gradient is formed in the body of the acidic pressurized water within the dissolution column under continuous operation mode along a height of the body of the acidic pressurized water;

a steady state concentration of dissolved ozone in the ozone strong water is close to the saturation concentration of dissolved ozone;

a steady state concentration of dissolved ozone in the ozone strong water is greater than approximately 150 mg/L;

a steady state concentration of dissolved ozone in the ozone strong water ranges from approximately 150 mg/L to approximately 300 mg/L;

a steady state concentration of dissolved ozone in the ozone strong water is up to approximately 200 mg/L;

a steady state concentration of dissolved ozone in the ozone strong water is up to approximately 300 mg/L;

a steady state concentration of dissolved ozone in the gas-free liquid containing dissolved ozone is greater than approximately 150 mg/L;

a steady state concentration of dissolved ozone in the gas-free liquid containing dissolved ozone ranges from approximately 150 mg/L to approximately 300 mg/L;

a steady state concentration of dissolved ozone in the gas-free liquid containing dissolved ozone is up to approximately 200 mg/L;

a steady state concentration of dissolved ozone in the gas-free liquid containing dissolved ozone is up to approximately 300 mg/L;

a steady state concentration of dissolved ozone in the gas-free liquid oxidant ranges from approximately 150 mg/L to approximately 300 mg/L;

a steady state concentration of dissolved ozone in the gas-free liquid oxidant is up to approximately 200 mg/L;

a steady state concentration of dissolved ozone in the gas-free liquid oxidant is up to approximately 300 mg/L;

a steady state concentration of dissolved ozone in the gas-free liquid oxidant ranges from approximately 150 mg/L to approximately 300 mg/L;

a steady state concentration of dissolved ozone in the liquid oxidant is up to approximately 200 mg/L;

a steady state concentration of dissolved ozone in the liquid oxidant is up to approximately 300 mg/L;

a steady state concentration of dissolved ozone in the gas-free oxidant is greater than approximately 150 mg/L;

a steady state concentration of dissolved ozone in the gas-free oxidant ranges from approximately 150 mg/L to approximately 300 mg/L;

a steady state concentration of dissolved ozone in the gas-free oxidant is up to approximately 200 mg/L;

a steady state concentration of dissolved ozone in the gas-free oxidant is up to approximately 300 mg/L;

the fluid injection device is selected from a S-ring shape diffuser device or a Gap-ring shape diffuser device;

the fluid injection device is a S-ring shape diffuser device;

the fluid injection device is a Gap-ring shape diffuser device;

the fluid injection device is a diffuser device;

the diffuser device is a S-ring shaped diffuser device or a Gap-ring shaped diffuser device;

the diffuser device is a S-ring shaped diffuser device;

the diffuser device is a Gap-ring shaped diffuser device;

the S-ring shaped diffuser includes a S-shaped conduit;

each end of the S-shaped conduit is a nozzle;

the S-ring shaped diffuser includes a hollow post;

one end of the hollow post fluidly communicates with a hole at the lateral center of the S-shaped conduit and the other end of the hollow post fluidly communicates with the fluid recirculation loop;

the Gap-ring shaped diffuser device includes a bottom round plate having a through-hole in the center;

the Gap-ring shaped diffuser device includes a top round plate parallel with the bottom round plate, supported with adjustable posts between the top round plate and the bottom round plate and having a conus in the center, the conus partially inserted into the center of the through-hole of the bottom round plate;

the Gap-ring shaped diffuser device includes a hollow post fluidly communicating with the through-hole of the bottom round plate and the fluid recirculation loop;

a clearance between the top round plate and the bottom round plate ranges from approximately 2 mm to approximately 6 mm;

a clearance between the top round plate and the bottom round plate is approximately 4 mm;

the fluid recirculation loop comprises an ozone generator configured and adapted to generate ozone gas using oxygen gas so as to form an ozone and oxygen gas mixture;

the fluid recirculation loop comprises a gas venturi injector configured and adapted to inject the ozone and oxygen gas mixture into the pressurized liquid stream circulated through the diffuser device to form the gas and liquid mixture;

the fluid being recirculated by the fluid recirculation loop is a stream of the acidic pressurized liquid from the dissolution column;

the fluid being recirculated by the fluid recirculation loop is a stream of the acidic pressurized water from the dissolution column;

the fluid recirculation loop comprises a recirculation pump, fluidly communicating with the gas venturi injector, configured to elevate a pressure of the pressurized liquid stream slightly higher than the pressure in the pressure vessel, so as to ensure the gas and liquid mixture is continuously injected through the diffuser device into the dissolution column;

the water recirculation loop comprises an ozone generator configured and adapted to generate ozone gas using oxygen gas so as to form an ozone and oxygen gas mixture;

the water recirculation loop comprises a gas venturi injector configured to inject the ozone and oxygen gas mixture into the pressurized water stream circulated from the diffuser device to form the gas and water mixture;

the water recirculation loop comprises a recirculation pump, fluidly communicating with the gas venturi injector, configured to elevate a pressure of the pressurized water stream slightly higher than the pressure in the pressure vessel, so as to ensure the gas and water mixture is continuously injected into the diffuser device;

the two-phase mixture of oxygen-ozone gas and recirculated water is formed by the fluid recirculation loop fluidly connected to the diffuser device;

a pressure of the two-phase mixture of oxygen-ozone gas and recirculated water is slightly larger than that of the body of the acidic pressurized liquid;

the two-phase mixture of oxygen-ozone gas and recirculated water is formed by the water recirculation loop fluidly connected to the diffuser device;

a pressure of the two-phase mixture of oxygen-ozone gas and recirculated water is slightly larger than that of the body of the acidic pressurized water;

the recirculated liquid is a stream of the acidic pressurized liquid from the dissolution column;

the recirculated water is a stream of the acidic pressurized water from the dissolution column;

the first gas injection device is a gas injector;

the first gas injection device is a gas venturi injector;

the first gas injection device is a gas diffuser;

the first gas injection device includes a gas venturi nozzle configured to inject the acidification agent into the pressurized feed liquid stream;

the first gas injection device includes a gas venturi nozzle configured to inject the acidification agent into the pressurized feed water stream;

the first gas injection device includes a pump configured and adapted to produce the pressurized feed liquid stream;

the first gas injection device includes a pump configured and adapted to produce the pressurized feed water stream;

the first gas injection device is fluidly connected to the liquid inlet in the proximate of the headspace of the dissolution column in a single stage dissolution system;

the first gas injection device is fluidly connected to the liquid inlet in the proximate of the headspace of the main dissolution column in a two-stage dissolution system;

the first gas injection device is fluidly connected to a liquid inlet in the proximate of the headspace of the pre-treatment dissolution column in a two-stage dissolution system;

the first gas injection device is fluidly connected to a liquid inlet in the bottom of the main dissolution column in a two-stage dissolution system;

the second gas injection device is a gas injector;

the second gas injection device is a gas venturi injector;

the second gas injection device is a gas diffuser;

a controller is configured and adapted to adjust a flow rate of the acidic pressurized feed water stream fed to the inlet of dissolution column so as to yield an inflow of the acidic pressurized feed water stream that enables to continuously produce the ozone strong water;

a controller is configured and adapted to adjust a flow rate of the acidic pressurized feed liquid stream fed to the inlet of dissolution column so as to yield an inflow of the acidic pressurized feed liquid stream that enables to continuously produce the gas-free liquid containing dissolved ozone;

a controller is configured and adapted to adjust a flow rate of the acidic pressurized feed liquid stream fed to the inlet of dissolution column so as to yield an inflow of the acidic pressurized feed liquid stream that enables to continuously produce the gas-free oxidant;

a plurality of injection nozzles, each fluidly connected to the outlet of the dissolution column, are configured and adapted to adjust a flow rate of the produced gas-free liquid containing dissolved ozone discharged from the outlet of the dissolution tank to match the flow rate of the acidic pressurized feed liquid stream fed to the inlet of the dissolution column;

a plurality of injection nozzles, each fluidly connected to the outlet of the dissolution column, are configured and adapted to adjust a flow rate of the produced ozone strong water discharged from the outlet of the dissolution tank to match the flow rate of the acidic pressurized feed water stream fed to the inlet of the dissolution column;

a plurality of injection nozzles, each fluidly connected to the outlet of the dissolution column, are configured and adapted to adjust a flow rate of the produced gas-free oxidant discharged from the outlet of the dissolution column to match the flow rate of the acidic pressurized feed liquid stream fed to the inlet of the dissolution column;

a ratio of height/diameter of the body of the acidic pressurized liquid in the pressure vessel is larger than 5:1;

a ratio of height/diameter of the body of the acidic pressurized liquid in the pressure vessel is preferably from 5:1 to 20:1;

a ratio of height/diameter of the body of the acidic pressurized liquid in the pressure vessel is preferably from 5:1 to 10:1;

a ratio of height/diameter of the body of the acidic pressurized water in the pressure vessel is larger than 5:1;

a ratio of height/diameter of the body of the acidic pressurized water in the pressure vessel is preferably from 5:1 to 20:1;

a ratio of height/diameter of the body of the acidic pressurized water in the pressure vessel is preferably from 5:1 to 10:1;

a residence time of the acidic pressurized liquid in the dissolution column ranges from approximately 5 mins to approximately 150 mins;

a residence time of the acidic pressurized liquid in the dissolution column ranges from approximately 5 mins to approximately 120 mins;

a residence time of the acidic pressurized liquid in the dissolution column ranges from approximately 5 mins to approximately 100 mins;

a residence time of the acidic pressurized water in the dissolution column ranges from approximately 5 mins to approximately 150 mins;

a residence time of the acidic pressurized water in the dissolution column ranges from approximately 5 mins to approximately 120 mins;

a residence time of the acidic pressurized water in the dissolution column ranges from approximately 5 mins to approximately 100 mins;

a residence time of ozone in the acidic pressurized liquid in the dissolution column varies depending on the height of the body of the acidic pressurized liquid, pressure in the headspace and the diffuser selection in the dissolution column;

a residence time of ozone in the acidic pressurized water in the dissolution column varies depending on the height of the body of the acidic pressurized water, pressure in the headspace and the diffuser selection in the dissolution column;

the oxidant gas is an oxidizing substance;

the oxidant gas is an oxygen-containing gas;

the oxidant gas is ozone; and the oxidant gas is oxygen, $NO_2$, $N_2O$, or the like;

a first gas injection device configured and adapted to inject an acidification agent into a pressurized feed liquid stream to maintain a pH value of the pressurized feed water stream below 7;

a dissolution column comprises:

(i) a pressure vessel, configured and adapted to contain a body of acidic pressurized liquid and an off gas in a headspace above the body of the acidic pressurized liquid;

(ii) an inlet, configured and adapted to permit passage of the pressurized feed liquid stream, after the injection of the acidification agent, into the pressure vessel through the headspace;

(iii) an off-gas vent, configured and adapted to release the off gas contained in the headspace of the pressure vessel so as to maintain a pressure of the pressure vessel within a pre-determined pressure range; and (iv) an outlet, configured and adapted to discharge the gas-free liquid containing ozone from the pressure vessel;

a fluid recirculation loop has a fluid inlet, fluidly connected to the dissolution column, configured and adapted to receive a fluid from the dissolution column; a second gas injection device, configured and adapted to inject ozone into the fluid being recirculated by the fluid recirculation loop; and a fluid injection device, within the pressure vessel, mounted on the bottom of the pressure vessel, configured and adapted to diffuse the fluid, after the injection of ozone, into the body of the acidic pressurized liquid in the pressure vessel, thereby injecting ozone therein;

a controller, configured and adapted to adjust a flow rate of the acidic pressurized feed liquid stream fed to the inlet of dissolution column so as to yield an inflow of the acidic pressurized feed liquid stream that enables to continuously produce the gas-free liquid containing ozone;

at least one injection nozzles each controlled by a valve, fluidly connected to the outlet of the dissolution column, configured and adapted to adjust a flow rate of the produced gas-free liquid containing ozone discharged from the outlet of the dissolution column to match the flow rate of the acidic pressurized feed liquid stream fed to the inlet of the dissolution column so as to maintain a start-up mode in an upper portion of the pressure vessel that favors a high efficiency of ozone mass transfer into the acidic pressurized liquid and a steady-state mode in a lower portion of the pressure vessel that favors a high dissolved ozone concentration in the acidic pressurized liquid coexistent in the body of the acidic pressurized liquid in the pressure vessel, wherein a concentration gradient of dissolved ozone is formed along a height of the body of the acidic pressurized liquid;

the liquid recirculation loop further comprises an ozone generator configured to generate ozone gas using oxygen gas, and a recirculation pump, fluidly communicating with the fluid inlet and the second gas venture injector, configured to elevate a pressure of the fluid slightly higher than the pressure in the pressure vessel, so as to ensure the fluid after the injection of ozone is diffused into the body of the acidic pressurized liquid in the pressure vessel through the fluid injection device;

a pre-treatment dissolution column comprises (i) a pre-treatment pressure vessel, configured and adapted to contain a body of the acidic pressurized pre-treatment liquid and a pre-treatment off gas in a pre-treatment headspace above the body of the acidic pressurized pre-treatment liquid; (ii) a pre-treatment inlet, configured and adapted to permit passage of the pressurized feed liquid stream after the injection of the acidification agent, into the pre-treatment pressure vessel through the pre-treatment headspace; (iii) a gas inlet in the bottom of the pre-treatment dissolution column, configured and adapted to inject the gas stream released from the pressure vessel into the body of the acidic pressurized pre-treatment liquid in the pre-treatment pressure vessel to produce a pre-treated ozonated liquid therein; (iv) a pre-treatment off-gas vent, configured to release the pre-treatment off gas in the pre-treatment headspace so as to maintain a pressure of the pre-determined pressure vessel with a pre-determined pressure range lower than the pressure of the pressure vessel; and (v) a pre-treatment outlet, configured and adapted to discharge the pre-treated ozonated liquid out of the pre-treatment pressure vessel;

a fluid pump, configured and adapted to pump the pre-treated ozonated liquid into the pressure vessel through the inlet of the dissolution column;

a method for continuous production of ozone strong water, the method comprising the steps of a) injecting an acidification agent into a pressurized feed water stream to maintain a pH value of the pressurized feed water stream below 7, b) feeding the pressurized feed water stream, after injection of the acidification agent, into a dissolution column to form a body of acidic pressurized water therein, c) diffusing a two-phase mixture of oxygen-ozone gas and recirculated water into the body of acidic pressurized water in the dissolution column to dissolve ozone into the acidic pressurized water, thereby producing the ozone strong water therein; d) maintaining a pressure of the dissolution column within a pre-determined pressure range by a controlled release of an off-gas stream from the dissolution column, e) discharging the ozone strong water from the dissolution column; and f) adjusting a flow rate of the ozone strong water discharged from the dissolution column to match a flow rate of the pressurized feed water stream fed into the dissolution column after the injection of the acidification agent, so as to simultaneously maintain a start-up mode in an upper portion of the dissolution column that favors high efficiency of ozone mass transfer into the acidic pressurized water and a steady-state in a lower portion of the dissolution column that favors a high concentration of dissolved ozone in the acidic pressurized water coexistent in the body of the acidic pressurized water in the pressure vessel, wherein a concentration gradient of dissolved ozone is formed along a height of the body of the acidic pressurized water;

a method for continuous production of a gas-free liquid containing dissolved ozone, the method comprising the steps of i) injecting an acidification agent into a pressurized feed liquid stream to maintain a pH value of the pressurized feed liquid stream below 7, ii) feeding the pressurized feed liquid stream, after injection of the acidification agent, into a dissolution column to form a body of acidic pressurized liquid therein, iii) diffusing a two-phase mixture of oxygen-ozone gas and recirculated liquid into the body of acidic pressurized liquid in the dissolution column to dissolve ozone into the acidic pressurized liquid, thereby producing the gas-free liquid containing dissolved ozone, iv) maintaining a pressure of the dissolution column within a pre-determined pressure range by a controlled release of an off-gas stream that contains ozone from the dissolution column, v) discharging the gas-free liquid containing dissolved ozone from the dissolution column, and vi) adjusting a flow rate of the liquid containing dissolved ozone discharged from the dissolution column to match a flow rate of the pressurized feed liquid stream fed to the dissolution column after injection of the acidification agent, so as to simultaneously maintain a start-up mode in an upper portion of the dissolution column that favors high efficiency of ozone mass transfer into the acidic pressurized water and a steady state mode in a lower portion of the dissolution column that favors a high dissolved ozone concentration in the acidic pressurized liquid coexistent in the body of the acidic pressurized water in the pressure vessel, wherein a concentration gradient of dissolved ozone is formed along a height of the body of the acidic pressurized liquid;

a method for continuous production of a gas-free oxidant for liquid oxidation processes, the method comprising the steps of 1) injecting an acidification agent into a pressurized feed liquid stream to maintain a pH value of the pressurized feed water stream below 7. 2) feeding the pressurized feed liquid stream, after injection of the acidification agent, into a dissolution column to form a body of acidic pressurized liquid therein, 3) dissolving an oxidant gas into the body of the acidic pressurized liquid to produce the gas-free oxidant, 4) maintaining a pressure of the dissolution column within a pre-determined pressure range by a controlled release of an off-gas stream from the dissolution column, 5) discharging the gas-free oxidant from the dissolution column, and 6) adjusting a flow rate of the gas-free oxidant discharged from the dissolution column to match a flow rate of the pressurized feed liquid stream fed to the dissolution column after injection of the acidification agent, so as to simultaneously maintain a start-up mode in an upper portion of the dissolution column that favors high efficiency of ozone mass transfer into the acidic pressurized liquid and a steady state mode in a lower portion of the dissolution column that favors a high dissolved ozone concentration in the acidic pressurized liquid coexistent in the body of the acidic pressurized water in the pressure vessel, wherein a concentration gradient of dissolved ozone is formed along a height of the body of the acidic pressurized liquid.

Notation and Nomenclature

The following detailed description and claims utilize a number of abbreviations, symbols, and terms, which are generally well known in the art, and include:

As used herein, the indefinite article "a" or "an" in the text or in a claim should generally be construed to mean "one or more" unless specified otherwise or clear from context to be directed to a singular form.

As used herein, "about" or "around" or "approximately" in the text or in a claim means±15% of the value stated.

As used herein, "close to" or "nearly" in the text or in a claim means within 10% of the term stated. For example, "close to saturated concentration" refers to within 10% saturated concentration.

As used herein, the term "ozone mass transfer" is intended to refer to ozone transferred from gaseous phase to water across a gas-liquid interface.

The terms "ozone dissolution" refers to ozone gas dissolving into water, which is an alternative term of ozone mass transfer herein.

The term "pressurized liquid" or "pressurized water" refers to any possible scenario in which a pressure gauge when inserted into a line or vessel containing a body of liquid gives a pressure reading higher than ambient pressure. The term "pressurized liquid" or "pressurized water" has been used to describe two sets of conditions. In the first one, when the "pressurized liquid" is taken out of a column or vessel, it means that a headspace of the column or vessel in contact with a continuous liquid phase is at an elevated pressure. Secondly, when the "pressurized liquid" is fed into a column, it refers to a discharge head at which the liquid is pumped.

The term "ozone strong water" refers to a pressurized gas-free high concentrated or saturated or close to saturated (e.g. within 10% of saturation concentration, such as 5% or 1% or 0.1%) dissolved ozone water which is supersaturated if at atmospheric pressure. One of the applications of the ozone strong water is used as liquid oxidant.

The term "feed liquid" refers to a liquid composed primarily of water, such as fresh water, tap water, process liquid, effluent water, municipal and industrial wastewater, wastewater already treated by the secondary treatment process, or the like, or composed of aqueous solutions, organic solvents, or the like.

The term "feed water" refers to a liquid composed primarily of water, such as fresh water, tap water, process liquid, effluent water, municipal and industrial wastewater, wastewater already treated by the secondary treatment process, etc.

The term "process liquid" refers to a liquid composed primarily of water, such as fresh water, tap water, process liquid, effluent water, municipal and industrial wastewater, wastewater already treated by the secondary treatment process, aqueous solutions, organic solvents, or the like.

The term "process water" refers to a liquid composed primarily of water, such as fresh water, tap water, process liquid, effluent water, municipal and industrial wastewater, wastewater already treated by the secondary treatment process, etc.

The term "oxidized liquid" refers to a process liquid whose non-water constituents have been oxidized partially or completely with an oxidant. Alternatively, the term "oxidized liquid" refers to a produced liquid having components that have been oxidized in a process liquid by ozone strong water. Alternatively, the term "oxidized liquid" refers in particular cases to a liquid emerging out from an oxidation process, in which various organic and inorganic constituents present in the process liquid have been converted into an oxidized form due to the action of a suitable oxidant.

The term "ozonation" refers to a water treatment process that destroys microorganisms and degrades organic and inorganic pollutants using ozone as the oxidant. Ozonation is a chemical water treatment technique based on the infusion of ozone into water. Ozonation is a type of advanced oxidation process, involving the production of very reactive oxygen species able to attack a wide range of organic and inorganic compounds and all microorganisms.

The term "ozonated water" refers to a product of ozone bubbling through water that contains levels of dissolved ozone in the water.

The term "ozone dosage" is defined as the amount of ozone in gas phase of an ozone-oxygen gas mixture fed to the water (gram/minute). The ozone dosage is the mathematical product of the ozone concentration in the ozone-oxygen gas mixture ($g/m^3$) and a feed gas flow rate of the ozone-oxygen gas mixture ($m^3/hr$).

The term "supersaturated" refers to a liquid dissolution of gas which is not stable at atmospheric conditions and would degas.

The term "homogeneous" refers to a mixture of the fluids with a mixing quality >approximately 95%. Here the mixing quality is a measure of the homogeneity or uniformity of a mixture and is calculated from statistic basic variables. The coefficient of variation is the most commonly used measure. The closer this value approximates 0 the more uniform the mixture. For visualization, it is subtracted from 1 and specified in %. Thus, 100% mixing quality (or coefficient of variation=0) refers to the best mixing condition, which, however, is practically not achievable. A mixing quality>95% is described as technically homogeneous.

The term "gas-free" refers to a liquid without visible individual bubbles and/or without detectable turbidity caused by microbubbles. For example, the ozone strong water is gas-free as the ozone from feed-gas is completely dissolved into water to generate a dissolved ozone water. The ozone-strong water is hence a single liquid phase and is gas-free as the dissolved ozone concentration is less than the saturation concentration for operating conditions.

The term "steady state phase" refers to a time period during which a slope of dissolved ozone concentration vs time curve remains below $0.10\ g\ dO_3/min$ in batch operation mode, i.e., there is no significant increase in the concentration of dissolved ozone with addition of ozone.

The term "start-up phase" refers to a time period within which the concentration of dissolved ozone gradually builds up from t=0 to the time at which the system reaches the steady state in batch operation mode.

The term "decay phase" refers to a time period during which decomposition of dissolved ozone to oxygen occurs without addition of ozone in batch operation mode.

The term "start-up mode" is a terminology used in continuous operation mode of the disclosed methods and systems. The term "start-up mode" refers to conditions which exist within a body of acidic pressurized liquid during the start-up phase in batch operation mode as described above. These conditions include, but are not limited to, zero to low concentration of dissolved ozone in the acidic pressurized liquid, a high rate of change of dissolved ozone in the acidic pressurized liquid with time and a high rate of ozone mass transfer from gas phase to liquid phase.

The term "steady state mode" is a terminology used in continuous operation mode of the disclosed methods and systems. The term "steady-state mode" refers to conditions which exist within a body of acidic pressurized liquid during the steady state phase in batch operation mode as described above. These conditions include, but are not limited to, a high concentration of dissolved ozone in the acidic pressurized liquid, a low rate of change of dissolved ozone in acidic pressurized liquid with time and a low rate of ozone mass transfer from gas phase to liquid phase.

The term "steady state condition" refers to a condition in which dissolution system properties remain approximately the same over time. These properties include, but are not limited to, concentration of dissolved ozone, concentration of ozone in the off-gas, pH of liquid, etc. When the dissolution system attains "steady state condition" in a continuous operation mode, a body of the liquid may have different concentrations of dissolved ozone along the height of the body of the liquid. However, these concentration values would remain approximately constant with addition of ozone over time.

The term "high ozone mass transfer efficiency" refers to a transfer efficiency of ozone from gas phase to liquid phase of approximately 60% or more, during a residence time period of feed-gas within a body of acidic pressurized liquid in dissolution systems.

The term "high ozone concentration" or "high concentration of dissolved ozone" refers to a dissolved ozone concentration value which is saturated or close to saturated (e.g. within 10% of saturation concentration, such as 5% or 1% or 0.1%) dissolved ozone liquid.

Reference herein to "one embodiment" or "an embodiment" means that a particular feature, structure, or characteristic described in connection with the embodiment may be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Ranges may be expressed herein as from about one particular value, and/or to about another particular value. When such a range is expressed, it is to be understood that another embodiment is from the one particular value and/or to the other particular value, along with all combinations within said range.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein:

FIG. 1b is an example of running the decoupling system shown in FIG. 1a;

FIG. 3a is a block diagram of a S-ring diffuser;

FIG. 3b is a block diagram of a Gap-ring diffuser;

FIG. 3c is a block diagram of a cylindrical fluid feeder as the diffuser;

FIG. 5a is a block diagram of an exemplary two-stage ozone dissolution system;

FIG. 13 is a comparison of batch operation data to a multiple continuous operation results, the former with system shown in FIG. 2b and the latter with system as shown in FIG. 2a;

FIG. 14 is a comparison of mass transfer efficiency obtained after the system has attained a steady state condition for various liquid flow rates through a dissolution column in continuous operation mode with the system shown in FIG. 2a;

FIG. 16 is a plot of an ozone concentration gradient as a function of height of the dissolution column after the system has attained a steady state condition with various flow rates, in continuous operation mode with the system shown in FIG. 2a; and FIG. 17 is a block diagram of a common ozone dissolution column system designed to have all three processes of dissolution (mass transfer) and reaction in a single reactor.

DESCRIPTION OF PREFERRED EMBODIMENTS

Figure 1A:
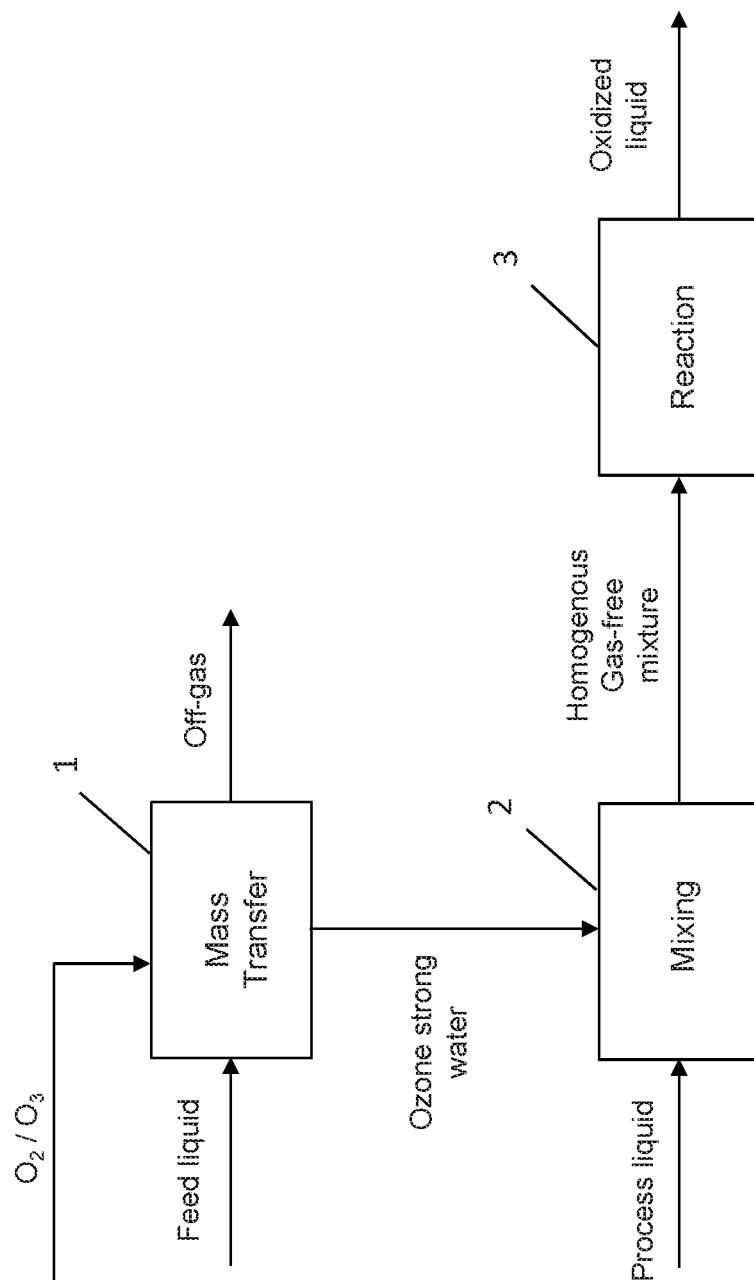
FIG. 1a is a block diagram of a decoupling system for separation of ozone oxidation process in liquid media into three unit operations for process optimization.

Disclosed are methods and systems for dissolving ozone gas in a desired liquid medium, such as in water. An objective of the disclosed methods and systems is to increase concentration of dissolved ozone (dO$_3$) in the desired liquid medium and/or to increase a rate of ozone mass transfer for use as a liquid oxidant for liquid oxidation processes, such as, providing disinfection applications and micropollutant removal from wastewater.

In the disclosed methods and systems, a sufficiently high concentration of dissolved ozone (e.g., up to approximately 300 mg/L) in aqueous fluid may be achieved by diffusing into a body of acidic pressurized liquid, a fluid having a two-phase mixture of O$_2$/O$_3$ gas and recirculated liquid phase. To this end, the body of acidic pressurized liquid is preferably prepared with a pH value less than 7 at a constant elevated pressure and a constant temperature in a dissolution column; the fluid having the dissolved ozone therein is prepared with an optimized gaseous ozone dosage (e.g., approximately 1.6 g O$_3$ per minute); and a diffuser is specifically designed for optimized mass transfer from gas to liquid phase. A fluid recirculation loop includes a venturi-nozzle incorporated into a downstream line of a recirculation pump that generates desired pressure drop as a result of the liquid flow through a contracting cross-section of the venturi-nozzle, thereby enabling a steady injection of the O$_2$/O$_3$ gas mixture into the pressurized liquid in the fluid recirculation loop. The ozone mass transfer in the body of acidic pressurized liquid is enhanced by use of suitable diffusers (e.g., Gap-ring or S-ring diffusers herein, described in detail below.) mounted within the dissolution column at the bottom. Selections and designs of the diffusers determine the dynamics of ozone mass transfer and gas-bubble diameters as gas bubbles rise up in the dissolution column as well as the gas flow patterns generated within the dissolution column. Accordingly, the mass transfer of ozone from gas phase to the body of acidic pressurized liquid having a high concentration of dissolved ozone in liquid is achieved with the disclosed methods and systems. The high concentration of dissolved ozone in liquid at elevated pressures may correspond to saturation or close to saturation concentration of dissolved ozone in liquid. When the pressure drops, the concentration of the dissolved ozone in liquid may be supersaturated. Note that, if the liquid medium is water, the high concentration of dissolved ozone in water achieved may be defined as an ozone strong water hereinafter. The term "ozone strong water" refers to a pressurized gas-free high concentrated or saturated or close to saturated (e.g. within 10% of saturation concentration, such as 5% or 1% or 0.1%) dissolved ozone water which is supersaturated if at atmospheric pressure. One of the applications of the ozone strong water is its use as a liquid oxidant. The disclosed methods and systems would enable generation of the ozone strong water.

The disclosed systems are a mass transfer unit or a dissolution system or a dissolution column included in a decoupled system that separates an ozone based oxidation process in liquid media into three unit operations for process optimization. In many processes of using ozone for a liquid oxidation process, the treatment involves simultaneous ozone dissolution, mixing (if any) and reaction performed in a single reaction unit or a single column (e.g., as shown in FIG. 17). The disclosed mass transfer unit 1 is separated from a mixing unit and a reaction unit. As shown in FIG. 1a, there is shown an embodiment of the decoupled system including a mass transfer unit 1 generating a liquid oxidant, for example, ozone strong water, a mixing unit 2 which injects the liquid oxidant into the process liquid flow at specific injection patterns to produce a homogeneous and gas-free mixture of the liquid oxidant and the process liquid, and a reaction unit 3 where a liquid oxidation process occurs by using the homogeneous and gas-free mixture of the liquid oxidant and the process liquid, so that the process liquid is converted into an oxidized liquid. Typically, the ozone mass transfer process in the mass transfer unit 1 takes place approximately several minutes, for example, approximately 20 min; mixing ozone strong water with process liquid in the mixing unit 2 occurs less than several seconds, for example, less than approximately 2 seconds; and reaction process happens from a few milliseconds to several minutes, for example, to approximately 5 min. The mixture of ozone strong water and process liquid forms a liquid oxidant in the mixing unit 2, which is gas-free because the liquid oxidant is produced at an elevated pressure which is not supersaturated. The mixing unit 2 comprises of multiple specially designed injection nozzles and a static mixer, the unit designed for creating a homogenous mixture of the liquid oxidant and the process liquid with a mixing quality >95%.

The mixture of the liquid oxidant and the process liquid produced by mixing unit 2 is also gas-free because no visible gas bubbles are observed and/or no turbidity caused by microbubbles is detected.

The mass transfer unit 1 is described herein in detail. The rate of ozone mass transfer is enhanced when the gas dissolution is performed at elevated pressures in the dissolution column (i.e., an elevated pressure is maintained in headspace of the dissolution column). Thus, having a separate step for ozone dissolution or ozone mass transfer followed by i) mixing of the gas-free liquid oxidant (e.g., ozone strong water) with the process liquid and ii) followed then by a separate reaction/oxidation step disclosed herein leads to process flexibility and enables a treatment system to operate the treatment process under optimized economical and performance condition. This process has the advantages of potential reduction in operating costs and required capital investments required for ozone-based treatment systems.

The disclosed mass transfer systems include apparatus that may further comprise a pre-treatment dissolution column that allows recovery of undissolved ozone gas in an off-gas stream liberated from a high-pressure dissolution column. In this case, the gas-to-liquid mass transfer of ozone is achieved through a two-step dissolution process minimizing the loss of ozone through the vented off-gas compared to a single step dissolution using a single dissolution column.

There is therefore an optimum way of dissolving ozone in water to achieve the ozone strong water, which relies on multiple operating parameters, such as pH value of water, pressure levels in the dissolution column, temperature of water, ozone dosage, diffuser designs and number of ozone dissolution stages. The disclosed methods and apparatus with optimized pH, pressure, temperature, diffuser, etc. may increase the concentration of dissolved ozone in water to greater than approximately 150 mg/L, preferably up to approximately 200 mg/L, more preferably up to approximately 300 mg/L.

Figure 2A:
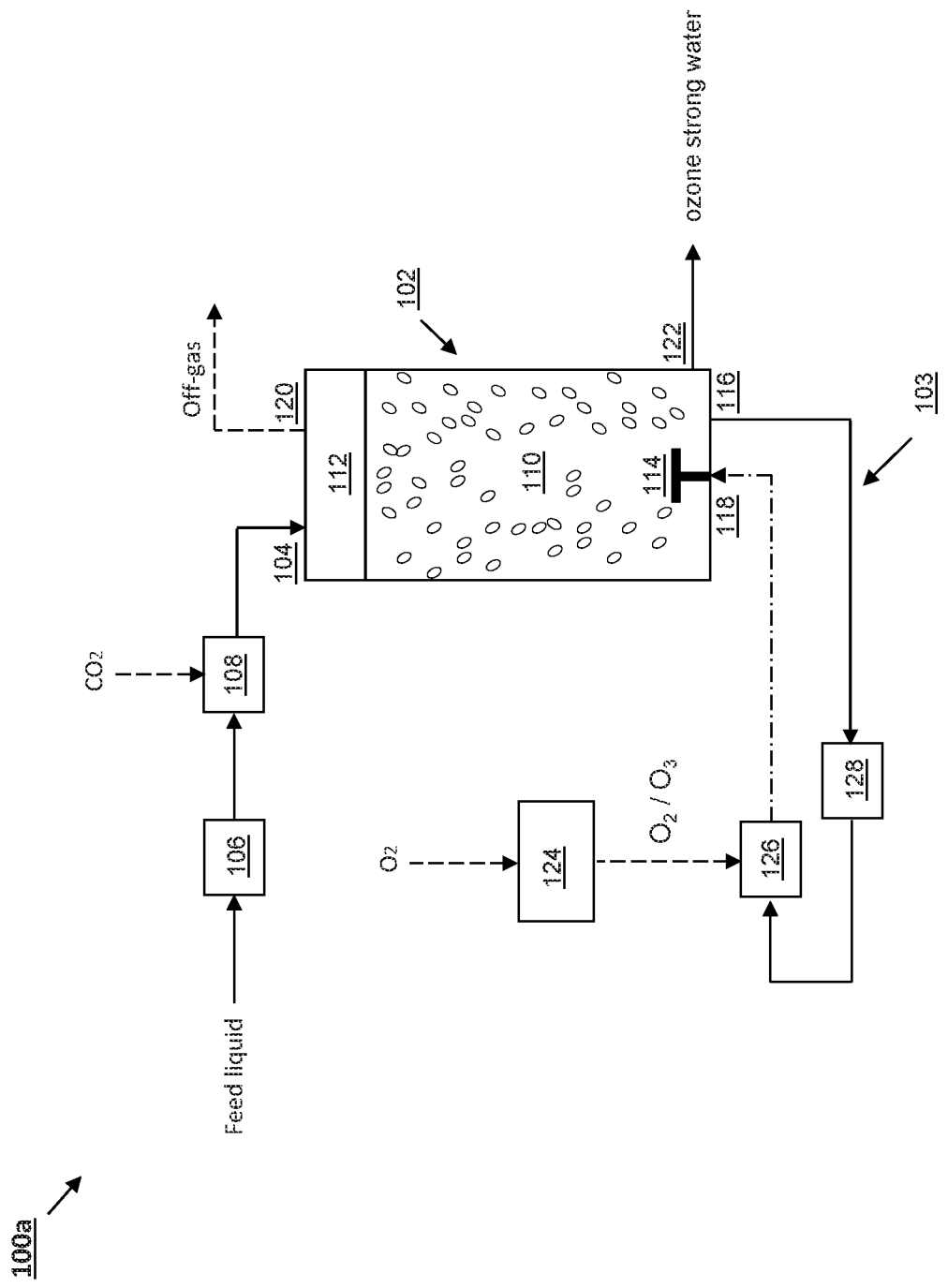
FIG. 2a is a block diagram of an exemplary single-stage ozone dissolution system operated in continuous operation.

As best illustrated in FIG. 2a, a preferred embodiment of the disclosed gas dissolution or mass transfer system is an illustrated ozone strong water system 100a for continuously producing the ozone strong water that comprises a dissolution column 102 and a fluid recirculation loop 103 in fluid communication with the dissolution column 102. System 100a further includes liquid lines denoted as solid lines, gas lines denoted as dashed lines, gas-liquid mixture line denoted as a dash dotted line and gas bubbles denoted as elliptical dots.

Figure 1B:
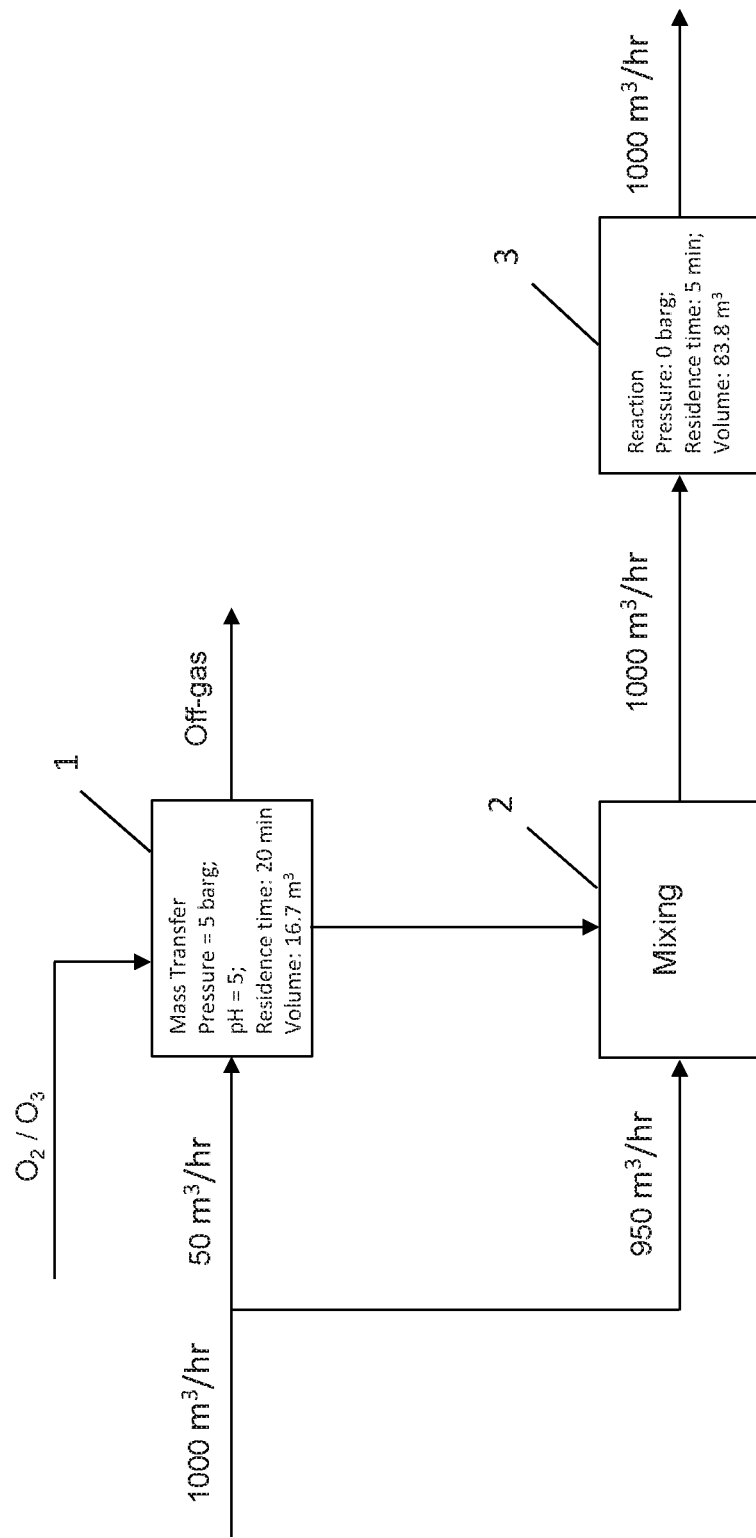

Dissolution column 102 may be a stainless steel vessel or an ozone dissolution chamber/tank or a pressure vessel, which has a pressure rating suitable for the operation and may be maintained at constant temperature levels using cooling coils incorporated into it (not shown). Dissolution column 102 may be in a cylindrical shape having a sidewall and a top cover and a bottom cover. In comparison with the current ozonation technology available which involves a single tank/column to perform mass transfer and reaction process under atmosphere pressure (shown in FIG. 17), dissolution column 102 may be 10 to 20 times smaller than the single tank/column of the current ozonation procedure to achieve ozonation of water. For example, ozonation of 1000 $m^3$/hr of water in a single tank system with 20 min residence time requires a tank volume of 333 $m^3$ at atmosphere pressure for the entire oxidation process including dissolution and reaction processes. In comparison, as shown in FIG. 1b, with a flow rate of 50 $m^3$/hr of feed liquid into mass transfer unit 1, a residence time of 20 minutes, a pressure of 5 barg and a pH 5, an approximately 200 mg/L of ozone strong water is achieved with a tank volume of 16.7 $m^3$ of mass transfer unit 1, which is around 1/20 compared to the tank volume of 333 $m^3$. The produced ozone strong water is then mixed with 950 $m^3$/hr of process liquid in mixing unit 2 and the mixture is forwarded to reaction unit 3. With a residence time of 5 min under 1 bar, a tank volume of 83.3 $m^3$ is required for a flow rate of 1000 $m^3$/hr of oxidized liquid. Total volume requirement of the disclosed decoupled mass transfer system is 16.7 $m^3$+83.3 $m^3$=100 $m^3$, which is much smaller than the tank volume of 333 $m^3$ of the single tank system.

Dissolution column 102 may be a liquid treating tank which is closed except for fluid handling inlets and/or outlets. Here all fluid handling inlets and/or outlets are accompanied with valves (not shown) that may be controlled with suitable instrumentation. Dissolution column 102 comprises liquid inlet 104 that permits passage of feed liquid into the dissolution column through action of pump 106. The liquid inlet 104 may be a cylindrical pipe. Pump 106 is a high pressure liquid pump provided for injecting the feed liquid into the dissolution column under pressure. To ensure proper tank pressure and uniform level of water in dissolution column 102 during entire period of operation, fluid flow into the dissolution column from the high pressure pump 106 is controlled via feedback from sensors indicating water levels within dissolution column 102.

The feed liquid may be composed of water, such as fresh water, tap water, process water, effluent water, municipal and industrial wastewater, wastewater already treated by the secondary treatment process, or the like. The feed liquid may also be composed of aqueous solutions, organic solvents, or the like. In one embodiment, the feed liquid is pressurized by pump 106 and then passes through a $CO_2$ gas injector 108 where $CO_2$ gas is injected into the pressurized feed liquid to achieve an acidic pH of the pressurized feed liquid. This was experimentally confirmed to suppress the formation of OH free radicals in water by the dissociation of dissolved ozone thereby increasing the concentration of the dissolved $O_3$ in water. Those skilled in the art will recognize that mineral acids, such as, HCl, $H_2SO_4$, $HNO_3$, or other acids may also be used to generate the acidic pH of the pressurized feed liquid.

Alternatively, the feed liquid may be an acidic feed liquid, such as acidic industrial wastewaters from phosphate manufacturing, mining, steel mills, or the like. If this is the case, depending on the pH of the industrial wastewater, the feed liquid is pressurized by the pump and then may be fed to dissolution column 102 directly, and $CO_2$ gas injector 108 may be skipped. If the pH of the acidic industrial wastewater needs to be adjusted, $CO_2$ gas injector 108 may not be skipped. $CO_2$ gas injector 108 may be a gas-liquid venturi nozzle that sucks $CO_2$ gas into the pressurized feed liquid stream if the available $CO_2$ gas pressure is lower than the pressure of the pressurized feed liquid stream. If the available $CO_2$ gas pressure is higher than the pressure of the pressurized feed liquid stream, here $CO_2$ gas injector 108 may be a gas injector or a ceramic gas diffuser, rather than a gas-liquid venturi nozzle.

Dissolution column 102 contains a body of acidic pressurized liquid 110 and a gas headspace 112 above the body of acidic pressurized liquid at an over pressure. A ratio of liquid volume to gas headspace volume in dissolution column 102 is maintained preferably at approximately 12:1. A ratio of liquid volume versus gas volume in gas headspace 112 may range from 1.7:1 to 12:1. Dissolution column 102 also comprises a recirculation liquid outlet 116 and a fluid feed inlet 118 in the bottom, which constitute the fluid recirculation loop 103 along with a fluid diffuser device 114, an ozone generator 124, a venturi nozzle 126 and a recirculation pump 128. Fluid diffuser device 114 may be installed within the dissolution column at the bottom center and fluidly connected to fluid feed inlet 118 formed in the bottom of the dissolution column. The recirculation liquid outlet 116 provides a small portion of the acidic pressurized water to the recirculation pump 128 and the pressure of the small portion of the acidic pressurized water is elevated larger than the pressure of the acidic pressurized water in dissolution column 102. A gas and liquid mixture of $O_2/O_3$ produced by an ozone generator 124 is then mixed with the small portion of the acidic pressurized water to form a mixture of $O_2/O_3$ gas and acidic pressurized water that has gaseous and liquid phases and has a pressure greater than the pressure of the acidic pressurized water in dissolution column 102. As a result, the mixture of $O_2/O_3$ gas and acidic pressurized water flows into dissolution column 102 at the fluid feed inlet 118 through action of fluid recirculation loop 103, where the $O_2/O_3$ gas and liquid mixture is fed into dissolution column 102 by passing through fluid diffuser device 114 that is fluidly connected to fluid feed inlet 118.

System 100a comprises an oxygen supply (not shown) which provides oxygen gas to ozone generator 124 that converts oxygen to ozone. Because of its relatively short half-life, ozone is generated on-site by an ozone generator. An ozone generator produces ozone in a mixed form of gas containing $O_2/O_3$. The concentration of ozone gas is dependent on the concentration of ozone in $O_2/O_3$ mixture and thus dependent on its partial pressure. The concentration of dissolved ozone attainable in the process is influenced by several factors, such as temperature, pressure, pH, ozone dosage, residence time of gas, diffuser type, etc. The high dissolved ozone concentration or the ozone strong water in the proposed method was a result of the optimization of multiple factors, including, but not limited to pH, diffuser type design and operational conditions. Among the factors listed, important factors influencing the dissolved ozone concentration are the pH and diffuser design.

Summarized, the concentration of dissolved ozone in dissolution column 102 may be increased by:

Decreasing the pH of water to pH <7;
Increasing operation pressure;
Decreasing water temperature;
An optimal diffuser design capable of maintaining a desirable residence time of ozone gas in water by controlling ozone bubble diameters and ozone bubble flow profile through specific diffuser devices in the dissolution column; that is, controlling the contact area and contact time between the gas phase (i.e., the ozone-oxygen gas mixture) and the liquid phase (i.e., water in the dissolution column);
Increasing ozone dosage.

The oxygen supply may be a cryogenic liquid oxygen tank or cylinder. System 100a may use a commercially available ozone generator, for example, an Ozonia CFS-2 ozone generator, capable of stable generation of ozone gas at a desirable rate, with a chiller unit for temperature control of the generator. The desirable rate of the generated ozone gas depends on the requirement of an actual application. In one embodiment, a rate of approximately 180 g/m$^3$ with a concentration of up to 12 wt % may be needed to run system 100a. The ozone is produced by feeding commercial grade oxygen into ozone generator 124. The mass transfer of ozone from the gaseous phase to water in dissolution column 102 may be achieved through a combination of venturi-nozzle based injection and suitably designed diffuser. The venturi-nozzle based injection involves venturi nozzle 126 incorporated into the downstream line of recirculation pump 128 which generates a desired pressure drop as a result of water flow through a contracting cross-section of venturi nozzle 126, thereby enabling a steady injection of the generated ozone gas (mixed with $O_2$) into a recirculated liquid stream. The ozone gas which enters into dissolution column 102 through the fluid recirculation loop 103 is dissolved in the liquid phase of dissolution column 102 by use of suitable diffusers (e.g., Gap-ring or S-ring diffuser) 114 within the dissolution column. Venturi nozzle 126 and recirculation pump 128 of the fluid recirculation loop 103 are fluidly connected to fluid feed inlet 118 and recirculation liquid outlet 116 associated with dissolution column 102. Recirculation pump 128 is a liquid pump. A small stream of the acidic pressurized water in dissolution column 102 flowing out from recirculation liquid outlet 116 is pumped to venturi nozzle 126 through action of recirculation pump 128. Once ozone is generated, a quantity of ozone-oxygen gas mixture coming out of ozone generator 124 is introduced into venturi nozzle 126. The quantity of ozone-oxygen gas mixture is then sucked into the pressurized water stream by venturi nozzle 126 forming an ozone-oxygen gas and water mixture. Thus, the ozone-oxygen gas mixture is carried by the acidic pressurized water and flows back to dissolution column 102 through fluid feed inlet 118. Recirculation pump 128 pumps the acidic pressurized water coming out of recirculation liquid outlet 116 to a pressure much higher than the pressure of dissolution column 102 in order to provide for a pressure drop of the acidic pressurized water after passing through venturi based $O_3$ gas injector 126. The pressure of the ozone-oxygen gas and water mixture flowing out of venturi nozzle 126 is reduced compared to the pressure of the water coming out of recirculation pump 128 but still higher than the pressure of dissolution column 102 allowing the ozone-oxygen gas and water mixture to flow back to the dissolution column. Fluid diffuser device 114 fluidly connected to fluid feed inlet 118 then diffuses the ozone-oxygen gas and water mixture into the acidic pressurized water in the dissolution column.

Once the fluid recirculation loop 103 is set to start, the generation of ozone in ozone generator 124 is initiated with oxygen flowing through ozone generator 124 at a desirable flow rate to generate ozone therein. The concentration and pressure of the generated $O_3/O_2$ gas mixture are adjusted to desired operating conditions and delivered to the fluid recirculation loop 103. A flow rate of the ozone-oxygen gas and water mixture fed to the fluid diffuser device 114 is adjusted by changing the power input to the recirculation pump 128. In this way, a discharge from the recirculation pump 128 may be controlled. Alternatively, using a control valve downstream of the recirculation pump 128 may also control the flow rate of the ozone-oxygen gas and water mixture fed to the fluid diffuser device 114. During the course of operation, dissolved ozone concentrations in the liquid of dissolution column 102, the pH value of the liquid in the dissolution column and temperature fluctuations of the dissolution column are continually monitored and recorded.

When the ozone-oxygen gas and water mixture flows through the fluid diffuser device 114 into the acidic pressurized water contained within dissolution column 102, gas bubbles in the recirculation stream are broken into small bubbles which then rise up in the dissolution column. The acidic pressurized water in dissolution column 102 comes into contact with the gas bubbles containing ozone, with the resulting mass transfer process yielding dissolved ozone in the acidic pressurized water, thereby producing the ozone strong water in dissolution column 102. Simultaneously, oxygen gas also rises up to headspace 112 of dissolution column 102 due to its limited solubility in water. Undissolved $O_3$ gas and undissolved $O_2$ gas are then accumulated in headspace 112 of the dissolution column forming an off-gas. The ozone strong water is thus produced in dissolution column 102. The produced ozone strong water is then passed into an external mixing unit (not shown) through fluid outlet 122 for a liquid oxidation process, where the ozone strong water may be mixed with a process liquid for oxidation of micropollutants or any similar oxidation process. More specifically, the fluid outlet 122 may be fluidly connected to a plurality of injection nozzles. The plurality of injection nozzles each may have a valve and may be adjusted to control the flow rate of the ozone strong water discharged from fluid outlet 122 of dissolution column 102 to match the flow rate of the acidic pressurized feed water stream fed to liquid inlet 104 of dissolution column 102.

The process liquid may be typically composed of water, such as fresh water, tap water, process water, effluent water, municipal and industrial wastewater, wastewater already treated by the secondary treatment process, etc. The process liquid may also be composed of aqueous solutions, organic solvents, or the like. The process liquid may include the same type of water as the feed liquid which carries components that should be oxidized. Additionally, in some cases, the feed liquid and the process liquid may be originated from the same source.

Dissolution column 102 also comprises an off-gas vent 120 in its top that allows a release of the off-gas, so as to maintain the dissolution column pressure at a desired level. The off-gas contains $O_2$, undissolved $O_3$, and undissolved $CO_2$ gas.

The pH value of the feed liquid to dissolution column 102 may be adjusted by injecting $CO_2$ gas or mineral acid, such as, HCl, $H_2SO_4$, $HNO_3$, or other acidification agent for corresponding adjustment of the pH to acidic pH. For the purpose of producing the ozone strong water, the pH value of the water in dissolution column 102 is preferably maintained below 7 by adding $CO_2$ gas (or mineral acid or other acid) into the feed liquid. This is done by installing the $CO_2$ gas injector 108 (or other acidifying chemical injector such as HCl, $H_2SO_4$, or $HNO_3$, or other mineral acid) in between pump 106 and feed liquid inlet 104 for producing the pressurized feed liquid having an acidic pH value, as described above. The amount of acidifying chemical injected into the injector 108 and the flow rate of the feed liquid may be continuously monitored and adjusted by suitable instrumentation. In order to produce a maximum mass transfer of ozone, the pH value of water in dissolution column 102 is maintained preferably in a range of 2 to slightly less than 7. For instance, the pH value of water in dissolution column 102 is maintained preferably in a range of 2 to 6.95. More preferably, the pH value of water in dissolution column 102 is maintained at approximately 3 to 6. Even more preferably, the pH value of water in dissolution column 102 is maintained at approximately 5. Even more preferably, the pH value of water in dissolution column 102 is maintained at approximately 4. One of ordinary skill in the art would recognize that the pH value may be adjusted by controlling a net flow of $CO_2$ gas, or a net flow of other acidifying chemicals, into the pressurized feed liquid through the injector 108.

The cooling coils (not shown) incorporated into dissolution column 102 may be adjusted to maintain a temperature of water in dissolution column 102 at a desired constant level for producing the ozone strong water. Preferably, the temperature of dissolution column 102 ranges from 10° C. to 30° C. More preferably, the temperature of the dissolution column ranges from 15° C. to 25° C. Even more preferably, the temperature of the dissolution column is maintained at an ambient temperature, such as approximately 20° C. to achieve a targeted operation at optimized operational costs.

In an initial course of operation, dissolution column 102 is first filled with water having an acidic pH to a desirable liquid level and then pressurized. This process may be continuously monitored and adjusted with the aid of pressure sensors. Based on the actual requirements, dissolution column 102 may be filled with varying volumes of water. A ratio of water volume versus gas volume in gas headspace 112 may range from 1.7:1 to 12:1. Once the water filled into dissolution column 102 reaches to the desirable liquid level and the temperature and pH levels of the water in the dissolution column are suitably adjusted, dissolution column 102 is then pressurized by injection of oxygen gas into the dissolution column through an oxygen gas injection inlet (not shown). The pressurization may be achieved either by injecting oxygen gas directly into the headspace of the dissolution column or through a venturi-nozzle injection into the recirculated water stream. Both pressurization methods yield identical results. Preferably, the pressure of gas headspace 112 of dissolution column 102 is maintained in a range of approximately 2 to 7 barg. More preferably, the pressure of gas headspace 112 of the dissolution column is maintained in a range of approximately 3 to 6 barg. Even more preferably, the pressure of gas headspace 112 of the dissolution column is maintained at approximately 5 barg. Correspondingly, during a continuous operation of the disclosed system, the pressure of the water feed into dissolution column 102 pumped by pump 106 may be slightly larger than the pressure of the water in dissolution column 102 in order to feed the water into the dissolution column. During the continuous operation of the disclosed mass transfer system, the pressure of gas headspace 112 of the dissolution column is also maintained in a range of approximately 2 to 7 barg. More preferably the pressure of gas headspace 112 of the dissolution column is maintained in a range of approximately 3 to 6 barg. Even more preferably, the pressure of gas headspace 112 of the dissolution column is maintained at approximately 5 barg.

For the purpose of constantly producing the ozone strong water, the disclosed mass transfer system is operated in continuous mode to continuously produce ozone strong water. Once the water in dissolution column 102 is pressurized, a continuous operation mode may be started by proceeding with the following operations simultaneously:

i) feeding the feed liquid into pump 106 to form a pressurized feed liquid;

ii) feeding $CO_2$ into $CO_2$ gas injector 108 (or other acidification chemicals) to adjust the pH value of the pressurized feed liquid to a desired level, that is, below 7;

iii) feeding oxygen into ozone generator 124 to generate ozone gas;

iv) opening ozone strong water fluid outlet 122 for discharging the ozone strong water out to an external mixing unit; and v) opening off-gas vent 120 to maintain an internal pressure of the dissolution column 102 with a pre-determined pressure range by a controlled release of an off-gas stream from the dissolution column.

The above operations may be performed simultaneously and/or in various sequences. Under continuous operation, a flow rate of the ozone strong water out of dissolution column 102 from fluid outlet 122 is adjusted to be approximately the same as that of the feed liquid flowing into the dissolution column through feed liquid inlet 106, thereby maintaining, within a defined range, constant pressure and constant volume of the liquid in dissolution column 102 under constant flow conditions. Thus, the operation of system 100a generates a continuous liquid stream of ozone strong water.

One of ordinary skill in the art will recognize that the disclosed mass transfer system may also applied to produce an ozone dissolved liquid by dissolving ozone into the pressurized acidic feed liquid. In one embodiment, the produced ozone dissolved liquid may be the ozone strong water.

One of ordinary skill in the art will also recognize that the disclosed mass transfer system may also applied to produce a liquid oxidant for liquid oxidation processes by dissolving an oxidant gas into the pressurized acidic feed liquid. The oxidant gas may be an oxygen-containing gas, such as ozone, oxygen, $NO_2$, $N_2O$, or the like.

A continuous monitoring of concentrations of the ozone feed-gas and the off-gas associated with dissolution column 102 may be required, both of which are monitored using separate gas-ozone analyzers. Furthermore, suitable instrumentation is also incorporated for the recordings of the temperature, pH of the water in the dissolution column, pressure in the dissolution column headspace, volumetric flow rate of oxygen fed into the ozone generator, and dissolved ozone levels in the dissolution column, etc. The headspace pressure in the dissolution column may be set at desired values by proper adjustment of a needle valve in the off-gas line of the dissolution column (not shown).

One of the major challenges in gas-liquid contact processes targeting a high gas absorption in the liquid phase is the design of diffusers which may generate an optimal gas bubble diameter as well as a desired residence time distribution of the gas phase within the liquid volume. A diffuser design based on the optimization of the above parameters along with an economic analysis of the related operating costs is essential for extracting an optimized performance for any given scenario of operating conditions. It is known that shear force decomposes dissolved ozone in water causing a reduction in the observed values for dissolved ozone. The disclosed mass transfer systems use a S-ring and a Gap-ring diffuser to reduce the shear force thereby limiting the decomposition of the dissolved ozone. In comparison of the S-ring and the Gap-ring, the Gap-ring produces better results.

In addition, a gas-liquid mass transfer may be achieved either by bubbling gas through the bulk liquid phase or conversely, by dispersing liquid as microbubbles or fine droplets in the bulk gas phase—both of which requires an optimal diffuser design capable of achieving desired dispersion characteristics of either gas or liquid phase. The diffuser types used herein include, but are not limited to, bulk-liquid volume based diffusers, which include a S-ring diffuser 10 and a Gap-ring diffuser 20 shown in FIG. 3a and FIG. 3b, respectively. S-ring diffuser 10 or Gap-ring diffuser 20 may be installed at the bottom of dissolution column 102 with sufficient clearance maintained from the bottom to avoid gas entrapment in the fluid recirculation loop. One of ordinary skill in the art will recognize that any types of fluid diffusers capable of generating desired dispersion characteristics of either gas or liquid phase may be used herein.

FIG. 3a is a block diagram of a S-ring diffuser used in the disclosed gas dissolution system. The top diagram is a top view of S-ring diffuser 10 and the bottom diagram is a cross-sectional view of S-ring diffuser 10 along a line A-A'. The line B-B' shows the axis of the S-ring diffuser. As shown, S-ring diffuser 10 includes a S-shape top conduit 12 having a nozzle 14 at each end toward the opposite directions for injecting the gas/water mixture into the liquid in the dissolution column. S-ring diffuser 10 also has base 18 for fixing the S-ring diffuser on the bottom of the dissolution column by thread holes 18A. The clearance between the S-shaped top conduit and the bottom is formed by spacing conduit 16 having one end fluidly connected to the bottom center of S-shape top conduit 12 and the other end fluidly connected to fluid feed inlet 118 formed in the dissolution column bottom.

FIG. 3b is a block diagram of a Gap-ring diffuser used in the disclosed gas dissolution system. As shown, Gap-ring diffuser 20 includes round top plate 22A having a conus 22C in the center and a round bottom plate 22B having a through-hole in the center. The two plates 22A and 22B are spaced with several posts 24 (only one shown) placed in between. The conus 22C is partially inserted in the through-hole of the round bottom plate 22B forming a Gap-ring. Posts 24 may be several screws passing through the two plates that make the gap adjustable. Posts 24 may have several washers in between two plates 22A and 22B in which one or more washers may be removed or added to adjust the gap spacing. The clearance between Gap-ring diffuser 20 and the bottom cover of the dissolution column is formed by conduit 26 having one end fluidly connected to the bottom center of the bottom plate 22B and the other end fluidly connected to fluid feed inlet 118 in the dissolution column bottom. Gap-ring diffuser 20 is fixed on the bottom cover with base plate 28 with thread holes 28A.

FIG. 3c shows an exemplary cylindrical fluid feeder as the diffuser. The top diagram is a top view of conduit fluid feeder 30 and the bottom diagram is a cross-sectional view of conduit fluid feeder 30 along a line A-A'. The line B-B' shows the axis of the conduit fluid feeder. As shown, conduit fluid feeder 30 includes a conduit 32. The top end of the conduit 32 is an opening 34 for injecting the gas/water mixture into the liquid in the dissolution column. The bottom end of the conduit 32 is fixed with and fluidly connected to a fluid feed inlet formed in the bottom cover of the dissolution column. The base 36 fixes the conduit fluid feeder on the bottom of the dissolution column through thread holes 38.

S-ring diffuser 10 or Gap-ring diffuser 20 is able to disperse the feed ozone gas as the bubbles, which then gradually rise to the top headspace with a characteristic directionality associated with the ascending movement of the bubbles that maintains a desired residence time. The diameter of the ozone gas bubbles emerging out of the S-ring diffuser may not be adjustable. Instead, the diameter of the ozone gas bubbles emerging out of the Gap-ring diffuser may be regulated by varying the gap spacing. Each of the diffuser types 10 and 20 has their unique gas flow patterns. For example, the gap spacing in Gap-ring diffuser 20 may vary between 2 mm, 4 mm and 6 mm by adjusting the number of washers constituting the spacing of the gap. In fact, it may be seen in the examples that follow, Gap-ring diffuser 20 with 4 mm spacing performs better than S-ring diffuser 10 in terms of the dissolved ozone ($dO_3$) concentration values obtained after a definite period of ozonation as well as the fraction of feed-gas ozone which is dissolved in the liquid phase.

Figure 2B:
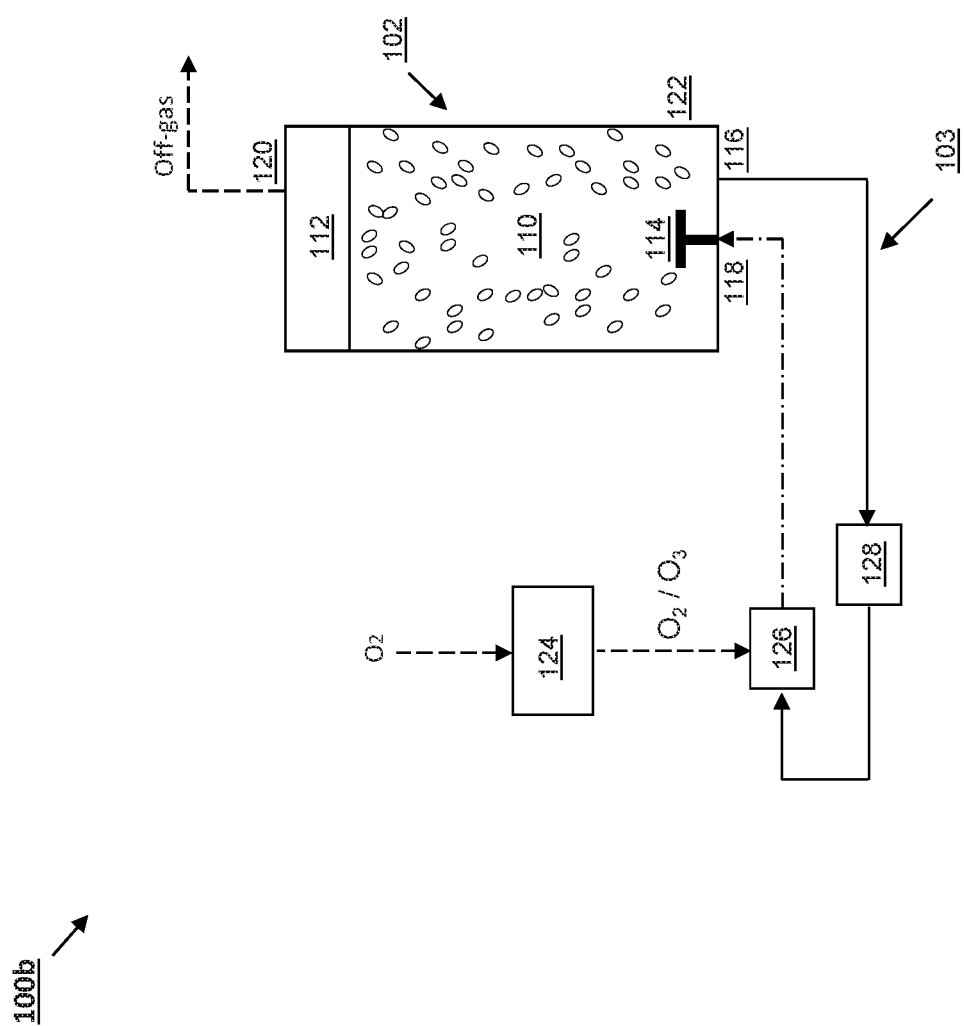
FIG. 2b is a block diagram of an exemplary single-stage ozone dissolution system operated in batch operation.

FIG. 2b is a block diagram for batch operation of the system depicted in FIG. 2a. In FIG. 2b, the same reference numerals as those in FIG. 2a denote the same or corresponding parts, which will not be further described. In batch operation, the dissolution column is initially filled with water, pH adjusted to 5, headspace pressure increased to 5 barg, followed by continuous injection of the ozone and oxygen gas mixture into the dissolution column using the venturi-nozzle 126 in the fluid recirculation loop 103. In fact, the dissolved ozone level or the dissolved ozone concentration in dissolution column 102 is built up over the ozonation time and, after a certain period of time, the dissolved ozone concentration attains a steady state characterized by negligible increase in the dissolved ozone concentration with further the ozone and oxygen gas mixture injection. Under the steady state, further ozonation of water does not result in any increase in dissolved ozone level, but a slight decrease is observed due to decomposition of dissolved ozone to oxygen. It may be seen in FIG. 4, the evolution profile of dissolved ozone concentration in water over time (i.e., residence time), produced with the system shown in FIG. 2b at 3 barg, operated in batch mode, in which the dashed line denotes the theoretical value of saturation concentration of dissolved ozone for the specified operating conditions. The evolution profile includes two distinct regimes having a start-up phase and a steady state phase. An additional decay phase was also investigated during which there was no injection of fresh ozone into liquid. The objective of investigating the additional decay is to evaluate the decomposition of dissolved ozone to oxygen during the ozonation process.

Figure 4:
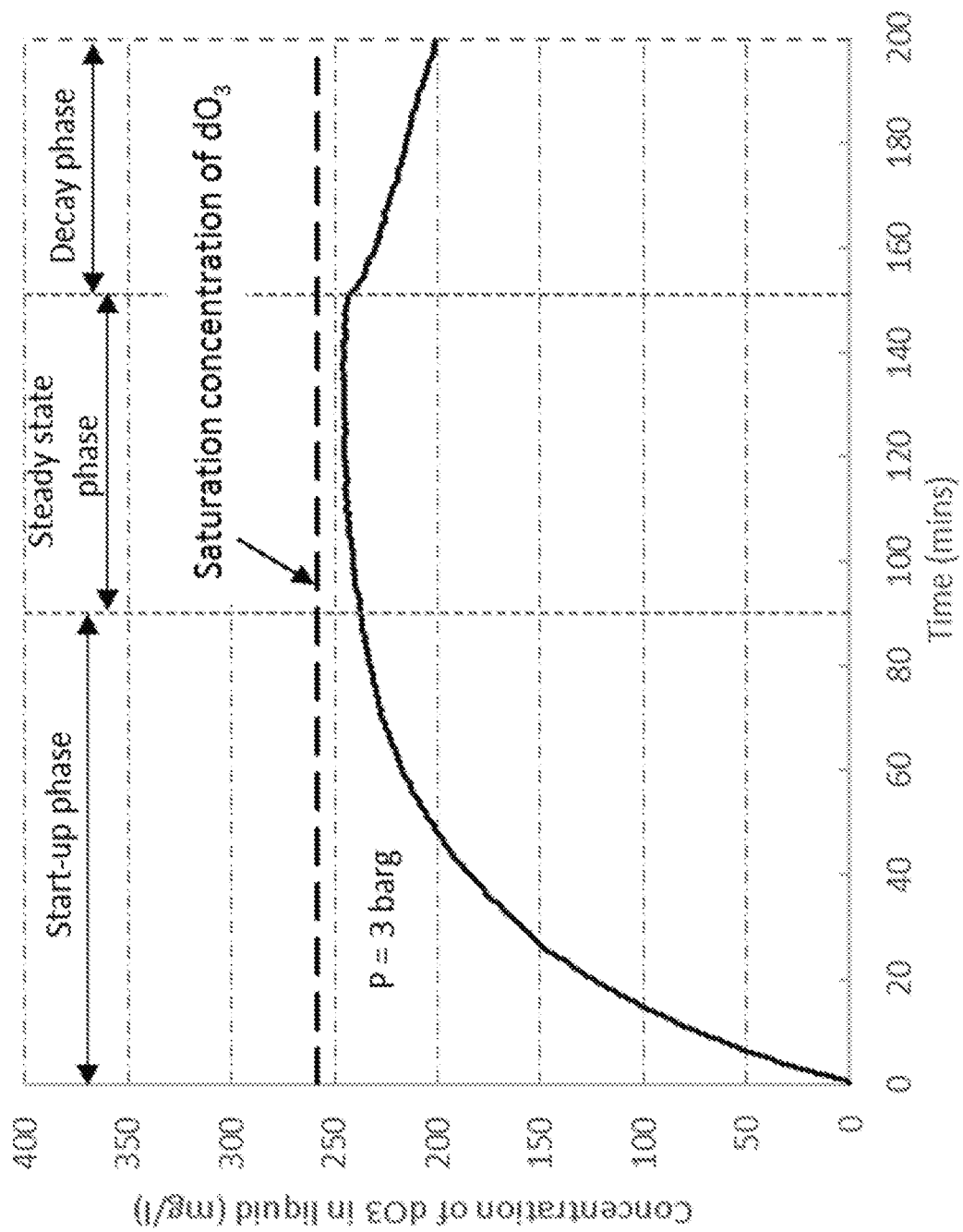
FIG. 4 is an exemplary evolution profile of dissolved ozone concentration in water over time produced with the system shown in FIG. 2b at pressure=3 barg, operated in batch mode with respect to liquid flow.

As illustrated in FIG. 4, a typical dissolved ozone concentration profile obtained at pressure 3 barg, temperature 20° C., pH 5 during a batch experimental ozonation of tap water with a single-stage ozone dissolution column shown in FIG. 2b is illustrated. The figure represents three distinct regimes over time: i) the start-up phase representing $dO_3$ concentration built-up from t=0 to the time at which the system reaches the steady state; ii) the steady state phase that characterizes the system behavior after it reaches the steady state; and iii) the decay phase that explores decomposition of dissolved ozone to oxygen without injection of fresh ozone into liquid during the bench mode operation. The total duration of this experiment performed at pressure 3 barg, temperature 20° C., pH 5, was approximately 3 hours. Alternatively, such dissolved ozone concentration profile may also be obtained at pressure of 5 barg, temperature 20° C., pH 5. The concentration of the dissolve ozone at 5 barg is higher than the concentration of the dissolve ozone at 3 barg as described below in the Examples that follow.

More specifically, once the system parameters, such as, water volume and pH value of water, temperature, pressure of the dissolution column etc., are adjusted to the desired levels, a steady flow of ozone gas is introduced into the dissolution column until the dissolution column reaches the steady state. This time regime is referred to as the 'start-up phase' in FIG. 4, and is characterized by a gradual reduction in the rate at which dissolved ozone concentration increases in the liquid phase. The rate of $dO_3$ increase is highest at the start of ozonation (at t=0), gradually reduces with further ozonation and finally becomes close to zero when the system reaches steady state. This is referred to as the slope of the curve with the units of g $dO_3$/min. The time at which this slope drops below 0.10 g $dO_3$/min is defined as the initiation of the 'steady state phase'. In the steady state phase, a relatively unchanged concentration of dissolved ozone (i.e., steady state concentration) is achieved which is little less than the saturation concentration of dissolved ozone (or equilibrium concentration) or close to the saturation concentration of dissolved ozone, as shown in FIG. 4. The steady state concentration of dissolved ozone may be the maximum concentration in the system at a specific set of operating conditions as shown in FIG. 2b. The operation of the system is allowed to continue further in the steady state regime for approximately 60 minutes, after which the ozone feed-gas to the system is terminated. The batch operation then progresses into the 'decay phase'. The objective of the decay phase is to analyze a decay constant of the system, which refers to the decomposition rate of dissolved ozone to oxygen for the given system configuration. In order to mimic an actual continuous operation mode, the decay-phase experiment requires a pressure and temperature conditions comparable in magnitude to the start-up phase, and was achieved by plugging the gas outflow from the dissolution column and utilizing temperature control coils.

Batch mode operations show ozone dissolution favors a condition of low pH, low temperature, and high pressure. At pressure=3 barg and pH=5 and temperature=20° C., approximately 250 mg/L dissolved ozone concentration may be achieved as shown in FIG. 4. At pressure=5 barg and pH=5 and temperature=20° C., approximately 300 mg/L dissolved ozone concentration may be achieved as seen below in the examples that follow (e.g., FIG. 10). Thus, the optimized operating conditions for generating ozone strong water may be as follows: pressure is approximately 5 barg, pH is approximately 5, temperature is approximately 20° C., with a 4 mm Gap-ring diffuser.

When the system is operated to generate the ozone strong water continuously, the residence time of the feed water in the dissolution column needs to be chosen, which may refer to an operational point, according to the ozone concentration profiles shown in batch operation mode (e.g., FIG. 4, FIG. 10 or FIG. 11) so as to operate the system within the start-up phase or the steady state phase. The advantage of such an operational point selection is that the rate of mass transfer of ozone from gas phase to liquid phase is high in the start-up phase. In comparison, under the steady state phase, the concentration of dissolved ozone is close to the saturation concentration of dissolved ozone, as a result, ozone in the feed-gas may not be further dissolved, thereby resulting in a waste of the feed-gas ozone. In particular, for a specific set of operating conditions (i.e., temperature, pH, pressure, ozone dosage, residence time, type of diffuser, etc.), the dissolved ozone concentration obtained from the dissolution column depends on the operational point chosen within the start-up phase or steady state phase which in turn determines the residence time of feed water in the dissolution column. The higher the residence time of feed water is in the dissolution column, the higher the dissolved ozone concentration would be, however, the efficiency of feed gas ozone usage or gas-to-liquid mass transfer rate would be lowered for such a scenario.

For example, in FIG. 4, a continuous feed water flow rate of 10 liters per minute, corresponding to a residence time of about 23 minutes for a dissolution column volume of 230 liters, would yield a concentration of approximately 140 mg/L of the dissolved ozone out of the dissolution column at the conditions of pressure=3 barg, temperature=20° C., pH=5. This operational point is associated with a high efficiency of ozone mass transfer and very little ozone waste. In comparison, a feed water flow rate of 3 liters per minute, corresponding to a residence time of about 77 minutes for a dissolution column volume of 230 liters, would yield a dissolved ozone concentration of approximately 230 mg/L at 3 barg, temperature 20° C., pH 5. This operational point is, however, associated with lower feed ozone utilization efficiency or lower mass transfer efficiency due to its proximity to the steady state. To this point, the disclosed methods and systems may be used for specific applications, such as, specific dissolved ozone concentration and specific feed gas ozone usage or mass transfer efficiency. Thus, the operational point for the disclosed systems may be chosen based on specific applications, each mode associated with their characteristic dissolved ozone concentration and feed gas ozone usage or mass transfer efficiency. Thus, the concentration of the produced ozone dissolved water or liquid varies depending on the operating modes that may be beneficial in different applications. Here, the operational point refers to the specific selection of the residence time at which the system is operated within the start-up phase or steady state phase.

In real-life operations for continuous production of the ozone strong water, the system may be operated such that a start-up mode which favors high mass transfer rate and a steady state mode which favors high dissolved ozone concentration may coexist within the body of acidic pressurized water in the dissolution column. This occurs due to a concentration gradient of dissolved ozone formed along the height of the acidic pressurized water contained within the dissolution column, in which the concentration of dissolved ozone is about zero at the top of the body of acidic pressurized water contained within dissolution column (e.g., the point of fresh feed water addition) and the highest concentration of dissolved ozone is observed at the bottom of the dissolution column (e.g., the point of ozone strong water removal). Here, the start-up mode is a terminology used in continuous operation mode of the disclosed methods and systems and refers to conditions which exist within a body of acidic pressurized liquid during the start-up phase as described in batch operation mode; the steady state mode is a terminology used in continuous operation mode of the disclosed methods and systems and refers to conditions which exist within a body of acidic pressurized liquid during the steady state phase as described in batch operation mode. Hence, the continuous operation of the disclosed systems results in simultaneously maintaining conditions in an upper portion of the dissolution column that favor high efficiency of ozone mass transfer into the acidic pressurized water and conditions in a lower portion of the dissolution column that favor a high concentration of dissolved ozone in the acidic pressurized water in which an ozone concentration gradient is formed along the height of the body of the acidic pressurized water. That is, the continuous operation of the disclosed systems results in the start-up mode favoring high gas-to-liquid mass transfer efficiency of ozone and the steady state mode favoring high dissolved ozone concentration coexist within the body of acidic pressurized water, and the concentration gradient of dissolved ozone formed along the height of the body of acidic pressurized water in the dissolution column.

In batch mode operations as described below in the examples that follow, the dissolved ozone concentration is uniform throughout the body of acidic pressurized water in the dissolution column at any instant of time during the process of ozonation. In contrast, in the continuous mode operation, referring to FIG. 15, a concentration gradient of the dissolved ozone water may be acquired along the height of the body of acidic pressurized water in a dissolution column. More specifically, an acidic pressurized fresh water continuously feeds into the dissolution column from an inlet on the top of the dissolution column through the head space of the dissolution column, forming a body of the acidic pressurized water in the dissolution column. At the same time, a gas and liquid mixture containing ozone produced by a fluid recirculation loop (not shown) is continuously diffused into the body of the acidic pressurized water in the dissolution column through a diffuser device installed on the bottom of the dissolution column within the dissolution column, producing ozone dissolved water or ozone strong water in the dissolution column. In addition, at the same time, the ozone strong water produced in the dissolution column is discharged from an outlet of the dissolution column to a target mixing unit (not shown). The continuous addition of the acidic pressurized fresh water into the dissolution column from its top and the continuous removal of the produced ozone strong water from the dissolution column bottom result in a development of the dissolved ozone concentration gradient along the height of the dissolution column or the height of the body of acidic pressurized water in the dissolution column. In this case, the conditions present in the start-up mode (i.e., high ozone mass transfer rate and low concentration of the dissolved ozone water) is formed at the top portion of the body of the acidic pressurized water in the dissolution column and the conditions present in the steady state mode (i.e., high concentration of the dissolved ozone water and low ozone mass transfer rate) is formed at the bottom portion of the body of the acidic pressurized water in the dissolution column. Thus, the start-up mode and the steady state mode coexist in the body of the acidic pressurized water in the dissolution column, which is equivalent to operating on the batch operation mode at the start-up phase to have high ozone mass transfer rate but obtaining the ozone strong water having high dissolved ozone concentration (e.g., close to saturated concentration) at the steady state phase.

The concentration gradient of dissolved ozone in the body of the acidic pressurized water in the dissolution column may be measured by taking multiple sampling points (e.g., $C_1$-$C_6$ in FIG. 15) along the height of the dissolution column. The dissolved ozone concentration at each sampling point is measured after the dissolved ozone water has attained a steady state within the dissolution column. The concentration gradient of dissolved ozone along the height of the dissolution column depends on various factors including an inflow rate of the feed liquid. In this case, the concentration gradient of dissolved ozone along the height of the dissolution column depends on the flowrate of acidic pressurized water and a ratio of height/diameter of the body of the acidic pressurized water in the dissolution column. The inflow rate of the feed liquid may be controlled by a level probe coupled with a PID controller. The outflow rate of the produced ozone strong water is adjusted to be approximately the same as the inflow rate of the feed liquid. The outflow rate of the produced ozone strong water may be manually adjusted by a plurality of injection nozzles each coupled with a flow adjustment valve. The injection nozzles may be partially included in a target mixing unit for passing the produced ozone strong water into the target mixing unit, e.g., the mixing unit 2 shown in FIG. 1a, where the ozone strong water is mixed with a process liquid to produce a homogeneous and gas-free liquid oxidant mixture of the ozone strong water and the process liquid for a liquid oxidation process. The ratio of the height/diameter of the body of the acidic pressurized water in the dissolution column may be larger than 5:1, preferably from 5:1 to 20:1, more preferably from 5:1 to 10:1.

It may be seen from the examples that follow, given enough height of the body of the acidic pressurized water in the dissolution column, in the continuous operation mode, with a desirable flow rate of the feed liquid, the concentration of the ozone strong water at the outlet of the dissolution column in continuous operation may reach to the similar concentration of the ozone strong water in batch mode operation. The desirable flow rate of the feed liquid may ensure a desirable residence time of acidic pressurized water in the dissolution column through which ozone gas is bubbled. In the disclosed methods and systems, the desirable residence time of the acidic pressurized water ranges from approximately 5 minutes to approximately 150 minutes, preferably from approximately 5 minutes to approximately 120 minutes, more preferably, from approximately 5 minutes to approximately 100 minutes. Furthermore, the residence time of ozone in the acidic pressurized water in the dissolution column varies depending on the height of the body of the acidic pressurized water, pressure in the headspace and the diffuser selection in the dissolution column. In addition, in the continuous operation mode, the ozone mass transfer rate increases linearly with increasing inflow rate of the feed liquid under the steady state. For example, the ozone mass transfer rate may reach 80% with 5.7 gpm of the feed liquid from the examples that follow (e.g., referring to FIG. 14). This results in an enhanced dissolution of the generated ozone gas into the body of acidic pressurized water in the dissolution column.

The disclosed systems for the generation of ozone strong water may also include a two-stage ozone dissolution system, as illustrated in FIG. 5a. Ozone strong water system 200a, which comprises a pre-treatment dissolution column 230 in fluid communication with main dissolution column 202, improves utilization efficiency of ozone gas. Pre-treatment dissolution column 230 allows recovery of undissolved ozone gas from the main dissolution column. System 200a further includes liquid lines denoted as solid lines, gas lines denoted as dashed lines, gas-liquid mixture line denoted as a dash dotted line and gas bubbles denoted as elliptical dots. The major difference between system 100a and system 200a relates to pre-treatment dissolution column 230 added in system 200a, where ozone contained in off-gas vented out from main dissolution column 202 is injected to pre-treatment dissolution column 230 and dissolved therein. The ozone which gets dissolved in water contained within pre-treatment dissolution column 230 forms a pre-treated ozonated water that may then be fed into main dissolution column 202 as a feed liquid for the main dissolution column to further produce a highly concentrated ozonated water, that is, ozone strong water. In this way, generation of the ozone strong water in system 200a involves a two-stage ozone dissolution process. In the first ozone dissolution stage, ozone gas generated from ozone generator 222 is introduced into main dissolution column 202 to produce the ozone strong water and the off-gas in the headspace 206 that contains undissolved ozone, as described in FIG. 2a. In the second ozone dissolution stage, the off-gas stream containing undissolved ozone from main dissolution column 202 is utilized by pre-treatment dissolution column 230 to produce pre-treated ozonated water, which has a lower dissolved ozone concentration than the ozone strong water produced by the main dissolution column and may be used as the feed liquid which is pumped into the main dissolution column. In this stage, any residual or undissolved ozone from the off-gas stream of the main dissolution column is captured and utilized and the off-gas from pre-treatment dissolution column 230 may only contain oxygen. The ozone depleted oxygen off-gas from the pre-treatment dissolution column 230 may be used in a separate process, for example, a secondary wastewater treatment process using oxygen gas. Such a two-stage ozone dissolution process is characterized by a countercurrent of the off-gas stream from main dissolution column 202 with respect to that of the water in pre-treatment dissolution column 230.

More specifically, main dissolution column 202 and pre-treatment dissolution column 230 are the same type of tanks or reactors as the one used in system 100a or system 100b. Main dissolution column 202 is basically the same as dissolution column 102 illustrated in FIG. 2a and FIG. 2b. Main dissolution column 202 contains a body of liquid 204 that is pressurized and maintained at a pH value below 7 and gas headspace 206 that contains undissolved ozone gas forming an off-gas stream. Diffuser device 208 is installed in main dissolution column 202 for injecting ozone feed gas. Here diffuser device 208 may be a S-ring diffuser as shown in FIG. 3a or a Gap-ring diffuser as shown in FIG. 3b. Diffuser device 208 may be installed at the inside center of the dissolution column bottom fluidly connected to fluid feed inlet 212 formed in the bottom of the main dissolution column. Off-gas vent 214 is formed in the top of the main dissolution column for releasing the off-gas stream in the gas headspace to the pre-treatment dissolution column 230. Ozone strong water outlet 216 is formed in the lower portion of main dissolution column 202 for passing the ozone strong water to a mixing unit (not shown) for mixing the ozone strong water into a body of a process liquid for producing an oxidized liquid through a liquid oxidation process therein. Herein, the process liquid is typically composed water, such as fresh water, tap water, process water, effluent water, municipal and industrial wastewater, wastewater already treated by the secondary treatment process, aqueous solutions, organic solvents, etc., which carries components that should be oxidized. Recirculation liquid outlet 210 is formed in the bottom cover of main dissolution column 202 for delivering a small portion of pressurized water from the main dissolution column to a fluid recirculation loop 203 that will be described below. Feed liquid inlet 218 is formed in the top portion of the main dissolution column for injecting feed liquid into main dissolution column 202. Herein the feed liquid is the pre-treated ozonated water produced in pre-treatment dissolution column 230.

No diffuser device is required to be installed in the pre-treatment dissolution column 230. Instead, gas inlet 232 is formed in the bottom of pre-treatment dissolution column 230 for injecting the off-gas from the main dissolution column into the pre-treatment dissolution column. The gas inlet 232 may be a ceramic fine bubble diffuser in any shapes, such as a cylindrical shape, a disk shape, or the like. Pre-treatment dissolution column 230 also contains a body of liquid 234 that is pressurized and maintained at a pH value below 7 and gas headspace 236 that contains a pre-treatment off-gas containing little (e.g., approximately 0.5% ozone) to no undissolved ozone. Gas inlet 232 may be formed in the bottom center of the pre-treatment dissolution column. Gas inlet 232 may be formed in any other place of the bottom of the pre-treatment dissolution column as long as the off-gas from the dissolution column 202 can be efficiently injected into the pre-treatment dissolution column. Pre-treated ozonated water outlet 238 is formed in the lower portion of the pre-treatment dissolution column 230 for feeding the pre-treated ozonated water produced in the pre-treatment dissolution column to main dissolution column 202 for further dissolution by action of pump 220.

Feed liquid inlet 240 is formed in the top of pre-treatment dissolution column 230 for injecting feed liquid into the pre-treatment dissolution column by action of pump 244. The feed liquid herein may be composed of water, such as fresh water, tap water, process water, effluent water, municipal and industrial wastewater, wastewater already treated by the secondary treatment process, or the like. The feed liquid may be composed of aqueous solutions, organic solvents, or the like. The feed liquid may also be an acidic feed liquid, such as acidic industrial wastewaters from phosphate manufacturing, mining, steel mills, or the like. Additionally, in some cases, the feed liquid and the process liquid may be from the same source. The feed liquid is pressurized by pump 244 and then the pressurized feed liquid is forwarded into a $CO_2$ gas injector 242, where $CO_2$ is dissolved in the pressurized feed liquid or pressurized water forming an acidic pH water along with high pressure and therefore increase the dissolved ozone concentration in water and suppress free radical formation. Here those skilled in the art will recognize that $CO_2$ gas may be replaced with a suitable mineral acid, such as, HCl, $H_2SO_4$, $HNO_3$, that is injected into the feed liquid to form the acidic pH water. However, $CO_2$ gas is the preferred acidification chemical. $CO_2$ gas injector 242 may be a regular gas injector or a gas-liquid venturi nozzle that sucks $CO_2$ gas into the pressurized feed liquid stream. For the purpose of producing the ozone strong water here, the pH value of the water in the pre-treatment dissolution column 230 and the main dissolution column 202 is preferably maintained below 7 by adding $CO_2$ gas into the feed liquid. The amount of $CO_2$ injected into the $CO_2$ gas injector and the flow rate of the feed liquid may be continuously monitored and adjusted by suitable instrumentation. In one embodiment, the pH value of the water in the pre-treatment dissolution column 230 is maintained the same as that of the main dissolution column 202. In this case, preferably, the pH value of the water in both two dissolution columns is maintained in a range of 2 to slightly less than 7. For example, the pH value of the water in both two dissolution columns is maintained in a range of 2 to 6.95. More preferably, the pH value of the water in the two dissolution columns is maintained in a range of 3 to 6. Even more preferably, the pH value of the water in the two dissolution columns is maintained at approximately 4 to 5. Even more preferably, the pH value of the water in the two dissolution columns is maintained at approximately 5. Even more preferably, the pH value of the water in the two dissolution columns is maintained at approximately 4. These pH ranges enable to produce a maximum concentration of dissolved ozone in water.

Off-gas vent 246 is formed in the top cover of pre-treatment dissolution column 230 for releasing the pre-treatment off-gas that primarily contains oxygen and little (e.g., approximately 0.5% ozone) to no ozone from the pre-treatment dissolution column because almost all ozone may be dissolved in water in this stage. By venting out the pre-treatment off-gas from gas headspace 236, the pressure of the gas headspace is maintained at a desirable level. Since the pre-treatment off-gas stream released from the pre-treatment dissolution column primarily contains oxygen, the pre-treatment off-gas stream may be sent to a secondary wastewater treatment process for efficiently utilizing oxygen gas. Preferably, the pressure of gas headspace 236 in pre-treatment dissolution column 230 is maintained lower than the pressure of gas headspace 206 in main dissolution column 202 for injecting the off-gas from main dissolution column 202 to pre-treatment dissolution column 230. The pre-treated ozonated water produced in pre-treatment dissolution column 230 has a dissolved ozone concentration lower than the ozone strong water produced in main dissolution column 202. This is because the concentration of ozone in the feed gas stream to pre-treatment dissolution column 230 is significant lower than the concentration of ozone in the feed gas to main dissolution column 202. The fluid recirculation loop 203 includes ozone generator 222, $O_3$ gas venturi injector 224, recirculation pump 226, fluid feed inlet 212, recirculation liquid outlet 210 and diffuser device 208 associated with main dissolution column 202. The components and the operation of the fluid recirculation loop are the same as those of the fluid recirculation loop 103 illustrated in FIGS. 2a and 2b.

When system 200a is under operation, the pre-treatment dissolution column 230 and main dissolution column 202 are first filled with feed liquid or water by action of pumps 244 and 220 through feed liquid inlet 240 and 218, respectively, up to desired levels which may be continuously monitored and adjusted with the aid of hydrostatic pressure based level meters. Simultaneously, $CO_2$ gas is fed into the $CO_2$ gas injector 242 to adjust the pH of the pressurized feed liquid to the one below 7. Based on the actual requirements, pre-treatment dissolution column 230 and main dissolution column 202 may be filled with varying volumes of water. Gas headspaces 236 and 206 are formed in the pre-treatment dissolution column and the main dissolution column, respectively, after filling the desire levels of the water. A ratio of liquid volume versus gas volume in the two dissolution columns may range from 1.7:1 to 12:1.

Cooling coils incorporated into the two dissolution columns may be utilized to adjust and maintain the temperature of the water at the desired levels after filling the water into the two dissolution columns. Preferably, the temperature of the water in the two dissolution columns ranges from 10° C. to 30° C. More preferably, the temperature of the water in the two dissolution columns ranges from 15° C. to 25° C. Even more preferably, the temperature of the water in the two dissolution columns is at ambient temperature, such as approximately 20° C.

Once the temperature and pH levels of the water in the two dissolution columns are suitably adjusted, the two dissolution columns are respectively pressurized by injection of oxygen gas into the two dissolution columns through an oxygen gas inlet (not shown) in each dissolution column. The pressurization may be achieved by injecting oxygen gas directly into headspaces of the two dissolution columns. The pressure levels were maintained at desired value during the operation by a control of the gas out-flow rates through off-gas vents in both dissolution columns 204 and 234. In one embodiment, the pressure in pre-treatment dissolution column 230 is lower than the pressure in main dissolution column 202. In this case, the pressure of the headspace 236 of pre-treatment dissolution column 230 is preferably maintained approximately from 1 to 5 barg; more preferably, the pressure of the headspace 236 of pre-treatment dissolution column 230 is maintained approximately from 2 to 4 barg; even more preferably, the pressure of the headspace 236 of pre-treatment dissolution column 230 is maintained at approximately 3 barg. Correspondingly, the pressure of the headspace 206 of main dissolution column 202 is preferably maintained approximately from 2 to 7 barg; more preferably, the pressure of the headspace 206 of main dissolution column 202 is maintained approximately from 3 to 6 barg; even more preferably, the pressure of the headspace 206 of main dissolution column 202 is maintained at approximately 5 barg.

Once the water in the two dissolution columns is pressurized, a continuous operation may be started with proceeding the following operations simultaneously:

i) feeding the pressurized feed liquid into pre-treatment dissolution column 230;

ii) feeding $CO_2$ into $CO_2$ gas injector 242 to adjust the pH value of the feed liquid;

iii) feeding oxygen into ozone generator 222 to generate ozone gas;

iv) opening dissolved ozone water outlet 238 for feeding the pre-treated ozonated water into main dissolution column 202;

v) opening ozone strong water fluid outlet 216 for discharging the ozone strong water out to an external mixing unit; and vi) opening off-gas vents 214 and 246 for releasing the off-gas stream and the pre-treatment off-gas stream to maintain internal pressures of the main dissolution column and the pre-treatment dissolution column with pre-determined pressure ranges, respectively.

Thus, system 200a continuously produces the ozone strong water. As the pressure in the pre-treatment dissolution column is lower than the pressure in the main dissolution column, pump 220 fluidly connected to dissolved ozone water outlet 238 in the pre-treatment dissolution column and fluid inlet 218 in the main dissolution column is installed to pump the pre-treated ozonated water from the pre-treatment dissolution column 230 into the main dissolution column 202.

A continuous monitoring of the feed-gas and off-gas concentrations associated with the pre-treatment dissolution column and the main dissolution column is required, both of which are monitored using separate gas ozone analyzers. Furthermore, suitable electronic control or computer-control instrumentation is also incorporated for the recording of the temperature, pH value, pressure and dissolved ozone levels in the two dissolution columns, each of which requires periodic monitoring and control for optimal operation of the two dissolution columns.

Once ozone generation in $O_3$ generator 222 is initiated and the fluid recirculation loop is started, with oxygen flowing through ozone generator 222 in a desirable flow rate, the generated ozone concentration and pressure levels delivered to the fluid recirculation loop are adjusted to desired operating conditions. During the course of operation, dissolved ozone concentrations in the water, the pH value of the water and temperature fluctuations of main dissolution column 202 and pre-treatment dissolution column 230 are continually monitored and tabulated. In fact, it may be seen from the Examples that follow, the dissolved ozone concentration in main dissolution column 202 is build up over time and, after a certain period of time, the dissolved ozone concentration attains a steady characterized by negligible increase in the dissolved ozone levels with ozone gas injection.

Here, in order to maintain a constant height of water in the two dissolution columns, an in flowrate of the feed liquid at feed liquid inlet 240 is maintained approximately the same as the out flowrate of ozone strong water through the liquid outlet 216. In addition, the pressure of the feed liquid should be maintained slightly higher than the pressure of the pre-treatment dissolution column for smoothly feeding the feed liquid into the pre-treatment dissolution column. Similarly, in the fluid recirculation loop 203, pump 226 pumps the pressurized water coming out of recirculation liquid outlet 210 to a pressure much higher than the pressure of main dissolution column 202. This provides for a pressure drop for the operation of the venturi injector 224. The liquid emerging out is fed back into main dissolution column 204 through the liquid inlet 212. Furthermore, as described above, since gas headspace 206 has a higher pressure than gas headspace 236, the off-gas stream from off-gas vent 214 may be directly injected into gas inlet 232. In the end, as described below in the examples that follow, with the two-stage ozone dissolution system, the dissolved ozone mass transfer efficiency may reach approximately 85% (e.g., refereeing to FIG. 6b). This greatly utilizes the generated ozone gas.

The disclosed gas dissolution systems and methods include multiple embodiments of injecting an acidification agent, such as $CO_2$ or a mineral acid, into the feed water for attaining acidic feed water. FIG. 5a represents one embodiment in which the acidification agent is injected into the pressurized feed water in the pre-treatment column utilizing the injector 242. For example, regarding $CO_2$ injection, the injection of $CO_2$ acidification agent occurs after the pump 244. In this embodiment, the pressure of the pre-treatment dissolution column 230 is lower than the pressure of the main dissolution column 202. For example, the pressure of the pre-treatment dissolution column 230 may be 3 barg and the pressure of the main dissolution column 202 may be 5 barg. Thus, the pressurized feed water, after injection of $CO_2$, is injected to the pre-treatment dissolution column 230 at 3 barg. The advantage of this embodiment is that both the pre-treatment column (230) and the main column (202) have a body of acidic pressurized water at similar pH which maximizes ozone dissolution in water.

Figure 5B:
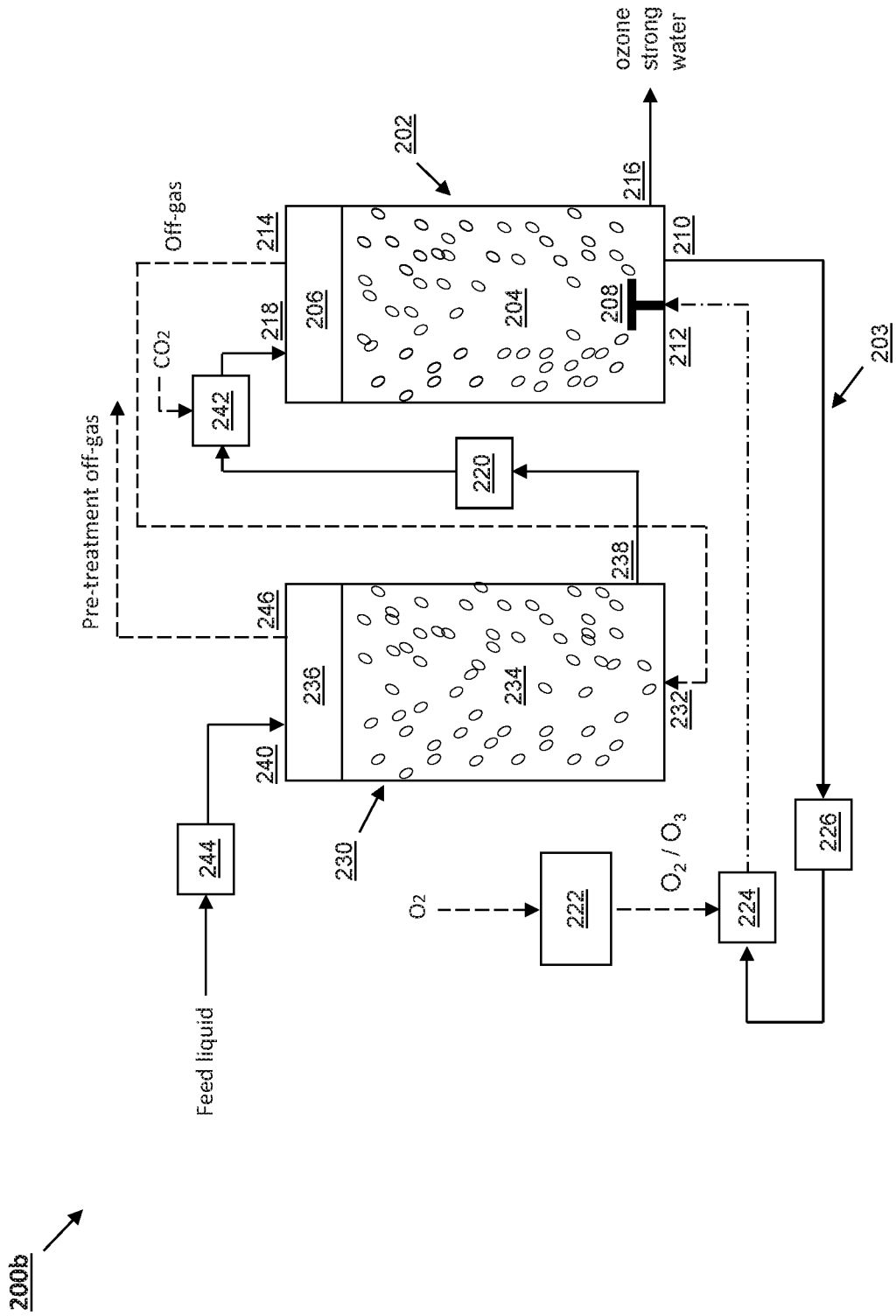
FIG. 5b is a block diagram of another exemplary two-stage ozone dissolution system.

Another embodiment for $CO_2$ or mineral acid injection in system 200b, is shown in FIG. 5b. In FIG. 5b, the same reference numerals as those in FIG. 5a denote the same or corresponding parts, which will not be further described. The difference between FIG. 5b and FIG. 5a is, in FIG. 5b, gas diffuser 242 is fluidly connected to the liquid inlet 218 of the main dissolution column 202. In this embodiment, the injector 242 is placed between the pump 220 and the feed liquid inlet 218, so that $CO_2$ or mineral acid is injected into the main column 202 after the pump 220. In this embodiment, the pressure of the pre-treatment dissolution column 230 is lower than the pressure of the main dissolution column 202. For example, the pressure of the pre-treatment dissolution column 230 may be 3 barg and the pressure of the main dissolution column 202 may be 5 barg. In this case, any undissolved $CO_2$ mixes with ozone gas in the headspace 206 is injected back into the pre-treatment column 230. The benefits of this embodiment includes a reduced pH which could be achieved in the system since the acidic pressurized feed water is fed to the main dissolution column 202 that has a higher pressure than the pressure of the pre-treatment dissolution column 230. $CO_2$ injection at higher pressure leads to higher $CO_2$ dissolution and greater hydration of dissolved $CO_2$ into carbonic acid which results in a lower pH. Another benefit is the ability to reuse unused $CO_2$ accumulated within the headspace 206 that injects into the pre-treatment dissolution column 230.

Figure 5C:
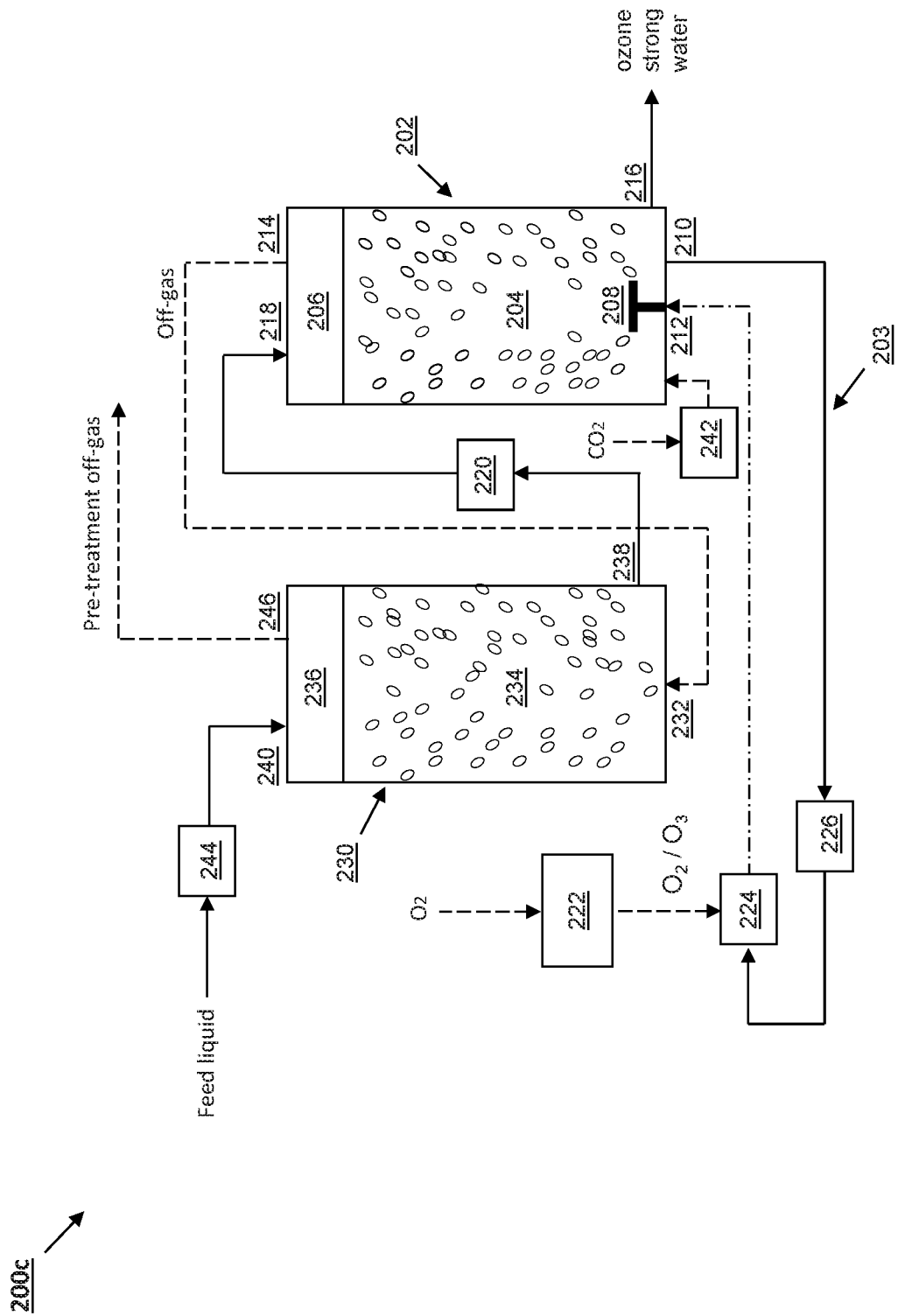
FIG. 5c is a block diagram of another exemplary two-stage ozone dissolution system.

A third embodiment for $CO_2$ or mineral acid injection is shown in FIG. 5c, in which the same reference numerals as those in FIG. 5a denote the same or corresponding parts, which will not be further described. The difference between FIG. 5c and FIG. 5a is, in FIG. 5c, gas diffuser 242 is fluidly connected to the bottom of main dissolution column 202 through an additional liquid inlet (not shown) in order to diffuse $CO_2$ gas into the body of the pressurized water in the main dissolution column 202. Thus, system 200c involves direct injection of the acidification agent into the bottom part of the main dissolution column 202 using the gas diffuser 242. The gas diffuser 242 may be any type of ceramic diffusers. This embodiment would ensure a better dissolution of $CO_2$ gas in addition to the ability to reuse any undissolved $CO_2$ in the off-gas that injects into the pre-treatment dissolution column 230.

In all the three embodiments listed above, numeral 242 may represent a gas/mineral acid injector if the available $CO_2$ pressure is higher than the corresponding liquid pressure, a venturi-injector if the available $CO_2$ pressure is lower than the corresponding liquid pressure, or a gas diffuser if $CO_2$ is directly diffused into the liquid.

Figure 5D:
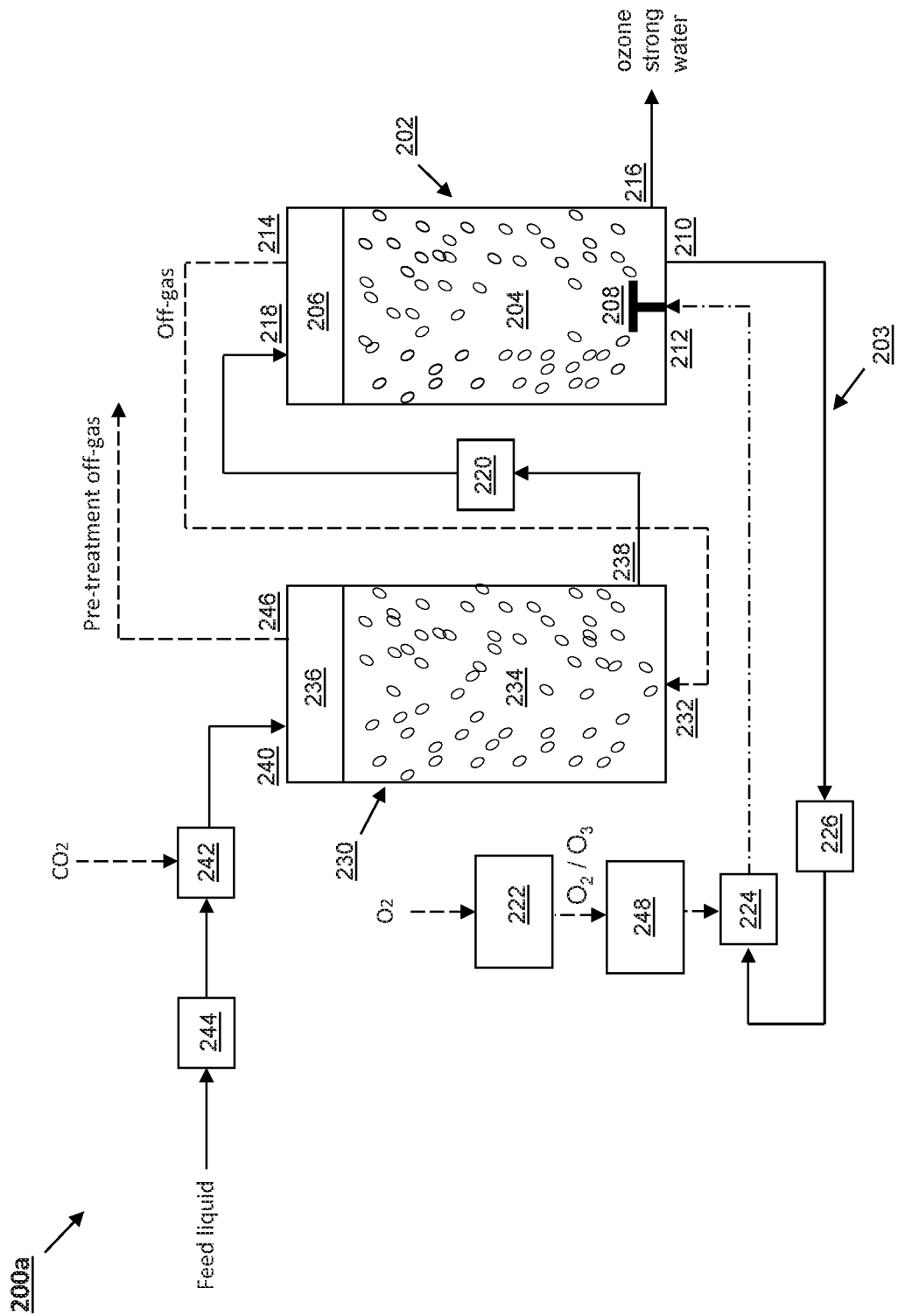
FIG. 5d is a block diagram of another exemplary two-stage ozone dissolution system.

A plurality of embodiments could be implemented for injecting the oxygen-ozone gas mixture generated by the ozone generator 222. One such variation is shown in FIG. 5d which utilizes a gas compression operation 248 which compresses the $O_2$-$O_3$ gas mixture up to a pressure slightly higher than the main dissolution column 202 pressure, with controlled temperature of the $O_2$-$O_3$ gas. In FIG. 5d, the same reference numerals as those in FIG. 5a denote the same or corresponding parts will not be further described. The difference between FIG. 5d and FIG. 5a is, in FIG. 5d, a gas compressor 248 is fluidly connected to the ozone generator 222 and the oxygen-ozone gas mixture generated by ozone generator 222 passes the gas compressor 248 before sent to the fluid recirculation loop 203. The compressed oxygen-ozone gas mixture is then injected into the recirculated liquid loop without using a venturi-injector. In this case, numeral 224 may be a gas injector or a ceramic gas diffuser. The advantage of this approach is the ability to achieve operational cost savings by reducing the pump output pressure required from the pump 226, with the use of a gas compressor 248 to pressurize the $O_2$-$O_3$ feed-gas to the required pressure.

The disclosed two-stage ozone dissolution system may be equivalent to a single-stage ozone dissolution system where the dissolution column height is extended. The continuous mode operation method for the single-stage ozone dissolution system 100a is also applied to the two-stage ozone dissolution system 200a, where the start-up mode and the steady state mode may coexist within the main dissolution column and the pre-treatment dissolution column due to the concentration gradient along the height of either of the columns. In the end, up to approximately 300 mg/L gas-free dissolved ozone water or gas-free liquid containing dissolved ozone or ozone strong water may be produced through the ozone strong water outlet of the main dissolution column 204, which may be seen in the examples that follow.

Returning to FIG. 1a, the produced ozone strong water coming out from the mass transfer unit 1 (from the ozone strong water outlet 122 in FIG. 2a or the ozone strong water outlet 216 in FIG. 5a) is forwarded to the mixing unit 2 where the ozone strong water is mixed with the process liquid to produce the homogeneous and gas-free liquid oxidant mixture of the ozone strong water and the process liquid therein for the liquid oxidation process for converting the process liquid into the oxidized liquid in the reaction unit 3 using the homogeneous and gas-free liquid oxidant mixture. More specifically, the ozone strong water outlet 216 may be fluidly connected to a plurality of injection nozzles in the mixing unit 2. The plurality of injection nozzles each may have a valve and may be adjusted to control the flow rate of the ozone strong water discharged from ozone strong water outlet 216 of dissolution column 202 to match the flow rate of the pre-treatment ozonated water fed to liquid inlet 218 of main dissolution column 202. The pump 220 may be adjusted to have the flowrate of the pre-treatment ozonated water from the pre-treatment dissolution column 230 matches the flowrate of the acidic pressurized feed water fed to the feed liquid inlet 240. In this way, while continuously producing the ozone strong water, the volumes of the liquid in the pre-treatment dissolution column and the main dissolution column are maintained constant, respectively.

One skilled in the art will recognize that if the main dissolution column is tall enough to allow sufficient residence time and sufficient dissolution of ozone gas in water, the ozone gas may be completely dissolved in water and little to no ozone remains in the off-gas stream. In this way no pre-treatment dissolution column is needed.

The disclosed two-stage ozone mass transfer system has the following advantages over the disclosed single-stage ozone mass transfer system. The two-stage ozone mass transfer system is capable of better utilization of the generated ozone with little to no loss of ozone in the off-gas. The undissolved ozone in the off-gas from the main dissolution column is fed into a pre-treatment dissolution column to produce a pre-treated ozonated water with a certain concentration of dissolved ozone. For example, the example below shows approximately 50 mg/L of dissolved ozone was obtained (see for example FIG. 11). Using this pre-treated ozonated water as a feed liquid fed into the main dissolution column, the concentration of the ozone strong water may be increased. For example, the example below shows the concentration of the ozone strong water was increased to approximately 300 mg/L (see for example FIG. 11). Therefore, the two-stage ozone dissolution process is able to capture any residual ozone from the off-gas stream, increase the concentration of the ozone strong water and perform a thorough use of ozone gas. Next, pure oxygen obtained as off-gas stream from the pre-treatment dissolution column could be used in other processes, such as a secondary wastewater treatment. Additionally, faster ozone dissolution in water in the two-stage dissolution procedure enables a higher throughput of the ozone strong water, which may be seen in the examples that follow, thus improving the economic viability of the system for real-life effluent treatment applications.

EXAMPLES

The following non-limiting examples are provided to further illustrate embodiments of the invention. However, the examples are not intended to be all inclusive and are not intended to limit the scope of the inventions described herein.

In the following Examples, all tests are performed with the dissolution column filled up to the same water levels.

Example 1: Diffuser Design

Diffuser types used in the disclosed gas mass transfer systems, including S-ring and Gap-ring diffusers and a cylindrical fluid feeder, were installed at the bottom cover of the dissolution column with sufficient clearance maintained from the bottom cover to avoid gas entrapment in the recirculation pump loop. Here, the cylindrical fluid feeder is a straight vertical conduit having approximately the same height and the same conduit diameter as that of S-ring or Gap-ring diffuser and installed in the bottom cover of the dissolution column fluidly connected with the fluid feed inlet. The cylindrical fluid feeder does not have diffuser.

Operations of the S-ring and Gap-ring diffusers involve dispersing the ozone feed gas as millimeter sized gas bubbles, which then gradually rise to the top with a characteristic directionality associated with the ascending movement of the gas bubbles. The diameter of the gas bubbles emerging out of these diffuser types could be regulated by varying their orifice diameters. For example, tests were performed with orifice diameter or the gap between the two round plates of Gap-ring diffuser varied between 2 mm, 4 mm and 6 mm by adjusting screws or the number of washers constituting the orifice or gap. In addition, each of the diffuser types has their unique gas flow patterns which were computationally studied as well as videoed in real time using submersible camera with the dissolution column unpressurized and open to the atmosphere. The experimental analysis of diffuser configurations was performed at varying pressure conditions (P=2 barg, 3 barg, 5 barg) and different water levels in the dissolution column.

Figure 6A:
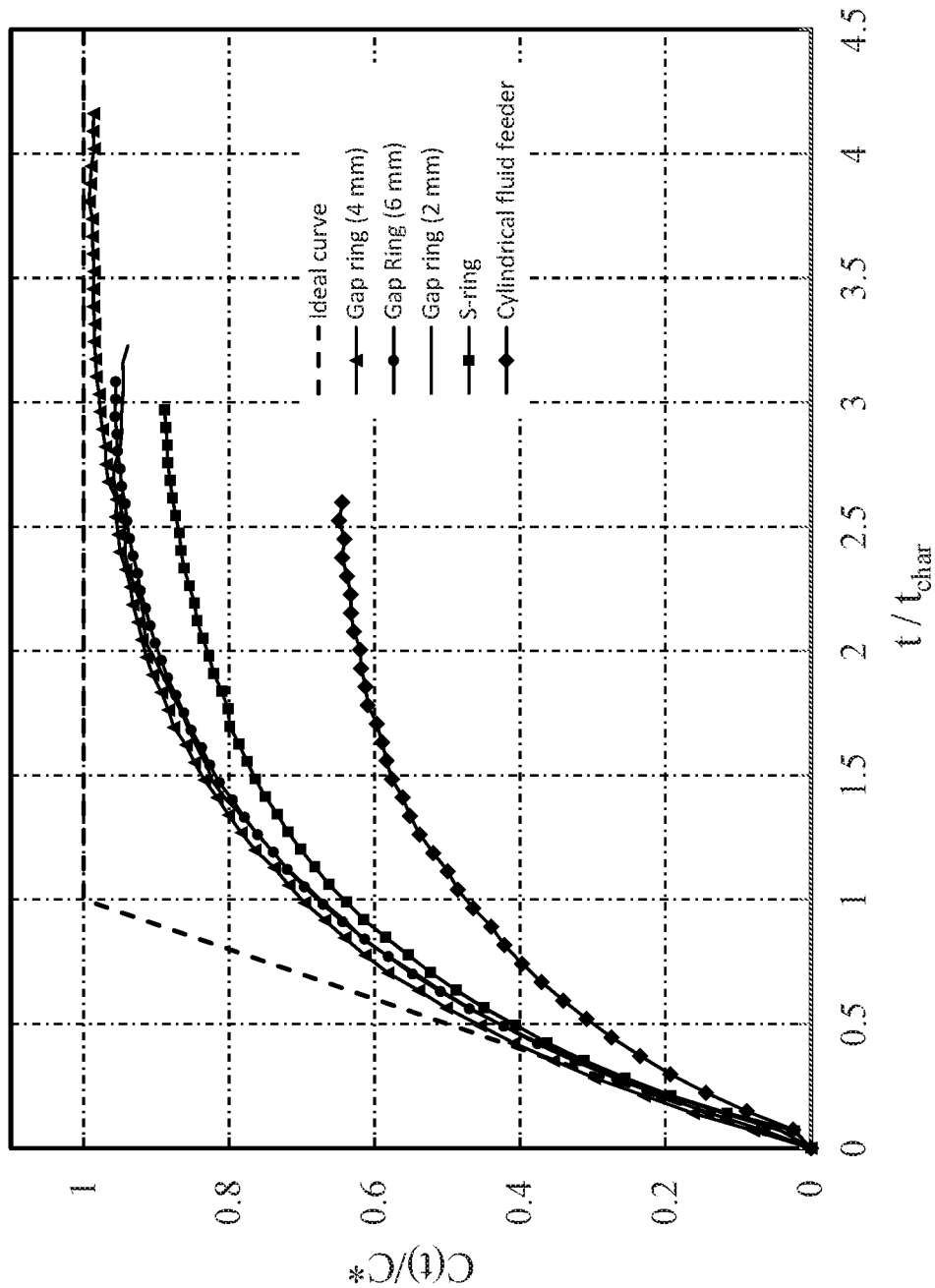
FIG. 6a is a comparison of the dimensionless concentration profiles at pressure=3 barg with the system shown in FIG. 2b for four diffusers and one cylindrical fluid feeder versus an ideal performance.
Figure 6B:
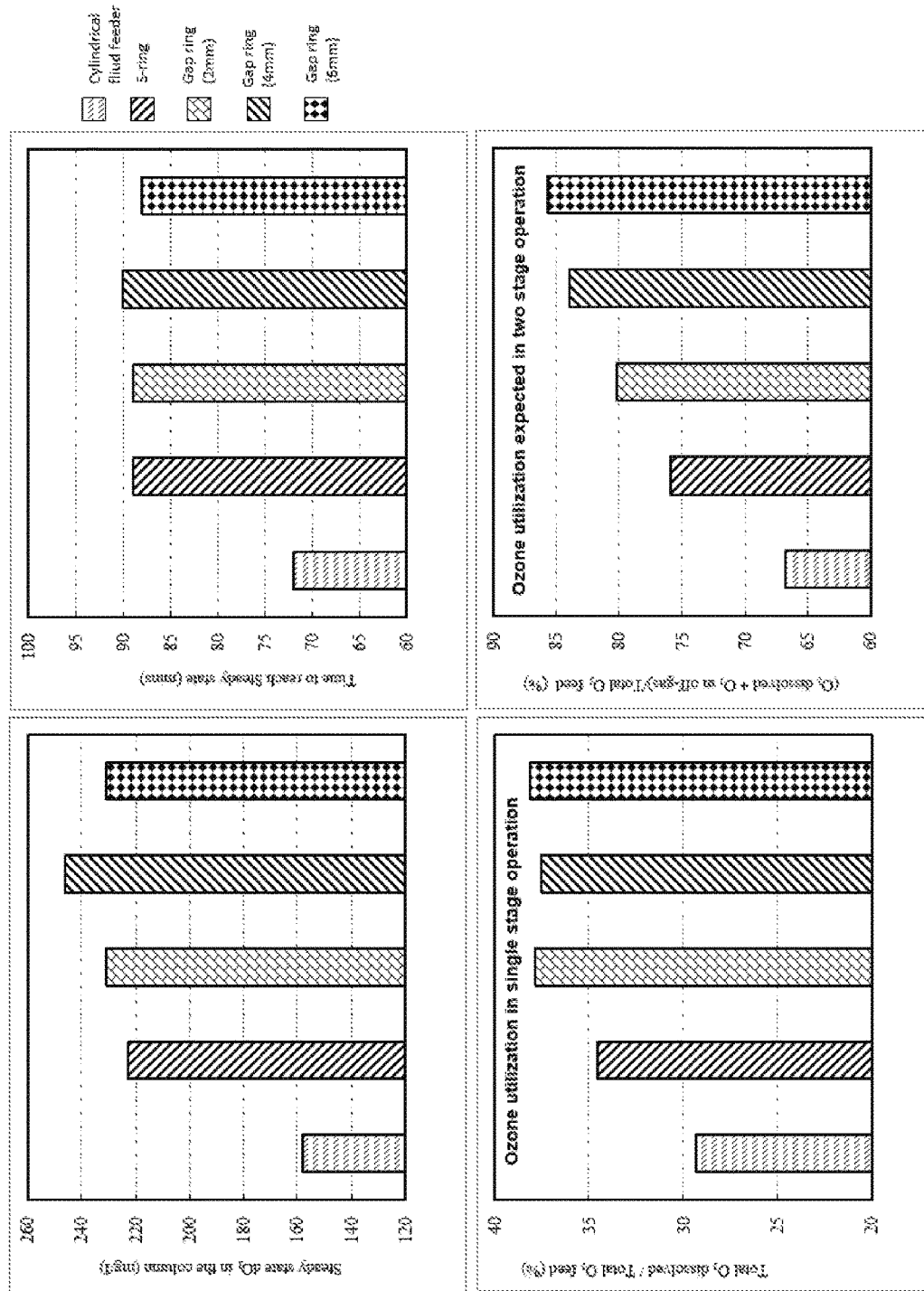
FIG. 6b is comparative plots of Key Performance Indicators (KPI) plotted for four diffusers and one cylindrical fluid feeder with the system shown in FIG. 2b at pressure=3 barg.

FIG. 6a and FIG. 6b are performance curves of the dimensionless concentration profiles and comparative plots of Key Performance Indicators (KPI) plotted for four different diffuser types, S-ring, Gap-Rings with 2 mm, 4 mm and 6 mm orifices and one cylindrical fluid feeder at pressure=3 barg. The experiments conditions are as follows. P=3 barg, pH=5, T=20° C., water volume=230 L, ozone feed=1.6 g/min. Here, C* represents equilibrium dissolved ozone concentration at operation conditions. The characteristic time $t_{char}$ calculates the time required to increase dissolved ozone levels in the liquid from 0 to C* assuming a 100% mass transfer efficiency from gas to liquid. It is seen that Gap-Ring with 4 mm gap had the best performance among the five, characterized in terms of the $dO_3$ concentration values obtained after a definite period of ozonation as well as the fraction of feed-gas ozone which was dissolved in the liquid phase. Furthermore, negligible difference in performance was observed even as the gap spacing was varied between 2, 4 and 6 mm in the Gap-ring diffuser, which possibly signifies a similar bubble diameter and residence time with various Gap-ring spacings.

Example 2: Effect of pH and Temperature

The temperature (T) and pH based performance of the dissolution column equipped with the cylindrical fluid feeder configuration, shown in FIG. 3c, was analyzed for the following set of conditions:

(i) T=10° C., pH=5, 7, 9
(ii) T=20° C., pH=5, 7, 9
(iii) T=30° C., pH=5, 7

Figure 7:
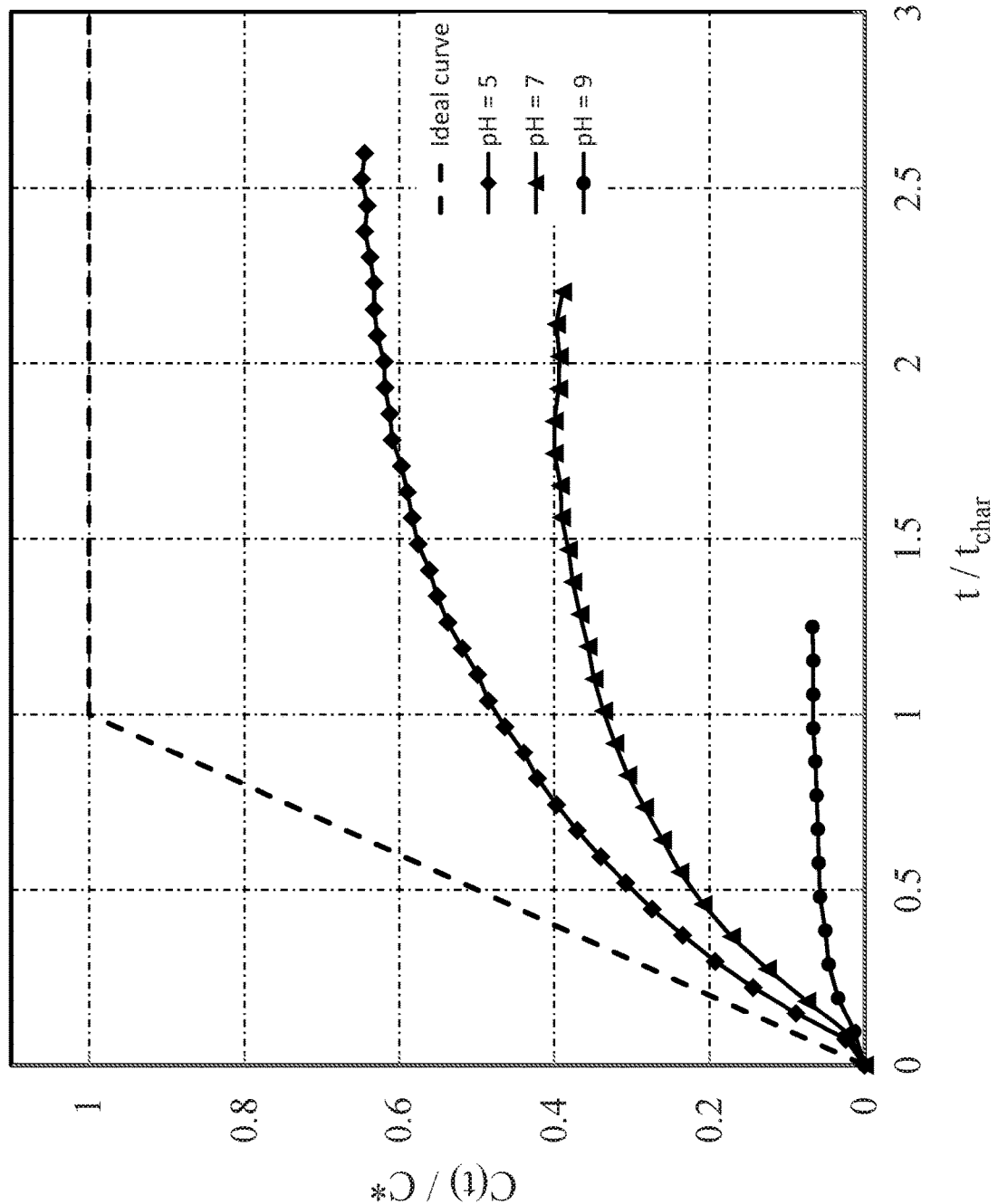
FIG. 7 is a dissolution column performance for various pH in comparison to the ideal performance at constant temperature of 20° C. and pressure of 3 barg with the system shown in FIG. 2b and utilizing a cylindrical fluid feeder.
Figure 8A:
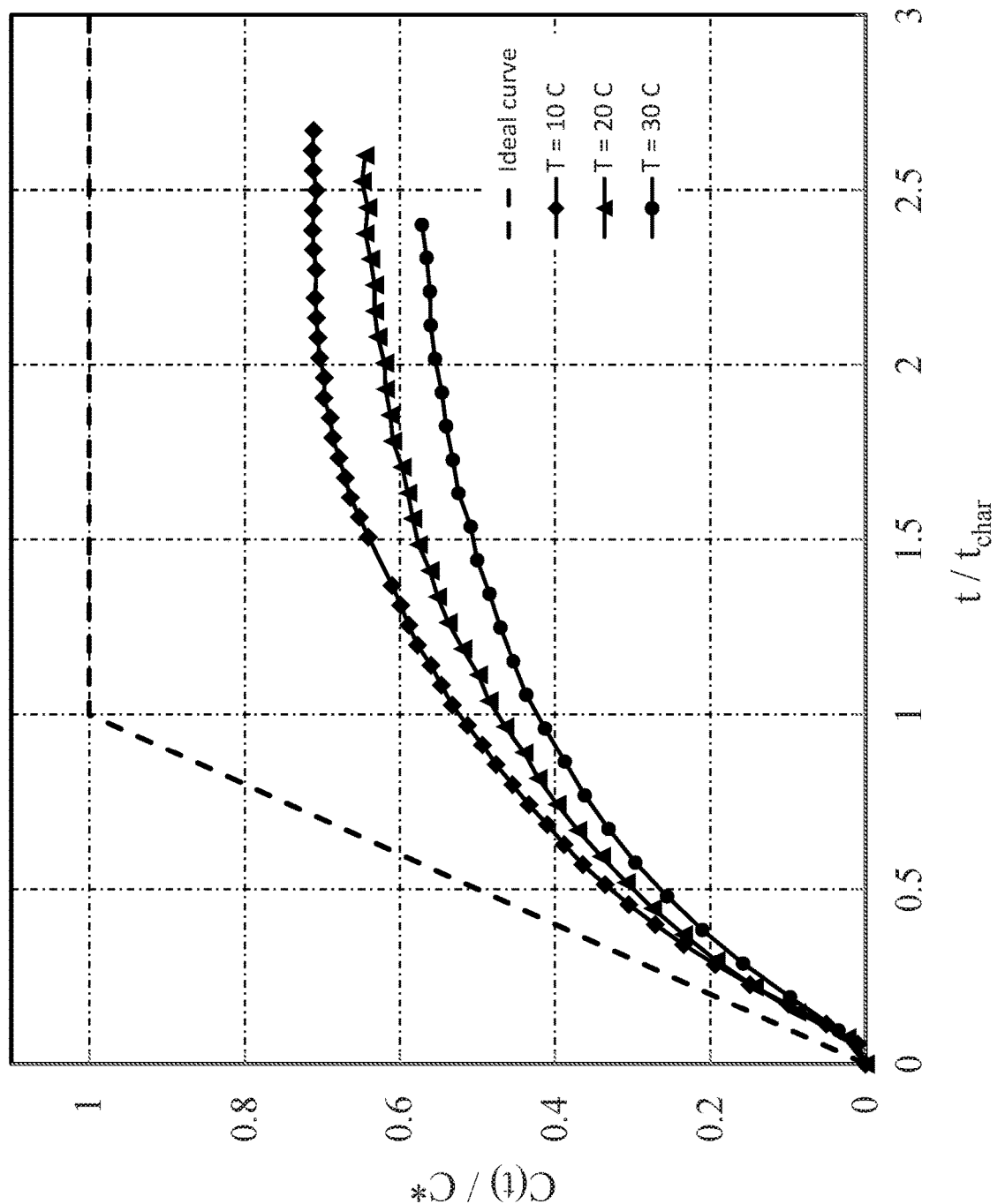
FIG. 8a is a dissolution column performance for various temperatures in comparison to the ideal performance at constant pH with the system shown in FIG. 2b with a cylindrical fluid feeder.

Tap water was filled in the dissolution column with an initial pH of ~7.5 and later adjusted to 5 by bubbling $CO_2$ gas. All the tests were performed with the same medium (i.e., tap water) filled to the same dissolution column levels as Example 1, that is, water volume is 230 L. In addition, the tests involved similar ozone dosages, that is, ~0.55 m³/hr of $O_2$ flow with an ozone concentration of 180 g/m³ which correspond to an ozone dosage of ~1.65 g/min. FIG. 7 is the system performance for various pH in comparison to the ideal performance at constant temperature. The experiment was performed using the a cylindrical fluid feeder at P=3 barg at 20° C. The pH used in the experiment ranging from 5 to 9. FIG. 8a is the system performance for various T in comparison to the ideal performance at constant pH=5 at P=3 barg. As shown, an optimized operation of the dissolution column based on the ideal performance curve demands a lowering of the pH and T values. Here the temperature used in the experiment ranging from 10 to 30° C.

Figure 8B:
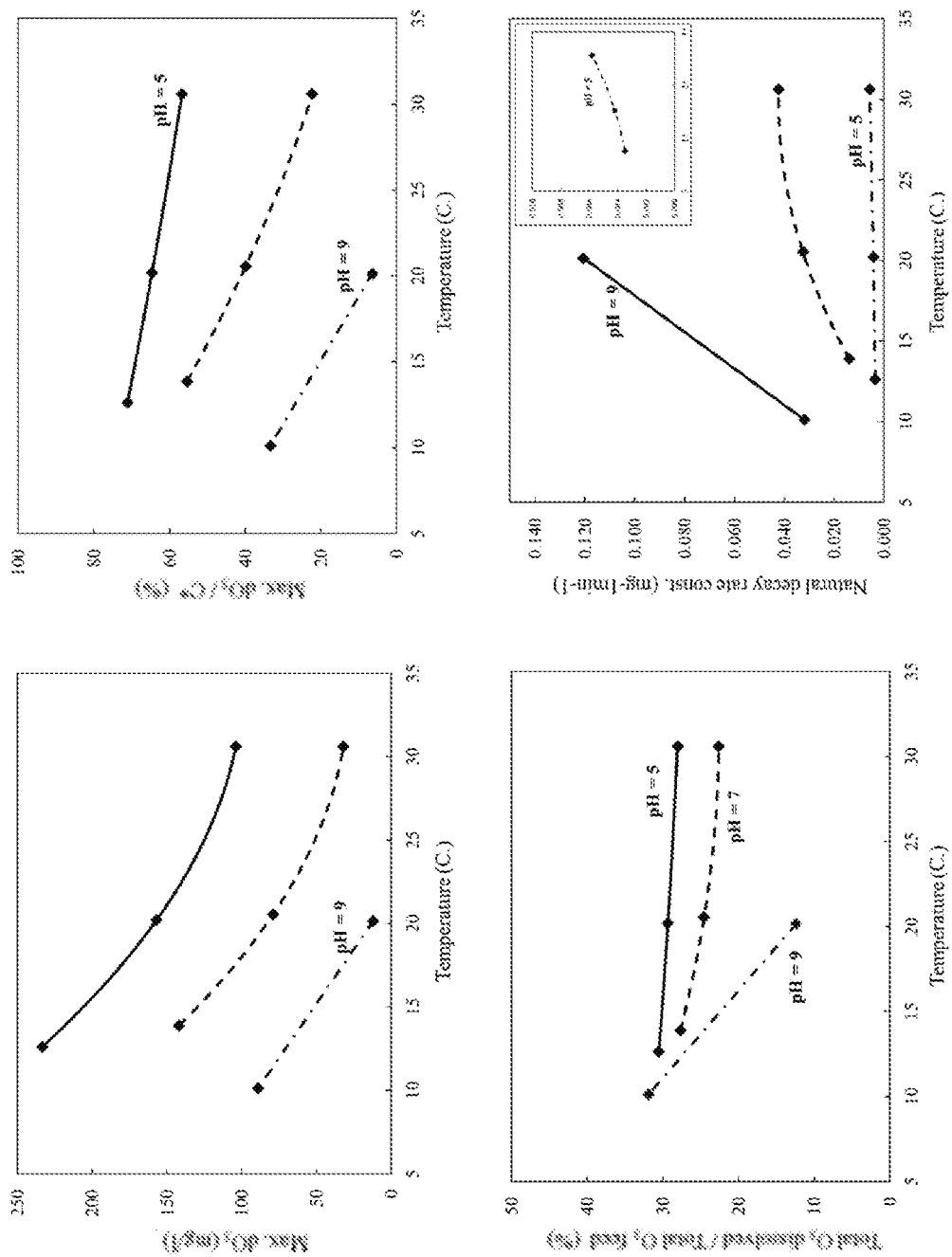
FIG. 8b is variations of KPIs with various pH and various T with the system shown in FIG. 2b and utilizing a cylindrical fluid feeder at pressure=3 barg.

FIG. 8b is variations of KPIs with pH (pH=5, 7, 9) and T (T=10, 20, 30° C.) with the cylindrical fluid feeder, pressure=3 barg and water volume=230 L. As shown, an optimized operation of the dissolution column demands a lowering of the pH and T values, with the following inferences drawn from the performance curves: (i) at constant temperature, maximum $dO_3$ (pH 5)>maximum $dO_3$ (pH 7)>maximum $dO_3$ (pH 9). While this indicates the steady state dissolved concentration attainable in the medium, the ratio of maximum $dO_3$ to equilibrium concentration represents the extent to which equilibrium conditions could be attuned during the reaction. A similar trend with pH were observed for both the parameters, with the deviation with increasing pH becoming more pronounced at higher temperatures for pH=5 and 7. (ii) at constant pH, maximum $dO_3$ (T=10° C.)>maximum $dO_3$ (T=20° C.)>maximum $dO_3$ (T=30° C.), with the trend for the ratio of maximum $dO_3$ to equilibrium concentration following a similar pattern.

The degradation of the system performance with increasing pH and T could be attributed to an increased reduction of dissolved ozone to oxygen under these conditions. It is known $OH^-$ ions present in water are capable of reacting with dissolved ozone to generate OH radicals, which eventually converts it to oxygen. At increased pH levels, the concentration of $OH^-$ ions in water steadily increases resulting in greater degradation of ozone, as reflected in lowering dissolved ozone concentration values as seen in the upper left figure of FIG. 8b. To this point, acidifying the pressurized feed water inhibits the formation of the OH radicals, thereby increasing the dissolved ozone concentration. Furthermore, the reaction rate (k) is significantly enhanced at higher temperatures. Both trends could be observed in the lower right figure of FIG. 8b which shows the variation of decomposition rate constant representing the decomposition of dissolved ozone to oxygen by reaction with $OH^-$ ions and OH radicals, hence, the value of k increased with an increase in pH and T.

Example 3: Effect of Pressure

Figure 9A:
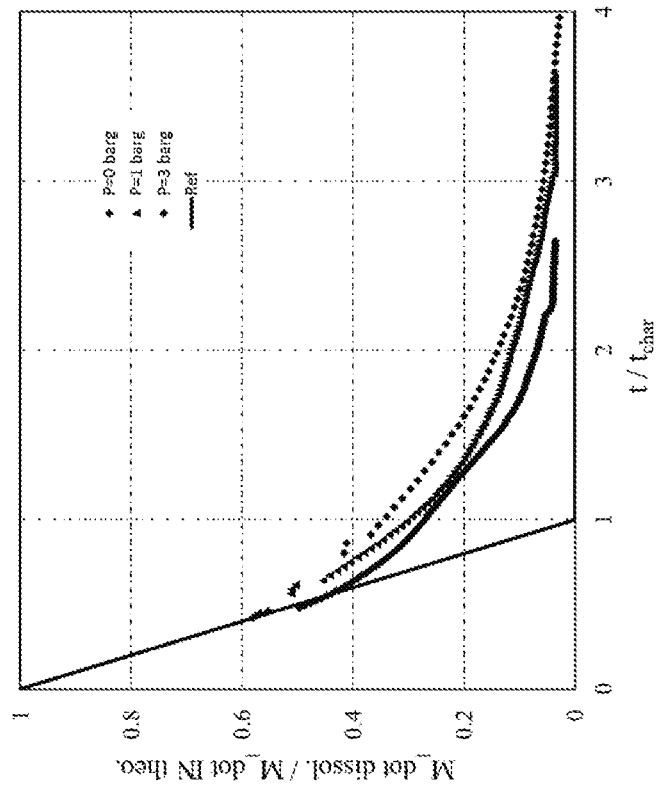
FIG. 9a is a dissolution column performance for various pressures in comparison to the ideal performance at constant pH and constant temperature with the system shown in FIG. 2b with a cylindrical fluid feeder.
Figure 9B:
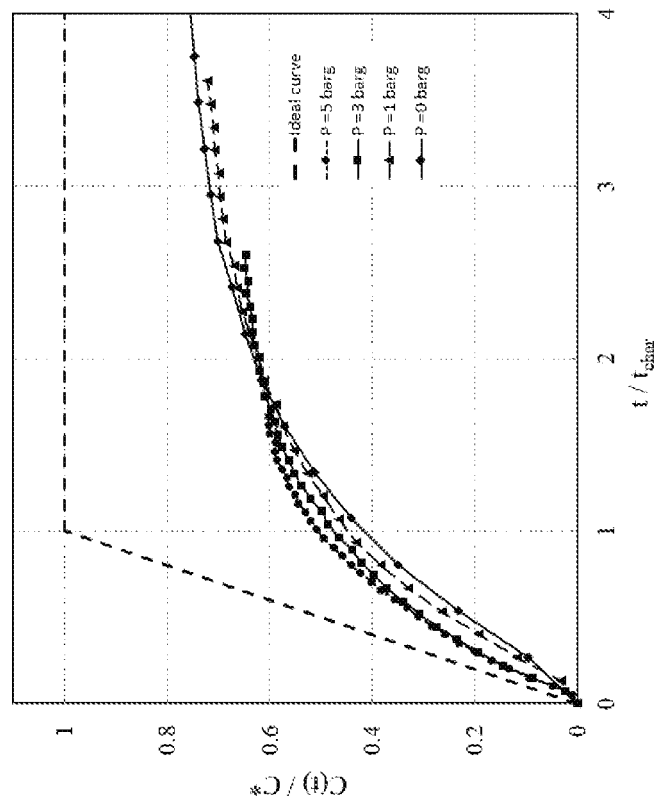
FIG. 9b is a dissolution column performance for various pressures versus the ideal mass transfer flux at constant pH and constant temperature with the system as shown in FIG. 2b with a cylindrical fluid feeder.

An effect of dissolution column pressure on the ozonation process is investigated for pressures ranging from 0 barg to 5 barg and the experiments performed at a constant pH=5, T=20° C. Tap water was used for the experiments. The variation in dissolved ozone concentrations and the relative time scales for the respective scenarios is given in FIG. 9a with the following observations: (i) The system attains steady state concentration values closer to the equilibrium at lower pressures, that is, maximum $dO_3/C^*$(P=0 barg)>maximum $dO_3/C^*$(P=1 barg)>maximum $dO_3/C^*$(P=3 barg) >maximum $dO_3/C^*$(P=5 barg); and (ii) The rate of mass transfer from gas to liquid phase was enhanced at higher pressures. This could be observed in the dimensionless concentration curves approaching the linear regime of the ideal performance curve in FIG. 9a. This inference could be further verified by comparing the respective curves against the ideal mass transfer flux curve in FIG. 9b, the slope of each curve being representative of the mass transfer flux for respective configurations. Accordingly, it could be observed that the transfer flux is higher at P=3 barg compared to that at 0 barg.

Figure 9C:
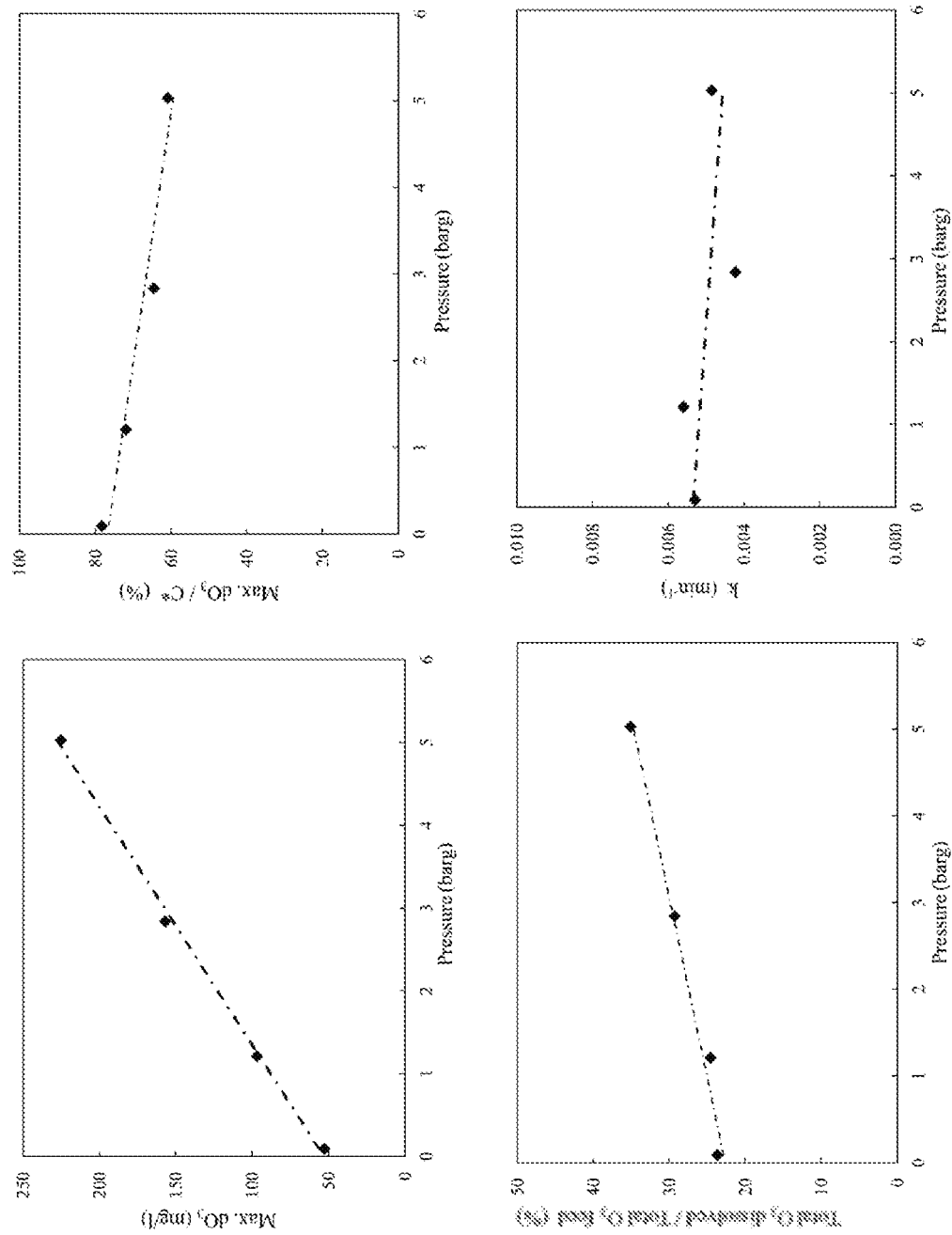
FIG. 9c is variations of KPIs of the ozone strong water dissolution column for variations in operating pressures with the system shown in FIG. 2b with a cylindrical fluid feeder.

A quantification of the performance indicators for various pressure values is shown in FIG. 9c which compares the maximum dissolved ozone levels. A linear trend is clearly evident for the steady state $dO_3$ values with increasing pressure, with the steady state concentration increasing from 50 mg/L for P=0 barg to 220 mg/L for P=5 barg (see upper left figure). This observed linear trend is in direct correspondence to that expected based on Henry's law—which predicts a linear increase in dissolved ozone concentration in liquid with increase in pressure.

The decay kinetics of the system which investigates the decomposition rate of dissolved ozone to oxygen was expected to remain approximately unchanged even with a variation in dissolution column pressure, as the decay kinetics depends primarily on the composition of liquid which would remain unchanged even with a variation in pressure.

This evaluation could be further verified by the nearly constant value for Decay constant (k) of around 0.005 min$^{-1}$ observed for the experiments (see lower right figure). The minor reduction in the values observed in the plot could be attributed to the recirculation flow rates as the dissolution column pressure is increased.

Example 4: Single-Stage Ozone Dissolution Process

Figure 10:
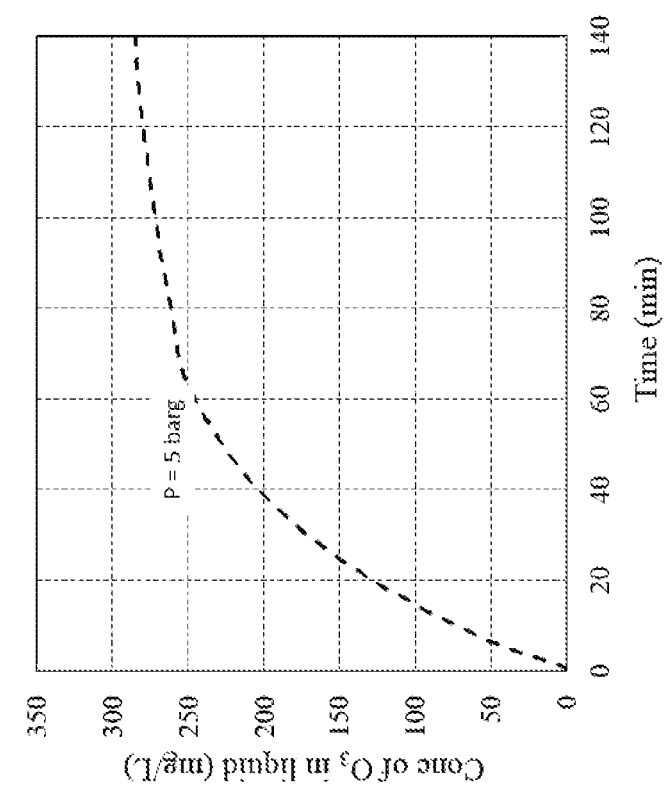
FIG. 10 is a dissolved ozone profile when ozonation was performed in a single stage at pressure=5 barg with an ozone feed gas concentration of 160 g/m$^3$ and an S-ring diffuser.
Figure 12:
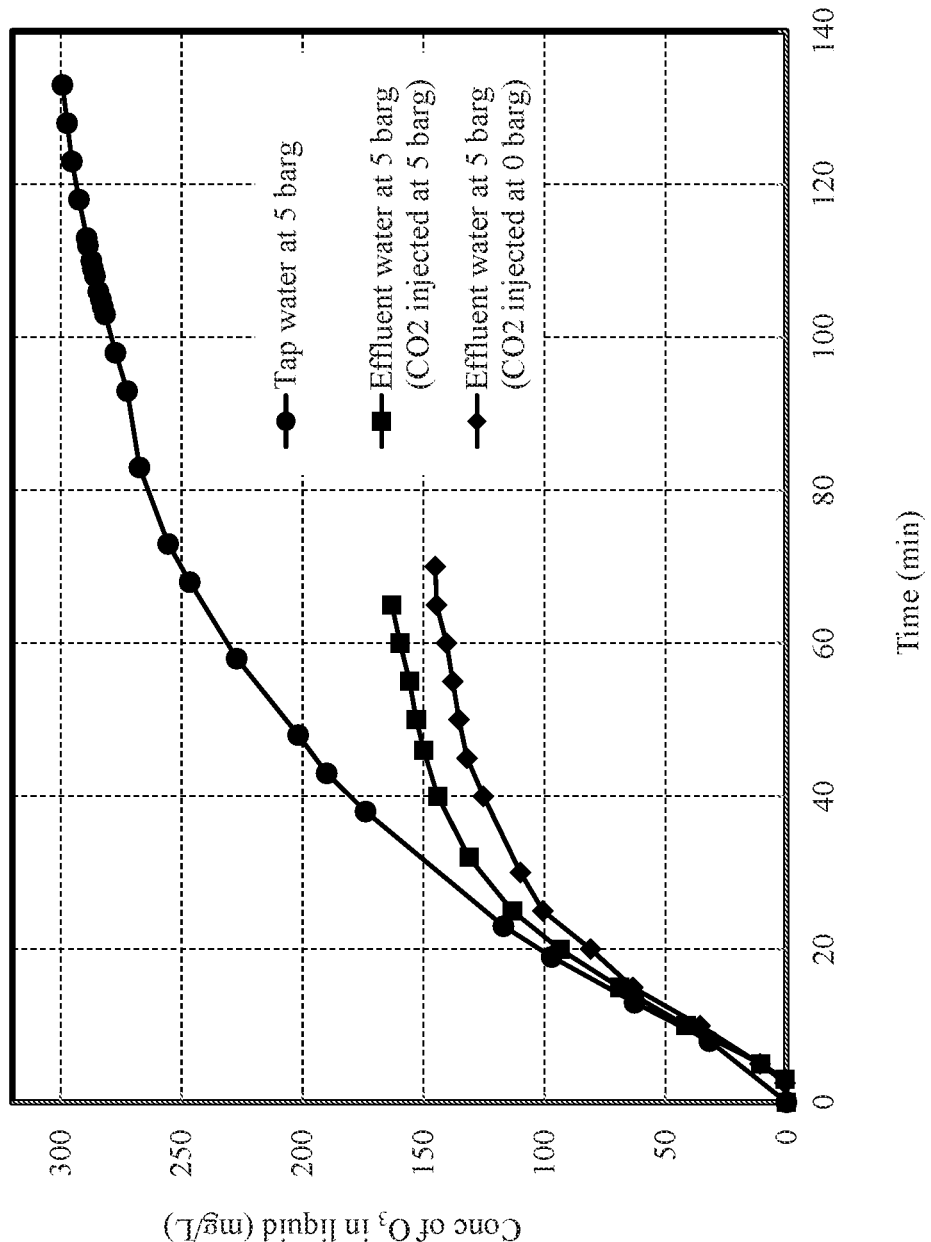
FIG. 12 is a comparison of dissolved ozone values at varying pH of the effluent water with tap water profile as the reference, with the system shown in FIG. 2b using a Gap Ring diffuser (4 mm), temperature of 20° C. and a pressure of 5 barg.

In a single stage ozone dissolution process with tap water performed at pressure=5 barg, pH=5, 20° C., referring to FIG. 10, with batch operation using a S-ring diffuser and an ozone feed gas concentration of 160 g/m$^3$, it was observed that the concentration of ozone gas in the off-gas at a steady state is approximately 120 g/m$^3$ and the concentration of dissolved ozone in water is yielded with a steady state value of approximately 280 mg/L. Furthermore, when the same experiment was performed using a Gap ring diffuser (4 mm) using tap water, as shown in FIG. 12, a steady state value of approximately 300 mg/L was attained.

Example 5: Two-Stage Ozone Dissolution Process

Figure 11:
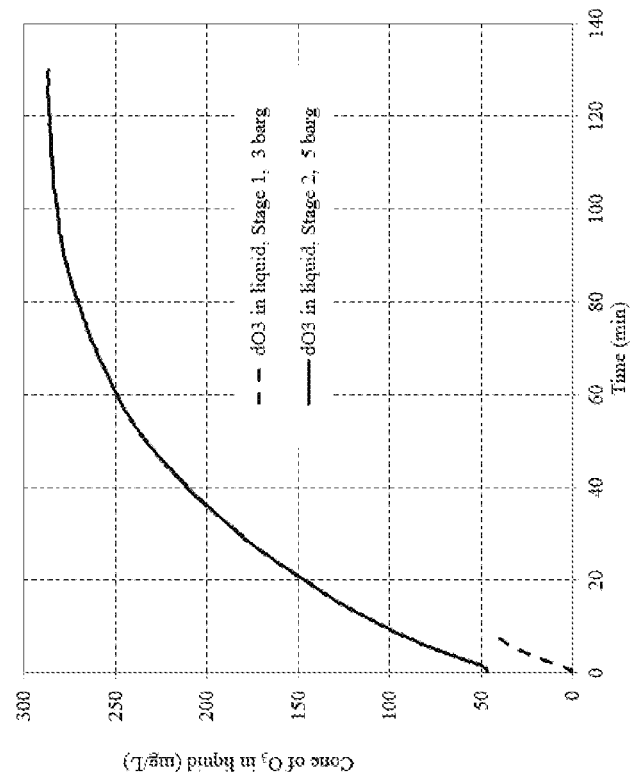
FIG. 11 is an exemplary evolution profile of dissolved ozone concentrations in water over time produced in Stage 1 and Stage 2 of a two-stage ozone dissolution system using an S-ring diffuser, with the system shown in FIG. 2b.

Referring to FIG. 11, a development of dO$_3$ profiles in the pre-treatment dissolution column (Stage 1) and the main dissolution column (Stage 2) of a two-stage ozone dissolution process, with the system shown in FIG. 2b, is shown for a batch-mode operation with tap water. The main stage (Stage 2) was performed at 5 barg, pH=5, 20° C., with an ozone feed gas concentration of 160 g/m$^3$. The pre-treatment stage (Stage 1) was performed at 3 barg, pH=5, 20° C., with an ozone feed gas concentration of 120 g/m$^3$. This correspond to the steady state off-gas from the main stage having an ozone concentration of 120 g/m$^3$ when operated at 5 barg (see Example 4). During the course of operation, the ozone concentration in the pre-treatment off-gas vent out of the pre-treatment dissolution column was continuously monitored. The ozone gas fed into the pre-treatment dissolution column was discontinued when the pre-treatment off-gas concentration reached a value of 0.5 g/m$^3$, an indication of the operation of the pre-treatment dissolution column with less to no ozone lost through the off gas. The concentration of dissolved ozone in water produced in the pre-treatment dissolution column at the end of ozonation was approximately 50 mg/L, referring to dashed line in FIG. 11.

The main stage of a two-stage ozone dissolution process with tap water was performed at 5 barg, pH=5, 20° C., using a S-ring diffuser with an ozone feed gas concentration of 160 g/m$^3$. Oxygen was injected into the dissolution column headspace to achieve a pressure of 5 barg without any removal of dissolved ozone from the liquid. The ozonation in the main stage was continued until a steady state was attained. The concentration of ozone strong water produced in the main dissolution column reached approximately 280 mg/L, referring to solid line in FIG. 11.

The corresponding dissolution column pressures in each stage of operation are also shown in FIG. 11, i.e., the pressure of Stage 1 is 3 barg; the pressure of Stage 2 is 5 barg. The ozonation in Stage 1 led to dO$_3$ level of approximately 50 mg/L. The restart of ozonation in Stage 2 yielded a dO$_3$ profile with a steady state value of approximately 280 mg/L with an ozone feed gas concentration of 160 g/m$^3$.

Example 6: Comparison of Single-Stage and Two-Stage Operations

FIG. 10 is a development of dO$_3$ profiles in a single stage at a pressure (P$_{top}$) of 5 barg, in which a 280 mg/L dissolved ozone concentration at the steady state is achieved in a batch operation. FIG. 11 is a development of dO$_3$ profiles in the pre-treatment stage (Stage 1) and the main stage (Stage 2) in which an approximately 280 mg/L dissolved ozone concentration at the steady state is achieved in a batch operation. The results shown in FIG. 10 and FIG. 11 are a combination of simulated and test data using a laboratory batch operation. Water filled in the single-stage and two-stage was tap water. From a comparison of the dO$_3$ profiles in FIG. 10 and FIG. 11, similar steady state value of dO$_3$ concentrations were obtained in single-stage as well as two-stage ozonation process with same ozone feed-gas concentration of 160 g/m$^3$, but with more efficient O$_3$ feed gas utilization in the two-stage.

Example 7: Generating Ozone Strong Water with Effluent Water

Effluent water contains soluble constituents, such as, COD, NH$_3$, nitrites etc., which consumes dissolved ozone and may be oxidized by the dissolved ozone to CO$_2$ and NO$_3^-$ respectively, during the ozonation process.

Ozone loss at pH=5 is much lower than pH=7 during the ozonation of the feed liquid in the dissolution column. A comparison of the results obtained with effluent water using a Gap-ring diffuser at 3 barg, T=20° C. gives a cumulative ozone loss of 10 g O$_3$ at pH=5 compared to 16 g O$_3$ at pH=7 for 20 mins of ozonation.

FIG. 12 compares dissolved ozone values at varying pH of the effluent water, with tap water's profile as the reference. Batch experiments for tap water were performed using Gap-ring (4 mm) as the diffuser at pH=approximately 5, P=5 barg, T=20° C. The CO$_2$ injection into the effluent water at high pressure (e.g., P=5 barg) yields a pH=4.5, whereas a pH=5.5 was obtained when CO$_2$ was injected at atmosphere pressure. After the pH of the effluent water was suitably adjusted, batch experiments were performed using the Gap-ring diffuser at P=5 barg and T=20° C. It could be observed in the initial 20 minutes of ozonation, the dO$_3$ profile with effluent water at pH=4.5 closely matches to that of tap water at P=5 barg, pH=5 and T=20° C. The shaded region of interest highlighted in FIG. 12 represents a normal operating regime of the system. In continuous experiments, residence times are chosen which would yield high gas to liquid mass transfer flux, which are typically of the order of 15 to 20 min. Within this shaded region of actual operation, it could be observed that ozonation of effluent water lowered to pH=4.5 could yield similar performance as the ozonation of tap water. Thus, pH lower than 5, preferably 4 obtained by injecting CO$_2$ at a high pressure, such as 5 barg, is beneficial for generating the ozone strong water using the effluent water as water source.

Example 8: Continuously Generating Ozone Strong Water with Tap Water

All continuous mode experiments were performed with tap water on a dissolution system as shown in FIG. 2a, a single-stage ozone dissolution system using a Gap-ring (4 mm) diffuser as a diffuser device. Furthermore, the dissolution column volume was 230 liters; pressure in the dissolution column was maintained approximately 5 barg throughout the experiment; pH was maintained at approximately 5 and temperature was maintained approximately at 20° C. A gas flow rate of 0.55 m$^3$/hr of O$_2$ fed to an ozone generator and a feed ozone concentration of 180 g/m³ in the oxygen-ozone gas mixture were applied to the fluid recirculation loop in the system.

In the case of continuous mode operation, the system operation involved a continuous outflow of dissolved ozone water (i.e., ozone strong water) from a dissolution column 100a as shown in FIG. 2a, along with a continuous inflow of fresh tap water (i.e., feed liquid) into the dissolution column 100a. The flow rate of the fresh tap water to the column was varied between 1 gpm-5.7 gpm. The outflow of the ozone strong water was manually adjusted by changing the number of injection nozzles in the mixing unit (e.g., a total of 5) and using the flow adjustment valves. The inflow of the fresh tap water was adjusted using a level probe coupled with a PID controller, which in turn modulated the pump frequency to yield a matching inflow of a pressurized feed water into the dissolution column. Simultaneously, $CO_2$ gas was introduced into the inflow of the pressurized feed water for pH adjustment. The $O_3$ gas injection into the system utilized a venturi-injector 126 in the fluid recirculation loop 103, with a flowrate of 0.55 m³/hr and an ozone concentration of 180 g/m³ in the oxygen-ozone mixture. The ozonation of the system with a continuous inflow of tap water and a continuous outflow of the ozone strong water was continued.

The system was operated in the continuous mode until the concentration measurement of the dissolved ozone in the fluid recirculation loop 103 shows negligible variation with time. The system was assumed to have attained a steady state concentration with time.

Figures 13, 14:
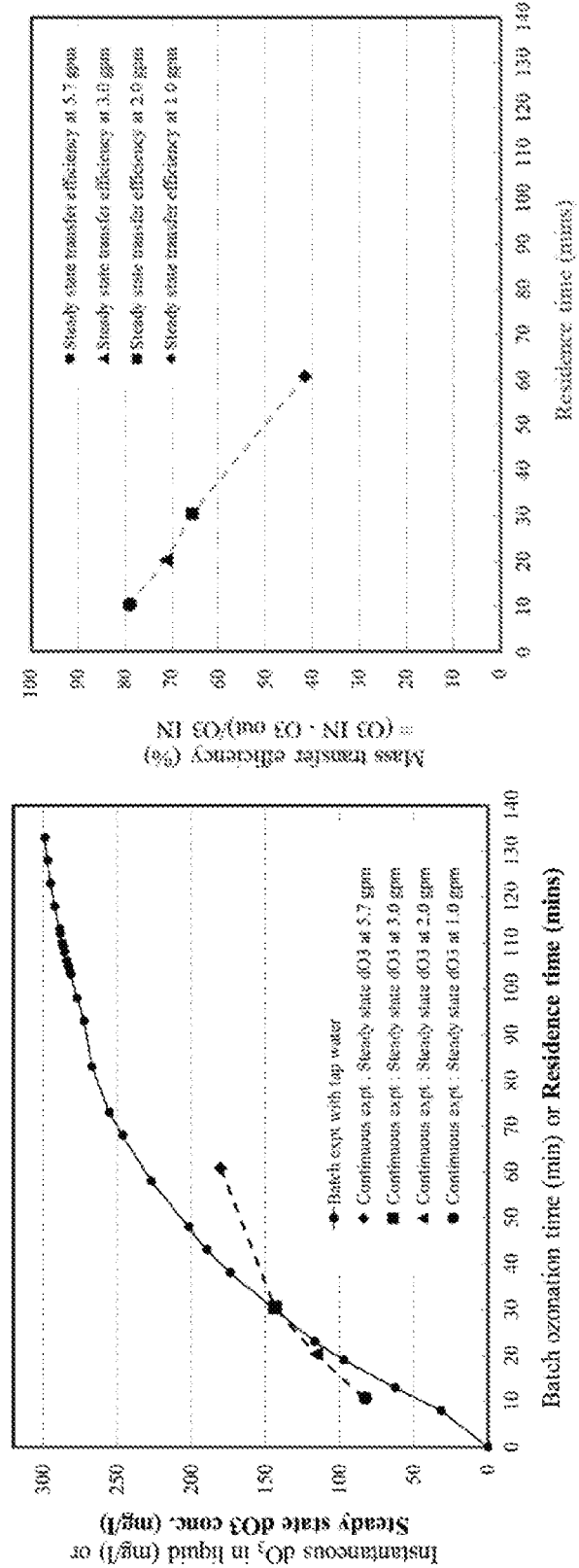

FIG. 13 compares the batch mode data using tap water, in which the system was operated as shown in FIG. 2b, to the multiple continuous operation results, in which the system was operated as shown in FIG. 2a. The profile shown for batch experiment is a plot of dissolved ozone concentration in the dissolution column versus batch ozonation time. The batch experiment was done at P=5 barg, T=20° C., pH=5, using a Gap-ring (4 mm) diffuser. The profile shown for continuous experiments is a plot of dissolved ozone concentration in the fluid recirculation loop after a steady state is achieved versus the residence time of the feed water in the dissolution column corresponding to the specific flow rate. As shown, the performance of the system in continuous mode is better than that expected based on batch experiments for flow rates greater than 3 gpm, which corresponds to residence times of less than 30 minutes. This could be attributed to a higher mass transfer rates from gas to liquid phase due to continuous addition of the fresh tap water into the system. Due to the higher mass transfer rate, the liquid is able to attain a higher dissolved ozone concentration than batch mode operation by the time it reaches the bottom of the dissolution column. There is, however, a contrasting behavior for flow rates less than 3 gpm (residence time >30 mins). This might be due to fluid segments spending significantly longer times in the dissolution column, and the decomposition of dissolved ozone to oxygen gaining prominence with time.

FIG. 14 is a comparison of mass transfer efficiency obtained after the system has attained a steady state condition for various liquid flow rates through a dissolution column, with the system shown in FIG. 2a using a Gap Ring diffuser (4 mm), and pH of approximately 5, temperature of approximately 20° C. and a pressure of approximately 5 barg maintained during the course of operation. In this case, the system was operated with a continuous flow of tap water as shown in FIG. 2a. As shown in FIG. 14, the mass transfer efficiency increases linearly with increasing liquid flow rates. Based on the principles of mass transfer, when gas is dissolved in liquid, the mass transfer rate is directly proportional to (C*—C), where C* is the saturation concentration and C is the measured concentration. Thus, the mass transfer rate is the highest when (C*—C) is maximum, i.e., with the fresh feed water with $dO_3$=0 mg/L. At a higher water flow rate of 5.7 gpm, the ozone gas added into the dissolution column comes into contact with the liquid phase with higher (C*—C) at the top of the column, thereby translating to a higher mass transfer efficiency at a higher flow rate.

Figure 15:
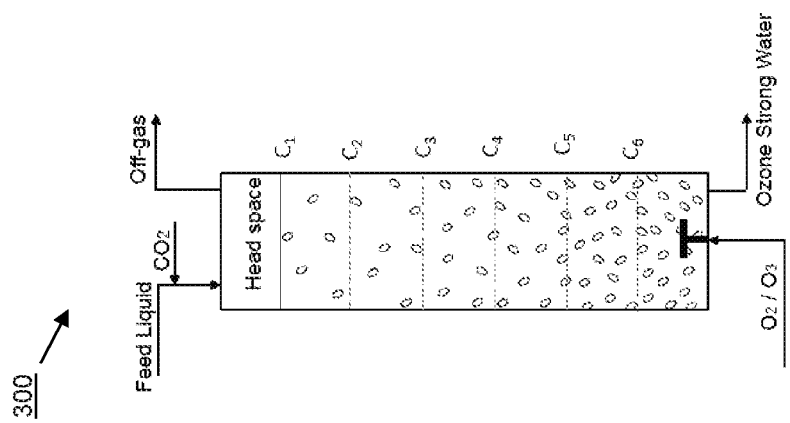
FIG. 15 is a block diagram of an exemplary high-pressure stainless steel column used as an ozonation dissolution column under continuous operation.

Example 9: Measurement of a Concentration Gradient of Dissolved Ozone in Continuously Generating Ozone Strong Water with Tap Water FIG. 15 shows a schematic of a high-pressure stainless steel column which was used as a dissolution column, in which dashed lines denote the cross-sectional planes where concentrations (e.g., $C_1$ to $C_6$) of the dissolved ozone were measured and elliptical dots denote gas bubbles. A volume of water in the dissolution column has a total height of 1.86 m with six flanges provided along the height of the dissolution column, which enables a sample collection and dissolved ozone concentration analysis for an analysis of dissolved ozone profiles along the height of the dissolution column. The sampling points in the column were spaced at a distance of 0.3 m. With a column inside diameter of 0.39 m, this corresponds to ~40 liters between each sampling point. The ratio of height/diameter of the volume of water is approximately 5:1. The dissolved ozone concentration at the top of the volume of water was assumed to be 0 mg/L.

Figure 16:
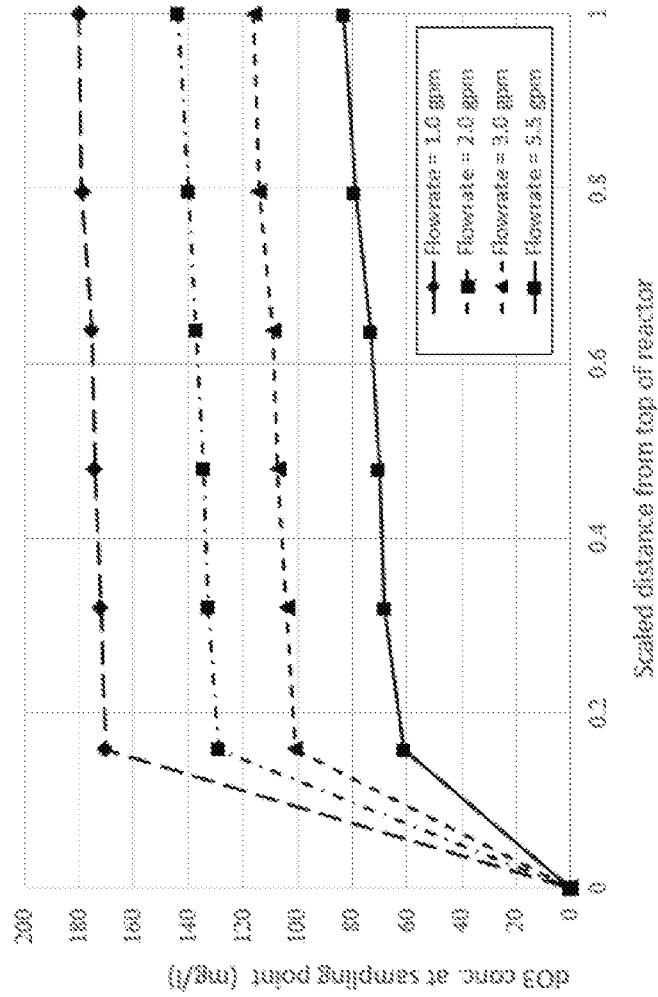

FIG. 16 is a plot of an ozone concentration gradient as a function of height of the dissolution column after the system has attained a steady state condition with various flow rates, in continuous operation mode with the system shown in FIG. 2a using a Gap Ring diffuser (4 mm), pH of approximately 5, temperature of approximately 20° C. and a pressure of approximately 5 barg maintained during the course of operation. As seen in the plot, dissolved ozone concentration gradients for various flow rates of the fresh feed water are formed along the height of the dissolution column starting from the second sampling point. The fresh feed water enters into the dissolution column at $dO_3$=0 mg/L. However, as the fresh feed water travels to the next sampling point, it gets mixed significantly with the ozonated water already present, thereby increasing the concentration to 170 mg/L as observed for 1.0 gpm. The total difference in dissolved ozone concentration between top and bottom sampling points in this case is 10 mg/L. In comparison, for a flow rate of 5.7 gpm, the dissolved ozone concentration difference is doubled to 20 mg/L but the dissolved ozone concentrations at the bottom is low. In contrast, a flow rate of 3 gpm provides almost 20 mg/L difference of the dissolved ozone concentration and moderate dissolved ozone concentrations. One of ordinary skill in the art will recognize if the height of the dissolution column is increased sufficiently, the feed water has sufficient residence time within the column and is hence able to attain a concentration close to the saturation concentration as shown in FIG. 4 and FIG. 10. In this case, for a flow rate of 3 gpm, if the height of the dissolution column is sufficiently increased, the dissolved ozone concentration at the lowest sampling point (e.g., $C_6$ in FIG. 15) for a pH=5, T=20° C. and P=5 barg would be greater than 280 mg/l as could be seen in FIG. 10 with batch operation. Thus, giving enough height of the dissolution column and enough height of the body of the acidic pressurized water, the dissolved ozone concentration at the lowest sampling point in the continuous mode should be able to reach the steady state dissolved ozone concentration in the batch mode.

It should be appreciated that, to our knowledge, the typical dissolved ozone concentration in the competing prior art systems is around 50 mg/L (e.g., U.S. Pat. No. 9,248,415) currently. The disclosed methods of dissolving ozone in water acidify pressurized water, so that the dissolved ozone concentration reaching the saturated or close to the saturated concentration can be realized.

In addition, the size of the disclosed dissolution system or mass transfer unit, included in a decoupled system that separates an ozone oxidation process in liquid media into three unit operations for process optimization, has a reduced volume compared to the current methodologies for ozone dissolution. This would greatly reduce the cost of delivering ozone to water for disinfection and oxidation of chemicals with a very small amount of water (e.g., around 1/20 compared to the tank volume of 333 m$^3$). This reduction in water usage translates directly to lower energy usage and costs.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A system for continuous production of a gas-free liquid containing ozone, the system comprising:
   a) a first gas injection device configured and adapted to inject an acidification agent into a pressurized feed liquid stream to maintain a pH value of the pressurized feed liquid stream below 7;
   b) a dissolution column including:
      (i) a pressure vessel, configured and adapted to contain a body of acidic pressurized liquid and an off gas in a headspace above the body of the acidic pressurized liquid;
      (ii) an inlet, configured and adapted to permit passage of an acidic pressurized feed liquid stream, after the injection of the acidification agent, into the pressure vessel through the headspace;
      (iii) an off-gas vent, configured and adapted to release the off gas contained in the headspace of the pressure vessel so as to maintain a pressure of the pressure vessel within a pre-determined pressure range; and
      (iv) an outlet, configured and adapted to discharge the gas-free liquid containing ozone from the pressure vessel;
   c) a fluid recirculation loop having
      a fluid inlet, fluidly connected to the dissolution column, configured and adapted to receive a fluid from the dissolution column;
      a second gas injection device, configured and adapted to inject ozone into the fluid being recirculated by the fluid recirculation loop; and
      a fluid injection device, within the pressure vessel, mounted on the bottom of the pressure vessel, configured and adapted to diffuse the fluid, after the injection of ozone, into the body of the acidic pressurized liquid in the pressure vessel, thereby injecting ozone therein;
   d) a controller, configured and adapted to adjust a flow rate of the acidic pressurized feed liquid stream fed to the inlet of dissolution column so as to yield an inflow of the acidic pressurized feed liquid stream that enables to continuously produce the gas-free liquid containing ozone; and
   e) at least one injection nozzles each controlled by a valve, fluidly connected to the outlet of the dissolution column, configured and adapted to adjust a flow rate of the produced gas-free liquid containing ozone discharged from the outlet of the dissolution column to match the flow rate of the acidic pressurized feed liquid stream fed to the inlet of the dissolution column so as to maintain a start-up mode in an upper portion of the pressure vessel that favors a high efficiency of ozone mass transfer into the acidic pressurized liquid and a steady-state mode in a lower portion of the pressure vessel that favors a high dissolved ozone concentration in the acidic pressurized liquid coexistent in the body of the acidic pressurized liquid in the pressure vessel,
   wherein a concentration gradient of dissolved ozone is formed along a height of the body of the acidic pressurized liquid.

2. The system of claim 1, wherein the fluid injection device is selected from a S-ring shape diffuser device or a Gap-ring shape diffuser device.

3. The system of claim 2, wherein the S-ring shape diffuser device includes
   a S-shape conduit, each end of the S-shape conduit being a nozzle; and
   a hollow post, one end of the hollow post fluidly communicating with a hole at the lateral center of the S-shape conduit and the other end of the hollow post fluidly communicating with the fluid recirculation loop.

4. The system of claim 2, wherein the Gap-ring shape diffuser device includes:
   a bottom round plate, having a through-hole in the center;
   a top round plate, parallel with the bottom round plate and supported with adjustable posts mounted between the top round plate and the bottom round plate, having a conus in the center, the conus partially inserted into the center of the through-hole of the bottom round plate; and
   a hollow post, fluidly communicating with the through-hole of the bottom round plate and the fluid recirculation loop.

5. The system of claim 4, wherein a clearance between the top round plate and the bottom round plate ranges from approximately 2 mm to approximately 6 mm.

6. The system of claim 4, wherein a clearance between the top round plate and the bottom round plate is approximately 4 mm.

7. The system of claim 1, wherein the acidification agent is selected from $CO_2$ gas or a mineral acid.

8. The system of claim 1, wherein the pH value of the body of acidic pressurized liquid in the pressure vessel ranges from 2 to 6.95.

9. The system of claim 1, wherein the pre-determined pressure range of the pressure vessel ranges from 2 to 7 barg.

10. The system of claim 1, wherein a ratio of height/diameter of the body of the acidic pressurized liquid in the pressure vessel ranges from approximately 5:1 to approximately 20:1.

11. The system of claim 1, wherein a residence time of the acidic pressurized liquid in the dissolution column ranges from approximately 5 minutes to approximately 150 minutes.

12. The system of claim 1, wherein a temperature of the body of acidic pressurized liquid ranging from 10° C. to 30° C.

13. The system of claim 1, wherein the pressurized feed liquid stream is a stream of pressurized fresh water, tap water, process water, effluent water, municipal and industrial wastewater, wastewater already treated by a secondary treatment process, aqueous solutions, organic solvents.

14. The system of claim 1, wherein the fluid recirculation loop further comprises:
an ozone generator configured and adapted to generate ozone gas using oxygen gas; and
a recirculation pump, fluidly communicating with the fluid inlet and the second gas injection device, configured and adapted to elevate a pressure of the fluid slightly higher than the pressure in the pressure vessel, so as to ensure the fluid after the injection of ozone is diffused into the body of the acidic pressurized liquid in the pressure vessel through the fluid injection device.

15. The system of claim 1, further comprising:
a) a pre-treatment dissolution column comprising:
(i) a pre-treatment pressure vessel, configured and adapted to contain a body of an acidic pressurized pre-treatment liquid and a pre-treatment off gas in a pre-treatment headspace above the body of the acidic pressurized pre-treatment liquid;
(ii) a pre-treatment inlet, configured and adapted to permit passage of the pressurized feed liquid stream after the injection of the acidification agent, into the pre-treatment pressure vessel through the pre-treatment headspace;
(iii) a gas inlet in the bottom of the pre-treatment dissolution column, configured and adapted to inject a gas stream released from the pressure vessel into the body of the acidic pressurized pre-treatment liquid in the pre-treatment pressure vessel to produce a pre-treated ozonated liquid therein;
(iv) a pre-treatment off-gas vent, configured and adapted to release the pre-treatment off gas in the pre-treatment headspace so as to maintain a pressure of the pre-treatment pressure vessel with a pre-determined pressure range lower than the pressure of the pressure vessel; and
(v) a pre-treatment outlet, configured and adapted to discharge the pre-treated ozonated liquid out of the pre-treatment pressure vessel; and
b) a fluid pump, configured and adapted to pump the pre-treated ozonated liquid into the pressure vessel through the inlet of the dissolution column.

16. The system of claim 1, wherein the gas-free liquid containing ozone is ozone strong water.

17. The system of claim 15, wherein the gas-free liquid containing ozone is ozone strong water.

18. A system for continuous production of an ozone strong water, the system comprising:
a) a first gas injection device configured and adapted to inject an acidification agent into a pressurized feed water stream to maintain a pH value of the pressurized feed water stream below 7;
b) a dissolution column including:
(i) a pressure vessel, configured and adapted to contain a body of acidic pressurized water and an off gas in a headspace above the body of the acidic pressurized water;
(ii) an inlet, configured and adapted to permit passage of an acidic pressurized feed water stream, after the injection of the acidification agent, into the pressure vessel through the headspace;
(iii) an off-gas vent, configured and adapted to release the off gas contained in the headspace of the pressure vessel so as to maintain a pressure of the pressure vessel within a pre-determined pressure range; and
(iv) an outlet, configured and adapted to discharge the ozone strong water from the pressure vessel;
c) a fluid recirculation loop having
a fluid inlet, fluidly connected to the dissolution column, configured and adapted to receive a fluid from the dissolution column;
a second gas injection device, configured and adapted to inject ozone into the fluid being recirculated by the fluid recirculation loop; and
a fluid injection device, within the pressure vessel, mounted on the bottom of the pressure vessel, configured and adapted to diffuse the fluid, after the injection of ozone, into the body of the acidic pressurized water in the pressure vessel, thereby injecting ozone therein;
d) a controller, configured and adapted to adjust a flow rate of the acidic pressurized feed water stream fed to the inlet of dissolution column so as to yield an inflow of the acidic pressurized feed water stream that enables to continuously produce the ozone strong water; and
e) at least one injection nozzles each controlled by a valve, fluidly connected to the outlet of the dissolution column, configured and adapted to adjust a flow rate of the produced ozone strong water discharged from the outlet of the dissolution column to match the flow rate of the acidic pressurized feed water stream fed to the inlet of the dissolution column so as to maintain a start-up mode in an upper portion of the pressure vessel that favors a high efficiency of ozone mass transfer into the acidic pressurized water and a steady-state mode in a lower portion of the pressure vessel that favors a high dissolved ozone concentration in the acidic pressurized water coexistent in the body of the acidic pressurized water in the pressure vessel,
wherein a concentration gradient of dissolved ozone is formed along a height of the body of the acidic pressurized water.

19. The system of claim 18, wherein a pH value of the body of acidic pressurized water in the pressure vessel ranges from 2 to 6.95.

20. The system of claim 18, wherein a pH value of the body of acidic pressurized water in the pressure vessel ranges from 3 to 6.

21. The system of claim 18, wherein the pre-determined pressure range of the pressure vessel ranges from 2 to 7 barg.

22. The system of claim 18, wherein a ratio of height/diameter of the body of the acidic pressurized water in the pressure vessel ranges from approximately 5:1 to approximately 20:1.

23. The system of claim 18, wherein a residence time of the acidic pressurized water in the dissolution column ranges from approximately 5 minutes to approximately 150 minutes.

24. The system of claim 18, wherein the pressurized feed water stream is a stream of pressurized fresh water, tap water, process water, effluent water, municipal and industrial wastewater, wastewater already treated by a secondary treatment process.

25. The system of claim 18, further comprising:
a) a pre-treatment dissolution column comprising:
(i) a pre-treatment pressure vessel, configured and adapted to contain a body of the acidic pressurized pre-treatment water and a pre-treatment off gas in a pre-treatment headspace above the body of the acidic pressurized pre-treatment water;

(ii) a pre-treatment inlet, configured and adapted to permit passage of the pressurized feed water stream after the injection of the acidification agent, into the pre-treatment pressure vessel through the pre-treatment headspace;

(iii) a gas inlet in the bottom of the pre-treatment dissolution column, configured and adapted to inject the gas stream released from the pressure vessel into the body of the acidic pressurized pre-treatment water in the pre-treatment pressure vessel to produce a pre-treated ozonated water therein;

(iv) a pre-treatment off-gas vent, configured and adapted to release the pre-treatment off gas in the pre-treatment headspace so as to maintain a pressure of the pre-determined pressure vessel with a pre-determined pressure range lower than the pressure of the pressure vessel; and (v) a pre-treatment outlet, configured and adapted to discharge the pre-treated ozonated water out of the pre-treatment pressure vessel; and b) a fluid pump, configured and adapted to pump the pre-treated ozonated water into the pressure vessel through the inlet of the dissolution column.

26. The system of claim 25, wherein a concentration of the ozone strong water is larger than 150 mg/L.

27. The system of claim 25, wherein a concentration of the ozone strong water is approximately 300 mg/L.

28. A system for continuous production of a gas-free oxidant for liquid oxidation processes, the system comprising:

a) a gas injection device configured and adapted to inject an acidification agent into a pressurized feed liquid stream to maintain a pH value of the pressurized feed liquid stream below 7;

b) a dissolution column including:
  (i) a pressure vessel, configured and adapted to contain a body of acidic pressurized liquid and an off gas in a headspace above the body of the acidic pressurized liquid;
  (ii) an inlet, configured and adapted to permit passage of an acidic pressurized feed liquid stream, after the injection of the acidification agent, into the pressure vessel through the headspace;
  (iii) a fluid diffuser device within the pressure vessel, mounted on the bottom of the pressure vessel, configured and adapted to diffuse an oxidant gas into the body of the acidic pressurized liquid in the pressure vessel to dissolve the oxidant gas therein, thereby producing the gas-free oxidant for liquid oxidation processes; and
  (iv) an off-gas vent, configured and adapted to release the off gas contained in the headspace of the pressure vessel so as to maintain a pressure of the pressure vessel within a pre-determined pressure range; and
  (iv) an outlet, configured and adapted to discharge the gas-free oxidant for liquid oxidation processes from the pressure vessel;

c) a controller, configured and adapted to adjust a flow rate of the acidic pressurized feed liquid stream fed to the inlet of dissolution column so as to yield an inflow of the acidic pressurized feed liquid stream that enables to continuously produce the gas-free oxidant for liquid oxidation processes; and e) at least one injection nozzles each controlled by a valve, fluidly connected to the outlet of the dissolution column, configured and adapted to adjust a flow rate of the produced gas-free oxidant for liquid oxidation processes discharged from the outlet of the dissolution column to match the flow rate of the acidic pressurized feed liquid stream fed to the inlet of the dissolution column so as to maintain a start-up mode in an upper portion of the pressure vessel that favors a high efficiency of ozone mass transfer into the acidic pressurized liquid and a steady-state mode in a lower portion of the pressure vessel that favors a high dissolved ozone concentration in the acidic pressurized liquid coexistent in the body of the acidic pressurized liquid in the pressure vessel, wherein a concentration gradient of dissolved ozone is formed along a height of the body of the acidic pressurized liquid.

29. The system of claim 28, wherein the oxidant gas is an oxidizing substance.

30. The system of claim 28, wherein the oxidant gas is ozone.

31. The system of claim 28, wherein the acidification agent is $CO_2$ or a mineral acid.

* * * * *